United States Patent [19]
Tyrrell et al.

[11] Patent Number: 5,981,274
[45] Date of Patent: Nov. 9, 1999

[54] RECOMBINANT HEPATITIS VIRUS VECTORS

[76] Inventors: D. Lorne J. Tyrrell, 121 Laurier Drive, Edmonton, Alberta, Canada, T5R5P6; Sumonta Chaisomchit, 01A-8903, 112 Street, Edmonton, Alberta, Canada, T6G2C5; Lung-Ji Chang, 11615, 72 Avenue, Edmonton, Alberta, Canada, T6G0B9

[ * ] Notice: This patent issued on a continued prosecution application filed under 37 CFR 1.53(d), and is subject to the twenty year patent term provisions of 35 U.S.C. 154(a)(2).

[21] Appl. No.: 08/715,808

[22] Filed: Sep. 18, 1996

[51] Int. Cl.$^6$ .................................................. C12N 15/86
[52] U.S. Cl. ...................... 435/320.1; 435/243; 435/349; 435/370
[58] Field of Search ................................ 435/320.1, 370, 435/71.1, 172.3, 243, 349; 514/44; 424/93.1; 536/23

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |

FOREIGN PATENT DOCUMENTS

| | | | |
|---|---|---|---|
| WO 95/11307 | 4/1995 | WIPO | C12N 15/85 |

OTHER PUBLICATIONS

Huber et al. (1991) "Retroviral–mediated gene therapy for the treatment of hepatocellular carcinoma: An innovative approach for cancer therapy," *Proc. Natl. Acad. Sci. USA* 88:8039–8043.

Chowdhury et al. "Long–Term Improvement of Hypercholesterolemia After ex Vivo Gene Therapy in LDLR–Deficient Rabbits," *Science* 254:1802–1805.

Ledley et al. (1987) "Retroviral gene transfer into primary hepatocytes: Implications for genetic therapy of liver–specific functions," *Proc. Natl. Acad. Sci. USA* 84:5335–5339.

Wilson et al. (1988) "Retrovirus–mediated transduction of adult hepatocytes," *Proc. Natl. Acad. Sci. USA* 85:3014–3018.

Wolff et al. (1987) "Expression of retrovirally transduced genes in primary cultures of adult rat hepatocytes," *Proc. Natl. Acad. Sci. USA* 84:3344–3348.

Jaffe et al. (1992) "Adenovirus–mediated in vivo gene transfer and expression in normal rat liver," *Nature Gent.* 1:372–378.

Kaneda et al. (1989) "Increased Expression of DNA Cointroduced with Nuclear Protein in Adult Rat Liver," *Science* 243:375–378.

Wu et al. (1989) "Targeting Genes: Delivery and Persistent Expression of a Foreign Gene Driven by Mammalian Regulatory Elements in Vivo," *J. Biol. Chem.* 264(29):16985–16987.

Wilson (1992) "Hepatocyte–directed Gene Transfer in Vivo Leads to Transient Improvement of Hypercholesterolemia in Low Density Lipoprotein Receptor–deficient Rabbits," *J. Biol. Chem.* 267:963–967.

Maniatis et al. (1987) "Regulation of Inducible and Tissue–Specific Gene Expression," *Science* 236:1237–1245.

Voss et al. (1986) "The role of enhancers in the regulation of cell–type–specific transcriptional control," *Trends Biochem. Sci.* 11:287–289.

Dijkema et al. (1985) "Cloning and expression of the chromosomal immune interferon gene of the rat," *EMBO J.* 4:761–767.

Uetsuki et al. (1989) "Isolation and Characterization of the Human Chromosomal Gene for Polypeptide Chain Elongation Factor–1a," *J. Biol. Chem.* 264:5791–5798.

Kim et al. (1990) "Use of the human elongation factor 1α promoter as a versatile and efficient expression system," *Gene* 91:217–223.

Mizushima and Nagata (1990) "pEF–BOS, a powerful mammalian expression vector," *Nuc. Acids. Res.* 18:5322.

Gorman et al. (1982) "The Rous sarcoma virus long terminal repeat is a strong promoter when introduced into a variety of eukaryotic cells by DNA–mediated transfection," *Proc. Natl. Acad. Sci. USA* 79:6777–6781.

Boshart et al. (1985) "A Very Strong Enhancer Is Located Upstream of an Immediate Early Gene of Human Cytomegalovirus," *Cell* 41:521–530.

Sambrook, J. et al., *Molecular Cloning: A Laboratory Manual,* Cold Spring Harbor Press, Cold Spring Harbor, NY, pp. 7.39–7.52.

Blum et al. (1988) "Latent hepatitis B virus infection with full–length viral genome in a patient serologically immune to hepatitis B virus infection," *Liver* 8:307–316.

Ganem and Varmus (1987) "The Molecular Biology of the Hepatitis B Viruses," *Ann. Rev. Biochem.* 56:651–693.

Nassal and Schaller (1993) "Hepatitis B virus replication," *Trends Microbiol.* 1:221–228.

Rossner (1992) "Review: Hepatitis B Virus X–Gene Product: A Promiscuous Transcriptional Activator," *J. Med. Virol.* 36:101–117.

Bartenschlager and Schaller (1988) "The amino–terminal domain of the hepadnaviral P–gene encodes the terminal protein (genome–linked protein) believed to prime reverse transcription," *EMBO J.* 7:4185–4192.

Radziwill et al. (1990) "Mutational Analysis of the Hepatitis B Virus P Gene Product: Domain Structure and RNase H Activity," *J. Virol.* 64:613–620.

Schaller and Fischer (1991) "Transcriptional Control of Hepadnavirus Gene Expression," *Curr. Top. Microbiol. Immunol.* 168:21–39.

Chang et al. (1990) "Effects of Insertional and Point Mutations on the Functions of the Duck Hepatitis B Virus Polymerase," *J. Virol.* 64:5553–5558.

Eglitis et al. (1985) "Gene Expression in Mice After High Efficiency Retroviral–Mediated Gene Transfer," *Science* 230:1395–1398.

Miller et al. (1993) "Use of Retroviral Vectors for Gene Transfer and Expression," *Methods Enzymol.* 217:581–599.

Naldini et al. (1996) "In Vivo Gene Delivery and Stable Transduction of Nondividing Cells by a Lentiviral Vector," *Science* 272:263–267.

Beames and Lanford (1995) "Insertions within the Hepatitis B Virus Capsid Protein Influence Capsid Formation and RNA Encapsidation," *J. Virol.* 69:6833–6838.

Faruqi et al. (1991) "Short Communications: Replication-–Defective Missense Mutations within the Terminal Protein and Spacer/Intron Regions of the Polymerase Gene of Human Hepatitis B Virus," *Virol.* 183:764–768.

Machein et al. (1992) "Deletion and insertion mutants of HBsAg particles," *Arch. Virol. [Suppl]* 4:133–136.

Melegari et al. (1994) "Properties of Hepatitis B Virus Pre–S1 Deletion Mutants," *Virol.* 199:292–300.

Nakatake et al. (1993) "Effect of X Protein on Transactivation of Hepatitis B Virus Promoters and on Viral Replication," *Virol.* 95:305–314.

Bartenschlager et al. (1990) "The P Gene Product of Hepatitis B Virus Is Required as a Structural Component for Genomic RNA Encapsidation," *J. Virol.* 64:5324–5332.

Hirsch et al. (1990) "Polymerase gene products of hepatitis B viruses are required for genomic RNA packaging as well as for reverse transcription," *Nature* 344:552–555.

Li et al. (1989) "Duck Hepatitis B Virus Can Tolerate Insertion, Deletion, and Partial Frameshift Mutation in the Distal Pre–S Region," *J. Virol.* 63:4965–4968.

Takebe et al. (1988) "SRα Promoter: an Efficient and Versatile Mammalian cDNA Expression System Composed of the Simian Virus 40 Early Promoter and the R–U5 Segment of Human T–Cell Leukemia Virus Type 1 Long Terminal Repeat," *Mol. Cell. Biol.* 8:466–472.

Graham et al. (1977) "Characteristics of a Human Cell Line Transformed by DNA from Human Adenovirus Type 5," *J. Gen. Virol.* 36:59–72.

Harrison et al. (1977) "Host–Range Mutants of Adenovirus Type 5 Defective for Growth in HeLa Cells," *Virology* 77:319–329.

Graham et al. (1978) "Defective Transforming Capacity of Adenovirus Type 5 Host–Range Mutants," *Virology* 86:10–21.

Robinson (1990) "Hepadnaviridae and Their Replication," in *Hepadnaviridae and their replication,* Fields et al. eds., Fields Virology, Raven Press, Ltd. N.Y., pp. 2137–2169.

Robinson et al. (1995) "Retroviral vector with a CMV–IE/HIV–TAR hybrid LTR gives high basal expression levels and is up–regulated by HIV–1 Tat," *Gene Therapy* 2:269–278.

Chang et al. (1993) "Human Immunodeficiency Viruses Containing Heterologous Enhancer/Promoters Are Replication Competent and Exhibit Different Lymphocyte Tropisms," *J. Virol.* 76:743–752.

Peterlin et al. (1986) "Elevated levels of mRNA can account for the trans–activation of human immunodeficiency virus," *Proc. Natl. Acad. Sci. USA* 83:9734–9738 (1986).

Condreay et al. (1990) "Efficient Duck Hepatitis B Virus Production by an Avian Liver Tumor Cell Line," *J. Virol.* 64:3249–3258.

Shaul (1991), Regulation of hepadnavirus transcription, A McLachlan (ed.), in *Molecular biology of hepatitis B viruses,* CRC Press, Boca Raton, FL; This reference is not currently available; should the Examiner desire a copy, please let Applicants know so that one may be provided.

Patel et al. (1989) "Interactions between Nuclear Factors and the Hepatitis B Virus Enhancer," *J. Virol.* 63:5293–5301.

Jameel and Siddiqui (1986) "The Human Hepatitis B Virus Enhancer Requires trans–Acting Cellular Factor(s) for Activity," *Mol. Cell. Biol.* 6:710–715.

Siddiqui et al. (1989) "trans–Activation of Viral Enhancers Including Long Terminal Repeat of the Human Immunodeficiency Virus by the Hepatitis B Virus X Protein," *Virol.* 169:479–484.

Twu et al. (1990) "Transcriptional Activation of the Human Immunodeficiency Virus Type 1 Long Terminal Repeat by Hepatitis B Virus X–Protein Requires de Novo Protein Synthesis," *Virol.* 177:406–410.

Picard et al. (1994) "Rapid and efficient one–tube PCR-–based mutagenesis technique using Pfu DNA polymerase," *Nucleic Acids Res.* 22:2587–2591.

Seifer et al. (1990) "Replication of Hepatitis B Virus in Transfected Nonhepatic Cells," *Virol.* 179:300–311.

Persing et al. (1986) "Inhibition of Secretion of Hepatitis B Surface Antigen by a Related Presurface Polypeptide," *Science* 234:1388–1391.

Tsang et al. (1993) "Loss of Resolution in Gel Electrophoresis of RNA: A Problem Associated with the Presence of Formaldehyde Gradients," *BioTechniques* 14:380–381.

Hirsch et al. (1991) "cis–Acting Sequences Required for Encapsidation of Duck Hepatitis B Virus Pregenomic RNA," *J. Virol.* 65:3309–3316.

Junker–Neipmann et al. (1990) "A short cis–acting sequence is required for hepatitis B virus pregenome encapsidation and sufficient for packaging of foreign RNA," *EMBO J.* 9:3389–3396.

Hantz et al. (1992) "Viral Spliced RNA are Produced, Encapsidated and Reverse Transcribed during in Vivo Woodchuck Hepatitis Virus Infection," *Virol.* 190:193–200.

Obert et al. (1996) "A spliced hepadnavirus RNA that is essential for virus replication," *EMBO J.* 15:2565–2574.

Wu et al. (1991) "Characterization and Genetic Analysis of Altenatively Spliced Transcripts of Hepatitis B Virus in Infected Human Liver Tissues and Transfected HepG2 Cells," *J. Virol.* 65:1680–1686.

Bruss and Ganem (1991) "The Role of envelope proteins in hepatitis B virus assembly," *Proc. Natl. Acad. Sci. USA* 88:1059–1063.

Sheu and Lo (1995) "Deletion or alteration of hydrophobic amino acids at the first and the third transmembrane domains of hepatitis B surface antigen enhances its production in *Escherichia coli*," *Gene* 160:179–184.

Bruss and Vieluf (1995) "Functions of the Internal Pre–S Domain of the Large Surface Protein in Hepatitis B Virus Particle Morphogenesis," *J. Virol.* 69:6652–6657.

Höhne et al. (1990) "Malignant transformation of immortalized transgenic hepatocytes after transfection with hepatitis B virus DNA," *EMBO J.* 9:1137–1145.

Koike et al. (1989) "Oncogenic Potential of Hepatitis B Virus," *Mol. Biol. Med.* 6:151–160.

Lu et al. (1996) "Protease–Induced Infectivity of Hepatitis B Virus for a Human Heopatoblastoma Cell Line," *J. Virol.* 70:2277–2285.

Horwich et al. (1990) "Synthesis of Hepadnavirus Particles That Contain Replication–Defective Duck Hepatitis B Virus Genomes in Cultured HuH7 Cells," *Journal of Virology* 64(2):642–650.

Mulligan (1993) "The Basic Science of Gene Therapy," *Science* 260:926–932.

Schaller and Fischer (1991) "Transcriptional Control of Hepadnavirus Gene Expression," *Current Topics in Microbiology and Immunology* 160:21–39.

Barinaga, M. Science vol. , 266, p. 1326, Nov. 25, 1994.

Marshall, E.M. Science, vol. 269, pp. 1050–1055, Aug. 25, 1995.

Crystal, R.G. Science, vol. 270, pp. 404–410, 1995.

Jolly, D. Cancer Gene Therapy, vol. 1(1), pp. 51–64, 1994.

Orkin et al. Report and Recommendations of the Panel to Assess the NIH Investment in Research on Gene Therapy, Dec. 7, 1995.

Zern et al. Hepatology, vol. 25(2), pp. 484–491, Feb. 1997.

*Primary Examiner*—James Ketter
*Assistant Examiner*—Irem Yucel
*Attorney, Agent, or Firm*—Iver P. Cooper

[57] ABSTRACT

The present invention relates to recombinant hepatitis viral vectors useful for the expression of functional heterologous gene products in liver cells. It is contemplated that these vectors will find use in anti-viral, anti-tumor and/or gene therapy, particularly for the correction of inherited single-gene defects. These novel recombinant vectors may be used to deliver genes to cells in vivo by a variety of means including infection and direct injection of vector DNA.

25 Claims, 7 Drawing Sheets

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 3221 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:1:

```
AATTCCACTG CCTTCCACCA AACTCTGCAG GATCCCAGAG TCAGGGGTCT GTATCTTCCT      60

GCTGGTGGCT CCAGTTCAGG AACAGTAAAC CCTGCTCCGA ATATTGCCTC TCACATCTCG     120

TCAATCTCCG CGAGGACTGG GGACCCTGTG ACGAACATGG AGAACATCAC ATCAGGATTC     180

CTAGGACCCC TGCTCGTGTT ACAGGCGGGG TTTTTCTTGT TGACAAGAAT CCTCACAATA     240

CCGCAGAGTC TAGACTCGTG GTGGACTTCT CTCAATTTTC TAGGGGGATC TCCCGTGTGT     300

CTTGGCCAAA ATTCGCAGTC CCCAACCTCC AATCACTCAC CAACCTCCTG TCCTCCAATT     360

TGTCCTGGTT ATCGCTGGAT GTGTCTGCGG CGTTTTATCA TATTCCTCTT CATCCTGCTG     420

CTATGCCTCA TCTTCTTATT GGTTCTTCTG GATTATCAAG GTATGTTGCC CGTTTGTCCT     480

CTAATTCCAG GATCAACAAC AACCAGTACG GGACCATGCA AAACCTGCAC GACTCCTGCT     540

CAAGGCAACT CTATGTTTCC CTCATGTTGC TGTACAAAAC CTACGGATGG AAATTGCACC     600

TGTATTCCCA TCCCATCGTC CTGGGCTTTC GCAAAATACC TATGGGAGTG GGCCTCAGTC     660

CGTTTCTCTT GGCTCAGTTT ACTAGTGCCA TTTGTTCAGT GGTTCGTAGG GCTTTCCCCC     720

ACTGTTTGGC TTTCAGCTAT ATGGATGATG TGGTATTGGG GGCCAAGTCT GTACAGCATC     780

GTGAGTCCCT TTATACCGCT GTTACCAATT TTCTTTTGTC TCTGGGTATA CATTTAAACC     840
```

```
CTAACAAAAC AAAAAGATGG GGTTATTCCC TAAACTTCAT GGGCTACATA ATTGGAAGTT      900
GGGGAACTTT GCCACAGGAT CATATTGTAC AAAAGATCAA ACACTGTTTT AGAAAACTTC      960
CTGTTAACAG GCCTATTGAT TGGAAAGTAT GTCAAAGAAT TGTGGGTCTT TTGGGCTTTG     1020
CTGCTCCATT TACACAATGT GGATATCCTG CCTTAATGCC TTTGTATGCA TGTATACAAG     1080
CTAAACAGGC TTTCACTTTC TCGCCAACTT ACAAGGCCTT TCTAAGTAAA CAGTACATGA     1140
ACCTTTACCC CGTTGCTCGG CAACGGCCTG GTCTGTGCCA AGTGTTTGCT GACGCAACCC     1200
CCACTGGCTG GGGCTTGGCC ATAGGCCATC AGCGCATGCG TGGAACCTTT GTGGCTCCTC     1260
TGCCGATCCA TACTGCGGAA CTCCTAGCCG CTTGTTTTGC TCGCAGCCGG TCTGGAGCAA     1320
AGCTCATCGG AACTGACAAT TCTGTCGTCC TCTCGCGGAA ATATACATCG TTTCCATGGC     1380
TGCTAGGCTG TACTGCCAAC TGGATCCTTC GCGGGACGTC CTTTGTTTAC GTCCCGTCGG     1440
CGCTGAATCC CGCGGACGAC CCCTCTCGGG GCCGCTTGGG ACTCTCTCGT CCCCTTCTCC     1500
GTCTGCCGTT CCAGCCGACC ACGGGGCGCA CCTCTCTTTA CGCGGTCTCC CCGTCTGTGC     1560
CTTCTCATCT GCCGGTCCGT GTGCACTTCG CTTCACCTCT GCACGTTGCA TGGAGACCAC     1620
CGTGAACGCC CATCAGATCC TGCCCAAGGT CTTACATAAG AGGACTCTTG GACTCCCAGC     1680
AATGTCAACG ACCGACCTTG AGGCCTACTT CAAAGACTGT GTGTTTAAGG ACTGGGAGGA     1740
GCTGGGGGAG GAGATTAGGT TAAAGGTCTT TGTATTAGGA GGCTGTAGGC ACAAATTGGT     1800
CTGCGCACCA GCACCATGCA ACTTTTTCAC CTCTGCCTAA TCATCTCTTG TACATGTCCC     1860
ACTGTTCAAG CCTCCAAGCT GTGCCTTGGG TGGCTTTGGG GCATGGACAT TGACCCTTAT     1920
AAAGAATTTG GAGCTACTGT GGAGTTACTC TCGTTTTTGC CTTCTGACTT CTTTCCTTCC     1980
GTCAGAGATC TCCTAGACAC CGCCTCAGCT CTGTATCGAG AAGCCTTAGA GTCTCCTGAG     2040
CATTCCTCAC CTCACCATAC TGCACTCAGG CAAGCCATTC TCTGCTGGGG GGAATTGATG     2100
ACTCTAGCTA CCTGGGTGGG TAATAATTTG GAAGATCCAG CATCTAGGGA TCTTGTAGTA     2160
AATTATGTTA ATACTAACGT GGGTTTAAAG ATCAGGCAAC TATTGTGGTT TCATATATCT     2220
TGCCTTACTT TTGGAAGAGA GACTGTACTT GAATATTTGG TCTCTTTCGG AGTGTGGATT     2280
CGCACTCCTC CAGCCTATAG ACCACCAAAT GCCCCTATCT TATCAACACT TCCGGAAACT     2340
ACTGTTGTTA GACGACGGGA CCGAGGCAGG TCCCCTAGAA GAAGAACTCC CTCGCCTCGC     2400
AGACGCAGAT CTCCATCGCC GCGTCGCAGA AGATCTCAAT CTCGGGAATC TCAATGTTAG     2460
TATTCCTTGG ACTCATAAGG TGGGAAACTT TACGGGGCTT TATTCCTCTA CAGTACCTAT     2520
CTTTAATCCT GAATGGCAAA CTCCTTCCTT TCCTAAGATT CATTTACAAG AGGACATTAT     2580
TAATAGGTGT CAACAATTTG TGGGCCCTCT CACTGTAAAT GAAAAGAGAA GATTGAAATT     2640
AATTATGCCT GCTAGATTCT ATCCTACCCA CACTAAATAT TTGCCCTTAG ACAAAGGAAT     2700
TAAACCTTAT TATCCAGATC AGGTAGTTAA TCATTACTTC CAAACCAGAC ATTATTTACA     2760
TACTCTTTGG AAGGCTGGTA TTCTATATAA GCGGGAAACC ACACGTAGCG CATCATTTTG     2820
CGGGTCACCA TATTCTTGGG AACAAGAGCT ACAGCATGGG AGGTTGGTCA TCAAAACCTC     2880
GCAAAGGCAT GGGGACGAAT CTTTCTGTTC CCAATCCTCT GGGATTCTTT CCCGATCATC     2940
AGTTGGACCC TGCATTCGGA GCCAACTCAA ACAATCCAGA TTGGGACTTC AACCCCGTCA     3000
AGGACGACTG GCCAGCAGCC AACCAAGTAG GAGTGGGAGC ATTCGGGCCA AGGCTCACCC     3060
CTCCACACGG CGGTATTTTG GGGTGGAGCC CTCAGGCTCA GGGCATATTG ACCACAGTGT     3120
CAACAATTCC TCCTCCTGCC TCCACCAATC GGCAGTCAGG AAGGCAGCCT ACTCCCATCT     3180
CTCCACCTCT AAGAGACAGT CATCCTCAGG CCATGCAGTG G                        3221
```

(2) INFORMATION FOR SEQ ID NO:2:

(i) SEQUENCE CHARACTERISTICS:
        (A) LENGTH: 9325 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA"

(xi) SEQUENCE DESCRIPTION: SEQ ID NO:2:

```
CCCATTCGCC ATTCAGGCTG CGCAACTGTT GGGAAGGGCG ATCGGTGCGG GCCTCTTCGC      60
TATTACGCCA GCTGGCGAAA GGGGGATGTG CTGCAAGGCG ATTAAGTTGG GTAACGCCAG     120
GGTTTTCCCA GTCACGACGT TGTAAAACGA CGGCCAGTGC CAAGCTATAT AAATTAACCC     180
TCACTAAAGG GAATAAGCTT GCATGCCTGC AGGTCGACTC TAGAGGATCC CCGGGTACCG     240
AGCTCGAATT CCACTGCCTT CCACCAAACT CTGCAGGATC CCAGAGTCAG GGTCTGTAT      300
CTTCCTGCTG GTGGCTCCAG TTCAGGAACA GTAAACCCTG CTCCGAATAT TGCCTCTCAC     360
ATCTCGTCAA TCTCCGCGAG GACTGGGGAC CCTGTGACGA ACATGGAGAA CATCACATCA     420
GGATTCCTAG GACCCCTGCT CGTGTTACAG GCGGGGTTTT TCTTGTTGAC AAGAATCCTC     480
ACAATACCGC AGAGTCTAGA CTCGTGGTGG ACTTCTCTCA ATTTTCTAGG GGGATCTCCC     540
GTGTGTCTTG GCCAAAATTC GCAGTCCCCA ACCTCCAATC ACTCACCAAC CTCCTGTCCT     600
CCAATTTGTC CTGGTTATCG CTGGATGTGT CTGCGGCGTT TTATCATATT CCTCTTCATC     660
CTGCTGCTAT GCCTCATCTT CTTATTGGTT CTTCTGGATT ATCAAGGTAT GTTGCCCGTT     720
TGTCCTCTAA TTCCAGGATC AACAACAACC AGTACGGAC CATGCAAAAC CTGCACGACT      780
CCTGCTCAAG GCAACTCTAT GTTTCCCTCA TGTTGCTGTA CAAAACCTAC GGATGGAAAT     840
TGCACCTGTA TTCCCATCCC ATCGTCCTGG GCTTTCGCAA AATACCTATG GGAGTGGGCC     900
TCAGTCCGTT TCTCTTGGCT CAGTTTACTA GTGCCATTTG TTCAGTGGTT CGTAGGGCTT     960
TCCCCCACTG TTTGGCTTTC AGCTATATGG ATGATGTGGT ATTGGGGGCC AAGTCTGTAC    1020
AGCATCGTGA GTCCCTTTAT ACCGCTGTTA CCAATTTTCT TTTGTCTCTG GTATACATTT    1080
TAAACCCTAA CAAAACAAAA AGATGGGGTT ATTCCCTAAA CTTCATGGGC TACATAATTG    1140
GAAGTTGGGG AACTTTGCCA CAGGATCATA TTGTACAAAA GATCAAACAC TGTTTTAGAA    1200
AACTTCCTGT TAACAGGCCT ATTGATTGGA AAGTATGTCA AAGAATTGTG GGTCTTTTGG    1260
GCTTTGCTGC TCCATTTACA CAATGTGGAT ATCCTGCCTT AATGCCTTTG TATGCATGTA    1320
TACAAGCTAA ACAGGCTTTC ACTTTCTCGC CAACTTACAA GGCCTTTCTA AGTAAACAGT    1380
ACATGAACCT TTACCCCGTT GCTCGGCAAC GGCCTGGTCT GTGCCAAGTG TTTGCTGACG    1440
CAACCCCCAC TGGCTGGGGC TTGGCCATAG GCCATCAGCG CATGCGTGGA ACCTTTGTGG    1500
CTCCTCTGCC GATCCATACT GCGGAACTCC TAGCCGCTTG TTTTGCTCGC AGCCGGTCTG    1560
GAGCAAAGCT CATCGGAACT GACAATTCTG TCGTCCTCTC GCGGAAATAT ACATCGTTTC    1620
CATGGCTGCT AGGCTGTACT GCCAACTGGA TCCTTCGCGG GACGTCCTTT GTTTACGTCC    1680
CGTCGGCGCT GAATCCCGCG GACGACCCCT CTCGGGGCCG CTTGGGACTC TCTCGTCCCC    1740
TTCTCCGTCT GCCGTTCCAG CCGACCACGG GGCGCACCTC TCTTTACGCG GTCTCCCCGT    1800
CTGTGCCTTC TCATCTGCCG GTCCGTGTGC ACTTCGCTTC ACCTCTGCAC GTTGCATGGA    1860
GACCACCGTG AACGCCCATC AGATCCTGCC CAAGGTCTTA CATAAGAGGA CTCTTGGACT    1920
CCCAGCAATG TCAACGACCG ACCTTGAGGC CTACTTCAAA GACTGTGTGT TTAAGGACTG    1980
```

-continued

```
GGAGGAGCTG GGGGAGGAGA TTAGGTTAAA GGTCTTTGTA TTAGGAGGCT GTAGGCACAA    2040

ATTGGTCTGC GCACCAGCAC CATGCAACTT TTTCACCTCT GCCTAATCAT CTCTTGTACA    2100

TGTCCCACTG TTCAAGCCTC CAAGCTGTGC CTTGGGTGGC TTTGGGGCAT GGACATTGAC    2160

CCTTATAAAG AATTTGGAGC TACTGTGGAG TTACTCTCGT TTTTGCCTTC TGACTTCTTT    2220

CCTTCCGTCA GAGATCTCCT AGACACCGCC TCAGCTCTGT ATCGAGAAGC CTTAGAGTCT    2280

CCTGAGCATT CCTCACCTCA CCATACTGCA CTCAGGCAAG CCATTCTCTG CTGGGGGAA     2340

TTGATGACTC TAGCTACCTG GGTGGGTAAT AATTTGGAAG ATCCAGCATC TAGGGATCTT    2400

GTAGTAAATT ATGTTAATAC TAACGTGGGT TTAAAGATCA GGCAACTATT GTGGTTTCAT    2460

ATATCTTGCC TTACTTTTGG AAGAGAGACT GTACTTGAAT ATTTGGTCTC TTTCGGAGTG    2520

TGGATTCGCA CTCCTCCAGC CTATAGACCA CCAAATGCCC CTATCTTATC AACACTTCCG    2580

GAAACTACTG TTGTTAGACG ACGGGACCGA GGCAGGTCCC CTAGAAGAAG AACTCCCTCG    2640

CCTCGCAGAC GCAGATCTCC ATCGCCGCGT CGCAGAAGAT CTCAATCTCG GAATCTCAA     2700

TGTTAGTATT CCTTGGACTC ATAAGGTGGG AAACTTTACG GGCTTTATT CCTCTACAGT    2760

ACCTATCTTT AATCCTGAAT GGCAAACTCC TTCCTTTCCT AAGATTCATT TACAAGAGGA    2820

CATTATTAAT AGGTGTCAAC AATTTGTGGG CCCTCTCACT GTAAATGAAA AGAGAAGATT    2880

GAAATTAATT ATGCCTGCTA GATTCTATCC TACCCACACT AAATATTTGC CCTTAGACAA    2940

AGGAATTAAA CCTTATTATC CAGATCAGGT AGTTAATCAT TACTTCCAAA CCAGACATTA    3000

TTTACATACT CTTTGGAAGG CTGGTATTCT ATATAAGCGG GAAACCACAC GTAGCGCATC    3060

ATTTTGCGGG TCACCATATT CTTGGGAACA AGAGCTACAG CATGGGAGGT TGGTCATCAA    3120

AACCTCGCAA AGGCATGGGG ACGAATCTTT CTGTTCCCAA TCCTCTGGGA TTCTTTCCCG    3180

ATCATCAGTT GGACCCTGCA TTCGGAGCCA ACTCAAACAA TCCAGATTGG GACTTCAACC    3240

CCGTCAAGGA CGACTGGCCA GCAGCCAACC AAGTAGGAGT GGGAGCATTC GGGCCAAGGC    3300

TCACCCCTCC ACACGGCGGT ATTTTGGGGT GGAGCCCTCA GGCTCAGGGC ATATTGACCA    3360

CAGTGTCAAC AATTCCTCCT CCTGCCTCCA CCAATCGGCA GTCAGGAAGG CAGCCTACTC    3420

CCATCTCTCC ACCTCTAAGA GACAGTCATC CTCAGGCCAT GCAGTGGAAT TCCACTGCCT    3480

TCCACCAAAC TCTGCAGGAT CCCAGAGTCA GGGGTCTGTA TCTTCCTGCT GGTGGCTCCA    3540

GTTCAGGAAC AGTAAACCCT GCTCCGAATA TTGCCTCTCA CATCTCGTCA ATCTCCGCGA    3600

GGACTGGGGA CCCTGTGACG AACATGGAGA ACATACACATC AGGATTCCTA GGACCCCTGC   3660

TCGTGTTACA GGCGGGGTTT TTCTTGTTGA CAAGAATCCT CACAATACCG CAGAGTCTAG    3720

ACTCGTGGTG GACTTCTCTC AATTTTCTAG GGGGATCTCC CGTGTGTCTT GGCCAAAATT    3780

CGCAGTCCCC AACCTCCAAT CACTCACCAA CCTCCTGTCC TCCAATTTGT CCTGGTTATC    3840

GCTGGATGTG TCTGCGGCGT TTTATCATAT TCCTCTTCAT CCTGCTGCTA TGCCTCATCT    3900

TCTTATTGGT TCTTCTGGAT TATCAAGGTA TGTTGCCCGT TTGTCCTCTA ATTCCAGGAT    3960

CAACAACAAC CAGTACGGGA CCATGCAAAA CCTGCACGAC TCCTGCTCAA GGCAACTCTA    4020

TGTTTCCCTC ATGTTGCTGT ACAAAACCTA CGGATGGAAA TTGCACCTGT ATTCCCATCC    4080

CATCGTCCTG GGCTTTCGCA AAATACCTAT GGGAGTGGGC CTCAGTCCGT TTCTCTTGGC    4140

TCAGTTTACT AGTGCCATTT GTTCAGTGGT TCGTAGGGCT TTCCCCCACT GTTTGGCTTT    4200

CAGCTATATG GATGATGTGG TATTGGGGGC CAAGTCTGTA CAGCATCGTG AGTCCCTTTA    4260

TACCGCTGTT ACCAATTTTC TTTTGTCTCT GGGTATACAT TTAAACCCTA ACAAAACAAA    4320

AAGATGGGGT TATTCCCTAA ACTTCATGGG CTACATAATT GGAAGTTGGG GAACTTTGCC    4380
```

```
ACAGGATCAT ATTGTACAAA AGATCAAACA CTGTTTTAGA AAACTTCCTG TTAACAGGCC     4440

TATTGATTGG AAAGTATGTC AAAGAATTGT GGGTCTTTTG GGCTTTGCTG CTCCATTTAC     4500

ACAATGTGGA TATCCTGCCT TAATGCCTTT GTATGCATGT ATACAAGCTA AACAGGCTTT     4560

CACTTTCTCG CCAACTTACA AGGCCTTTCT AAGTAAACAG TACATGAACC TTTACCCCGT     4620

TGCTCGGCAA CGGCCTGGTC TGTGCCAAGT GTTTGCTGAC GCAACCCCCA CTGGCTGGGG     4680

CTTGGCCATA GGCCATCAGC GCATGCGTGG AACCTTTGTG CTCCTCTGC CGATCCATAC     4740

TGCGGAACTC CTAGCCGCTT GTTTTGCTCG CAGCCGGTCT GGAGCAAAGC TCATCGGAAC     4800

TGACAATTCT GTCGTCCTCT CGCGGAAATA TACATCGTTT CCATGGCTGC TAGGCTGTAC     4860

TGCCAACTGG ATCCTTCGCG GGACGTCCTT TGTTTACGTC CCGTCGGCGC TGAATCCCGC     4920

GGACGACCCC TCTCGGGGCC GCTTGGGACT CTCTCGTCCC CTTCTCCGTC TGCCGTTCCA     4980

GCCGACCACG GGGCGCACCT CTCTTTACGC GGTCTCCCCG TCTGTGCCTT CTCATCTGCC     5040

GGTCCGTGTG CACTTCGCTT CACCTCTGCA CGTTGCATGG AGACCACCGT GAACGCCCAT     5100

CAGATCCTGC CCAAGGTCTT ACATAAGAGG ACTCTTGGAC TCCCAGCAAT GTCAACGACC     5160

GACCTTGAGG CCTACTTCAA AGACTGTGTG TTTAAGGACT GGGAGGAGCT GGGGGAGGAG     5220

ATTAGGTTAA AGGTCTTTGT ATTAGGAGGC TGTAGGCACA AATTGGTCTG CGCACCAGCA     5280

CCATGCAACT TTTTCACCTC TGCCTAATCA TCTCTTGTAC ATGTCCCACT GTTCAAGCCT     5340

CCAAGCTGTG CCTTGGGTGG CTTTGGGCA TGGACATTGA CCCTTATAAA GAATTTGGAG     5400

CTACTGTGGA GTTACTCTCG TTTTTGCCTT CTGACTTCTT TCCTTCCGTC AGAGATCTCC     5460

TAGACACCGC CTCAGCTCTG TATCGAGAAG CCTTAGAGTC TCCTGAGCAT TCCTCACCTC     5520

ACCATACTGC ACTCAGGCAA GCCATTCTCT GCTGGGGGA ATTGATGACT CTAGCTACCT     5580

GGGTGGGTAA TAATTTGGAA GATCCAGCAT CTAGGGATCT TGTAGTAAAT TATGTTAATA     5640

CTAACGTGGG TTTAAAGATC AGGCAACTAT TGTGGTTTCA TATATCTTGC CTTACTTTTG     5700

GAAGAGAGAC TGTACTTGAA TATTTGGTCT CTTTCGGAGT GTGGATTCGC ACTCCTCCAG     5760

CCTATAGACC ACCAAATGCC CCTATCTTAT CAACACTTCC GGAAACTACT GTTGTTAGAC     5820

GACGGGACCG AGGCAGGTCC CCTAGAAGAA GAACTCCCTC GCCTCGCAGA CGCAGATCTC     5880

CATCGCCGCG TCGCAGAAGA TCTCAATCTC GGGAATCTCA ATGTTAGTAT TCCTTGGACT     5940

CATAAGGTGG GAAACTTTAC GGGGCTTTAT TCCTCTACAG TACCTATCTT TAATCCTGAA     6000

TGGCAAACTC CTTCCTTTCC TAAGATTCAT TTACAAGAGG ACATTATTAA TAGGTGTCAA     6060

CAATTTGTGG GCCCTCTCAC TGTAAATGAA AAGAGAAGAT TGAAATTAAT TATGCCTGCT     6120

AGATTCTATC CTACCCACAC TAAATATTTG CCCTTAGACA AAGGAATTAA ACCTTATTAT     6180

CCAGATCAGG TAGTTAATCA TTACTTCCAA ACCAGACATT ATTTACATAC TCTTTGGAAG     6240

GCTGGTATTC TATATAAGCG GGAAACCACA CGTAGCGCAT CATTTTGCGG GTCACCATAT     6300

TCTTGGGAAC AAGAGCTACA GCATGGGAGG TTGGTCATCA AAACCTCGCA AAGGCATGGG     6360

GACGAATCTT TCTGTTCCCA ATCCTCTGGG ATTCTTTCCC GATCATCAGT TGGACCCTGC     6420

ATTCGGAGCC AACTCAAACA ATCCAGATTG GGACTTCAAC CCCGTCAAGG ACGACTGGCC     6480

AGCAGCCAAC CAAGTAGGAG TGGGAGCATT CGGGCCAAGG CTCACCCCTC CACACGGCGG     6540

TATTTTGGGG TGGAGCCCTC AGGCTCAGGG CATATTGACC ACAGTGTCAA CAATTCCTCC     6600

TCCTGCCTCC ACCAATCGGC AGTCAGGAAG GCAGCCTACT CCCATCTCTC CACCTCTAAG     6660

AGACAGTCAT CCTCAGGCCA TGCAGTGGAA TTCCCTATAG TGAGTCGTAT TAAATTCGTA     6720

ATCATGGTCA TAGCTGTTTC CTGTGTGAAA TTGTTATCCG CTCACAATTC CACACAACAT     6780
```

```
ACGAGCCGGA AGCATAAAGT GTAAAGCCTG GGGTGCCTAA TGAGTGAGCT AACTCACATT    6840

AATTGCGTTG CGCTCACTGC CCGCTTTCCA GTCGGGAAAC CTGTCGTGCC AGCTGCATTA    6900

ATGAATCGGC CAACGCGCGG GGAGAGGCGG TTTGCGTATT GGGCGCTCTT CCGCTTCCTC    6960

GCTCACTGAC TCGCTGCGCT CGGTCGTTCG GCTGCGGCGA GCGGTATCAG CTCACTCAAA    7020

GGCGGTAATA CGGTTATCCA CAGAATCAGG GGATAACGCA GGAAAGAACA TGTGAGCAAA    7080

AGGCCAGCAA AAGGCCAGGA ACCGTAAAAA GGCCGCGTTG CTGGCGTTTT CCATAGGCT    7140

CCGCCCCCCT GACGAGCATC ACAAAAATCG ACGCTCAAGT CAGAGGTGGC GAAACCCGAC    7200

AGGACTATAA AGATACCAGG CGTTTCCCCC TGGAAGCTCC CTCGTGCGCT CTCCTGTTCC    7260

GACCCTGCCG CTTACCGGAT ACCTGTCCGC CTTTCTCCCT TCGGGAAGCG TGGCGCTTTC    7320

TCAATGCTCA CGCTGTAGGT ATCTCAGTTC GGTGTAGGTC GTTCGCTCCA AGCTGGGCTG    7380

TGTGCACGAA CCCCCCGTTC AGCCCGACCG CTGCGCCTTA TCCGGTAACT ATCGTCTTGA    7440

GTCCAACCCG GTAAGACACG ACTTATCGCC ACTGGCAGCA GCCACTGGTA ACAGGATTAG    7500

CAGAGCGAGG TATGTAGGCG GTGCTACAGA GTTCTTGAAG TGGTGGCCTA ACTACGGCTA    7560

CACTAGAAGA ACAGTATTTG GTATCTGCGC TCTGCTGAAG CCAGTTACCT TCGGAAAAAG    7620

AGTTGGTAGC TCTTGATCCG GCAAACAAAC CACCGCTGGT AGCGGTGGTT TTTTTGTTTG    7680

CAAGCAGCAG ATTACGCGCA GAAAAAAAGG ATCTCAAGAA GATCCTTTGA TCTTTTCTAC    7740

GGGGTCTGAC GCTCAGTGGA ACGAAAACTC ACGTTAAGGG ATTTTGGTCA TGAGATTATC    7800

AAAAAGGATC TTCACCTAGA TCCTTTTAAA TTAAAAATGA AGTTTTAAAT CAATCTAAAG    7860

TATATATGAG TAAACTTGGT CTGACAGTTA CCAATGCTTA ATCAGTGAGG CACCTATCTC    7920

AGCGATCTGT CTATTTCGTT CATCCATAGT TGCCTGACTC CCCGTCGTGT AGATAACTAC    7980

GATACGGGAG GGCTTACCAT CTGGCCCCAG TGCTGCAATG ATACCGCGAG ACCCACGCTC    8040

ACCGGCTCCA GATTTATCAG CAATAAACCA GCCAGCCGGA AGGGCCGAGC GCAGAAGTGG    8100

TCCTGCAACT TTATCCGCCT CCATCCAGTC TATTAATTGT TGCCGGGAAG CTAGAGTAAG    8160

TAGTTCGCCA GTTAATAGTT TGCGCAACGT TGTTGCCATT GCTACAGGCA TCGTGGTGTC    8220

ACGCTCGTCG TTTGGTATGG CTTCATTCAG CTCCGGTTCC CAACGATCAA GGCGAGTTAC    8280

ATGATCCCCC ATGTTGTGCA AAAAAGCGGT TAGCTCCTTC GGTCCTCCGA TCGTTGTCAG    8340

AAGTAAGTTG GCCGCAGTGT TATCACTCAT GGTTATGGCA GCACTGCATA ATTCTCTTAC    8400

TGTCATGCCA TCCGTAAGAT GCTTTTCTGT GACTGGTGAG TACTCAACCA AGTCATTCTG    8460

AGAATAGTGT ATGCGGCGAC CGAGTTGCTC TTGCCCGGCG TCAATACGGG ATAATACCGC    8520

GCCACATAGC AGAACTTTAA AAGTGCTCAT CATTGGAAAA CGTTCTTCGG GGCGAAAACT    8580

CTCAAGGATC TTACCGCTGT TGAGATCCAG TTCGATGTAA CCCACTCGTG CACCCAACTG    8640

ATCTTCAGCA TCTTTTACTT TCACCAGCGT TTCTGGGTGA GCAAAAACAG GAAGGCAAAA    8700

TGCCGCAAAA AAGGGAATAA GGGCGACACG GAAATGTTGA ATACTCATAC TCTTCCTTTT    8760

TCAATATTAT TGAAGCATTT ATCAGGGTTA TTGTCTCATG AGCGGATACA TATTTGAATG    8820

TATTTAGAAA AATAAACAAA TAGGGGTTCC GCGCACATTT CCCCGAAAAG TGCCACCTGA    8880

AATTGTAAAC GTTAATGTTT TGTTAAATTT CGCGTTAAAT ATTTGTTAAA TCAGCTTATT    8940

TTTTAACCAG TAAGCAGAAA ATGACAAAAA TCCTTATAAA TCAAAAGAAT AGACCGAGTT    9000

AGTTGTGAGT GTTGTTCCAG TTTGGAACAA GAGTCCACTA TTAAAGAACG TGGACTCCAA    9060

CGTAAAACCG TCTATCAGGG CGATGGCCCA CTACGTGAAC CATCACCCAA ATCAAGTTTT    9120

TGGAGGTCGA GGTGCCGTAA AGCACTAAAT CGGAACCCTA AAGGGAGCCC CCGATTTAGA    9180
```

```
GCTTGACGGG GAAAGCCGGC GAACGTGGCG AGAAAGGAAG GGAAGAAAGC GAAAGGAGCG      9240

GGCGCTAGGG CGCTGGCAAG TGTAGCGGTC ACGCTGCGCG TAACCACCAC ACCCGCCGCG      9300

CTTAATGCGC CGCTACTGGG CGCGT                                            9325

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

TGCGGGTCAC CAATGGAGCC AGTAGATCCT AAT                                   33

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

ATATGGTGAC CCTTCCGTGG GCCCTGTCGG GTC                                   33

(2) INFORMATION FOR SEQ ID NO:5:

(i) SEQUENCE CHARACTERISTICS:
        (A) LENGTH: 6371 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA"

(xi) SEQUENCE DESCRIPTION: SEQ ID NO:5:

CCCATTCGCC ATTCAGGCTG CGCAACTGTT GGGAAGGGCG ATCGGTGCGG GCCTCTTCGC       60

TATTACGCCA GCTGGCGAAA GGGGGATGTG CTGCAAGGCG ATTAAGTTGG GTAACGCCAG      120

GGTTTTCCCA GTCACGACGT TGTAAAACGA CGGCCAGTGC CAAGCTATAT AAATTAACCC      180

TCACTAAAGG GAATAAGCTT GCATGCCTGC AGGTCGACTC TAGAGGATCC CCGGGTACCG      240

AGCTCGAATT CCACTGCCTT CCACCAAACT CTGCAGGATC CCAGAGTCAG GGTCTGTAT       300

CTTCCTGCTG GTGGCTCCAG TTCAGGAACA GTAAACCCTG CTCCGAATAT TGCCTCTCAC      360

ATCTCGTCAA TCTCCGCGAG GACTGGGGAC CCTGTGACGA ACATGGAGAA CATCACATCA      420

GGATTCCTAG GACCCCTGCT CGTGTTACAG GCGGGGTTTT TCTTGTTGAC AAGAATCCTC      480

ACAATACCGC AGAGTCTAGA CTCGTGGTGG ACTTCTCTCA ATTTTCTAGG GGGATCTCCC      540

GTGTGTCTTG GCCAAAATTC GCAGTCCCCA ACCTCCAATC ACTCACCAAC CTCCTGTCCT      600

CCAATTTGTC CTGGTTATCG CTGGATGTGT CTGCGGCGTT TTATCATATT CCTCTTCATC      660

CTGCTGCTAT GCCTCATCTT CTTATTGGTT CTTCTGGATT ATCAAGGTAT GTTGCCCGTT      720

TGTCCTCTAA TTCCAGGATC AACAACAACC AGTACGGGAC CATGCAAAAC CTGCACGACT      780

CCTGCTCAAG GCAACTCTAT GTTTCCCTCA TGTTGCTGTA CAAAACCTAC GGATGGAAAT      840
```

```
TGCACCTGTA TTCCCATCCC ATCGTCCTGG GCTTTCGCAA AATACCTATG GGAGTGGGCC      900
TCAGTCCGTT TCTCTTGGCT CAGTTTACTA GTGCCATTTG TTCAGTGGTT CGTAGGGCTT      960
TCCCCCACTG TTTGGCTTTC AGCTATATGG ATGATGTGGT ATTGGGGGCC AAGTCTGTAC     1020
AGCATCGTGA GTCCCTTTAT ACCGCTGTTA CCAATTTTCT TTTGTCTCTG GTATACATT      1080
TAAACCCTAA CAAAACAAAA AGATGGGGTT ATTCCCTAAA CTTCATGGGC TACATAATTG     1140
GAAGTTGGGG AACTTTGCCA CAGGATCATA TTGTACAAAA GATCAAACAC TGTTTTAGAA     1200
AACTTCCTGT TAACAGGCCT ATTGATTGGA AAGTATGTCA AAGAATTGTG GTCTTTTGG      1260
GCTTTGCTGC TCCATTTACA CAATGTGGAT ATCCTGCCTT AATGCCTTTG TATGCATGTA     1320
TACAAGCTAA ACAGGCTTTC ACTTTCTCGC CAACTTACAA GGCCTTTCTA AGTAAACAGT     1380
ACATGAACCT TTACCCCGTT GCTCGGCAAC GGCCTGGTCT GTGCCAAGTG TTTGCTGACG     1440
CAACCCCCAC TGGCTGGGGC TTGGCCATAG GCCATCAGCG CATGCGTGGA ACCTTTGTGG     1500
CTCCTCTGCC GATCCATACT GCGGAACTCC TAGCCGCTTG TTTTGCTCGC AGCCGGTCTG     1560
GAGCAAAGCT CATCGGAACT GACAATTCTG TCGTCCTCTC GCGGAAATAT ACATCGTTTC     1620
CATGGCTGCT AGGCTGTACT GCCAACTGGA TCCTTCGCGG GACGTCCTTT GTTTACGTCC     1680
CGTCGGCGCT GAATCCCGCG GACGACCCCT CTCGGGCCG CTTGGGACTC TCTCGTCCCC      1740
TTCTCCGTCT GCCGTTCCAG CCGACCACGG GGCGCACCTC TCTTTACGCG GTCTCCCCGT     1800
CTGTGCCTTC TCATCTGCCG GTCCGTGTGC ACTTCGCTTC ACCTCTGCAC GTTGCATGGA     1860
GACCACCGTG AACGCCCATC AGATCCTGCC CAAGGTCTTA CATAAGAGGA CTCTTGGACT     1920
CCCAGCAATG TCAACGACCG ACCTTGAGGC CTACTTCAAA GACTGTGTGT TAAGGACTG      1980
GGAGGAGCTG GGGGAGGAGA TTAGGTTAAA GGTCTTTGTA TTAGGAGGCT GTAGGCACAA     2040
ATTGGTCTGC GCACCAGCAC CATGCAACTT TTTCACCTCT GCCTAATCAT CTCTTGTACA     2100
TGTCCCACTG TTCAAGCCTC CAAGCTGTGC CTTGGGTGGC TTTGGGGCAT GGACATTGAC     2160
CCTTATAAAG AATTTGGAGC TACTGTGGAG TTACTCTCGT TTTTGCCTTC TGACTTCTTT     2220
CCTTCCGTCA GAGATCTCCT AGACACCGCC TCAGCTCTGT ATCGAGAAGC CTTAGAGTCT     2280
CCTGAGCATT CCTCACCTCA CCATACTGCA CTCAGGCAAG CCATTCTCTG CTGGGGGAA      2340
TTGATGACTC TAGCTACCTG GGTGGGTAAT AATTTGGAAG ATCCAGCATC TAGGGATCTT     2400
GTAGTAAATT ATGTTAATAC TAACGTGGGT TTAAAGATCA GGCAACTATT GTGGTTTCAT     2460
ATATCTTGCC TTACTTTTGG AAGAGAGACT GTACTTGAAT ATTTGGTCTC TTTCGGAGTG     2520
TGGATTCGCA CTCCTCCAGC CTATAGACCA CCAAATGCCC CTATCTTATC AACACTTCCG     2580
GAAACTACTG TTGTTAGACG ACGGGACCGA GGCAGGTCCC CTAGAAGAAG AACTCCCTCG     2640
CCTCGCAGAC GCAGATCTCC ATCGCCGCGT CGCAGAAGAT CTCAATCTCG GAATCTCAA      2700
TGTTAGTATT CCTTGGACTC ATAAGGTGGG AAACTTTACG GGGCTTTATT CCTCTACAGT     2760
ACCTATCTTT AATCCTGAAT GGCAAACTCC TTCCTTTCCT AAGATTCATT TACAAGAGGA     2820
CATTATTAAT AGGTGTCAAC AATTTGTGGG CCCTCTCACT GTAAATGAAA AGAGAAGATT     2880
GAAATTAATT ATGCCTGCTA GATTCTATCC TACCCACACT AAATATTTGC CCTTAGACAA     2940
AGGAATTAAA CCTTATTATC CAGATCAGGT AGTAATCAT  TACTTCCAAA CCAGACATTA     3000
TTTACATACT CTTTGGAAGG CTGGTATTCT ATATAAGCGG GAAACCACAC GTAGCGCATC     3060
ATTTTGCGGG TCACCAATGG AGCCAGTAGA TCCTAATCTA GAGCCCTGGA AGCATCCAGG     3120
AAGTCAGCCT AAAACTGCTT GTACCAATTG CTATTGTAAA AAGTGTTGCT TTCATTGCCA     3180
AGTTTGTTTC ATGACAAAAG CCTTAGGCAT CTCCTATGGC AGGAAGAAGC GGAGACAGCG     3240
```

```
ACGAAGAGCT CATCAGAACA GTCAGACTCA TCAAGCTTCT CTATCAAAGC AACCCACCTC    3300

CCAATCCCGA GGGGACCCGA CAGGGCCCAC GGAAGGGTCA CCATATTCTT GGGAACAAGA    3360

GCTACAGCAT GGGAGGTTGG TCATCAAAAC CTCGCAAAGG CATGGGGACG AATCTTTCTG    3420

TTCCCAATCC TCTGGGATTC TTTCCCGATC ATCAGTTGGA CCCTGCATTC GGAGCCAACT    3480

CAAACAATCC AGATTGGGAC TTCAACCCCG TCAAGGACGA CTGGCCAGCA GCCAACCAAG    3540

TAGGAGTGGG AGCATTCGGG CCAAGGCTCA CCCCTCCACA CGGCGGTATT TTGGGGTGGA    3600

GCCCTCAGGC TCAGGGCATA TTGACCACAG TGTCAACAAT TCCTCCTCCT GCCTCCACCA    3660

ATCGGCAGTC AGGAAGGCAG CCTACTCCCA TCTCTCCACC TCTAAGAGAC AGTCATCCTC    3720

AGGCCATGCA GTGGAATTCC CTATAGTGAG TCGTATTAAA TTCGTAATCA TGGTCATAGC    3780

TGTTTCCTGT GTGAAATTGT TATCCGCTCA CAATTCCACA ACATACGA GCCGGAAGCA    3840

TAAAGTGTAA AGCCTGGGGT GCCTAATGAG TGAGCTAACT CACATTAATT GCGTTGCGCT    3900

CACTGCCCGC TTTCCAGTCG GGAAACCTGT CGTGCCAGCT GCATTAATGA ATCGGCCAAC    3960

GCGCGGGGAG AGGCGGTTTG CGTATTGGGC GCTCTTCCGC TTCCTCGCTC ACTGACTCGC    4020

TGCGCTCGGT CGTTCGGCTG CGGCGAGCGG TATCAGCTCA CTCAAAGGCG GTAATACGGT    4080

TATCCACAGA ATCAGGGGAT AACGCAGGAA AGAACATGTG AGCAAAAGGC CAGCAAAAGG    4140

CCAGGAACCG TAAAAAGGCC GCGTTGCTGG CGTTTTTCCA TAGGCTCCGC CCCCCTGACG    4200

AGCATCACAA AAATCGACGC TCAAGTCAGA GGTGGCGAAA CCCGACAGGA CTATAAAGAT    4260

ACCAGGCGTT TCCCCCTGGA AGCTCCCTCG TGCGCTCTCC TGTTCCGACC CTGCCGCTTA    4320

CCGGATACCT GTCCGCCTTT CTCCCTTCGG GAAGCGTGGC GCTTTCTCAA TGCTCACGCT    4380

GTAGGTATCT CAGTTCGGTG TAGGTCGTTC GCTCCAAGCT GGGCTGTGTG CACGAACCCC    4440

CCGTTCAGCC CGACCGCTGC GCCTTATCCG GTAACTATCG TCTTGAGTCC AACCCGGTAA    4500

GACACGACTT ATCGCCACTG GCAGCAGCCA CTGGTAACAG GATTAGCAGA GCGAGGTATG    4560

TAGGCGGTGC TACAGAGTTC TTGAAGTGGT GGCCTAACTA CGGCTACACT AGAAGAACAG    4620

TATTTGGTAT CTGCGCTCTG CTGAAGCCAG TTACCTTCGG AAAAAGAGTT GGTAGCTCTT    4680

GATCCGGCAA ACAAACCACC GCTGGTAGCG GTGGTTTTTT TGTTTGCAAG CAGCAGATTA    4740

CGCGCAGAAA AAAAGGATCT CAAGAAGATC CTTTGATCTT TTCTACGGGG TCTGACGCTC    4800

AGTGGAACGA AAACTCACGT TAAGGGATTT TGGTCATGAG ATTATCAAAA AGGATCTTCA    4860

CCTAGATCCT TTTAAATTAA AAATGAAGTT TTAAATCAAT CTAAAGTATA TATGAGTAAA    4920

CTTGGTCTGA CAGTTACCAA TGCTTAATCA GTGAGGCACC TATCTCAGCG ATCTGTCTAT    4980

TTCGTTCATC CATAGTTGCC TGACTCCCCG TCGTGTAGAT AACTACGATA CGGGAGGGCT    5040

TACCATCTGG CCCCAGTGCT GCAATGATAC CGCGAGACCC ACGCTCACCG GCTCCAGATT    5100

TATCAGCAAT AAACCAGCCA GCCGGAAGGG CCGAGCGCAG AAGTGGTCCT GCAACTTTAT    5160

CCGCCTCCAT CCAGTCTATT AATTGTTGCC GGGAAGCTAG AGTAAGTAGT TCGCCAGTTA    5220

ATAGTTTGCG CAACGTTGTT GCCATTGCTA CAGGCATCGT GGTGTCACGC TCGTCGTTTG    5280

GTATGGCTTC ATTCAGCTCC GGTTCCCAAC GATCAAGGCG AGTTACATGA TCCCCCATGT    5340

TGTGCAAAAA AGCGGTTAGC TCCTTCGGTC CTCCGATCGT TGTCAGAAGT AAGTTGGCCG    5400

CAGTGTTATC ACTCATGGTT ATGGCAGCAC TGCATAATTC TCTTACTGTC ATGCCATCCG    5460

TAAGATGCTT TTCTGTGACT GGTGAGTACT CAACCAAGTC ATTCTGAGAA TAGTGTATGC    5520

GGCGACCGAG TTGCTCTTGC CCGGCGTCAA TACGGGATAA TACCGCGCCA CATAGCAGAA    5580

CTTTAAAAGT GCTCATCATT GGAAAACGTT CTTCGGGGCG AAAACTCTCA AGGATCTTAC    5640
```

-continued

```
CGCTGTTGAG ATCCAGTTCG ATGTAACCCA CTCGTGCACC CAACTGATCT TCAGCATCTT    5700

TTACTTTCAC CAGCGTTTCT GGGTGAGCAA AAACAGGAAG GCAAAATGCC GCAAAAAAGG    5760

GAATAAGGGC GACACGGAAA TGTTGAATAC TCATACTCTT CCTTTTTCAA TATTATTGAA    5820

GCATTTATCA GGGTTATTGT CTCATGAGCG GATACATATT TGAATGTATT TAGAAAAATA    5880

AACAAATAGG GGTTCCGCGC ACATTTCCCC GAAAAGTGCC ACCTGAAATT GTAAACGTTA    5940

ATGTTTTGTT AAATTTCGCG TTAAATATTT GTTAAATCAG CTTATTTTTT AACCAGTAAG    6000

CAGAAAATGA CAAAAATCCT TATAAATCAA AGAATAGAC CGAGTTAGTT GTGAGTGTTG     6060

TTCCAGTTTG GAACAAGAGT CCACTATTAA AGAACGTGGA CTCCAACGTA AAACCGTCTA    6120

TCAGGGCGAT GGCCCACTAC GTGAACCATC ACCCAAATCA AGTTTTTGGA GGTCGAGGTG    6180

CCGTAAAGCA CTAAATCGGA ACCCTAAAGG GAGCCCCCGA TTTAGAGCTT GACGGGGAAA    6240

GCCGGCGAAC GTGGCGAGAA AGGAAGGGAA GAAAGCGAAA GGAGCGGGCG CTAGGGCGCT    6300

GGCAAGTGTA GCGGTCACGC TGCGCGTAAC CACCACACCC GCCGCGCTTA ATGCGCCGCT    6360

ACTGGGCGCG T                                                        6371
```

(2) INFORMATION FOR SEQ ID NO:6:

(i) SEQUENCE CHARACTERISTICS:
        (A) LENGTH: 9859 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA"

(xi) SEQUENCE DESCRIPTION: SEQ ID NO:6:

```
CCCATTCGCC ATTCAGGCTG CGCAACTGTT GGGAAGGGCG ATCGGTGCGG GCCTCTTCGC     60

TATTACGCCA GCTGGCGAAA GGGGGATGTG CTGCAAGGCG ATTAAGTTGG GTAACGCCAG    120

GGTTTTCCCA GTCACGACGT TGTAAAACGA CGGCCAGTGC CAAGCTATAT AAATTAACCC    180

TCACTAAAGG GAATAAGCTT GCATGCCTGC AGGTCGACTC TAGAGGATCC CCGGGTACCG    240

AGCTCGAATT CCACTGCCTT CCACCAAACT CTGCAGGATC CCAGAGTCAG GGGTCTGTAT    300

CTTCCTGCTG GTGGCTCCAG TTCAGGAACA GTAAACCCTG CTCCGAATAT TGCCTCTCAC    360

ATCTCGTCAA TCTCCGCGAG GACTGGGGAC CCTGTGACGA ACATGGAGAA CATCACATCA    420

GGATTCCTAG GACCCCTGCT CGTGTTACAG GCGGGGTTTT TCTTGTTGAC AAGAATCCTC    480

ACAATACCGC AGAGTCTAGA CTCGTGGTGG ACTTCTCTCA ATTTTCTAGG GGGATCTCCC    540

GTGTGTCTTG GCCAAAATTC GCAGTCCCCA ACCTCCAATC ACTCACCAAC CTCCTGTCCT    600

CCAATTTGTC CTGGTTATCG CTGGATGTGT CTGCGGCGTT TTATCATATT CCTCTTCATC    660

CTGCTGCTAT GCCTCATCTT CTTATTGGTT CTTCTGGATT ATCAAGGTAT GTTGCCCGTT    720

TGTCCTCTAA TTCCAGGATC AACAACAACC AGTACGGGAC CATGCAAAAC CTGCACGACT    780

CCTGCTCAAG GCAACTCTAT GTTTCCCTCA TGTTGCTGTA CAAAACCTAC GGATGGAAAT    840

TGCACCTGTA TTCCCATCCC ATCGTCCTGG GCTTTCGCAA ATACCTATG GGAGTGGGCC     900

TCAGTCCGTT TCTCTTGGCT CAGTTTACTA GTGCCATTTG TTCAGTGGTT CGTAGGGCTT    960

TCCCCCACTG TTTGGCTTTC AGCTATATGG ATGATGTGGT ATTGGGGGCC AAGTCTGTAC   1020

AGCATCGTGA GTCCCTTTAT ACCGCTGTTA CCAATTTTCT TTTGTCTCTG GGTATACATT   1080

TAAACCCTAA CAAAACAAAA AGATGGGGTT ATTCCCTAAA CTTCATGGGC TACATAATTG   1140

GAAGTTGGGG AACTTTGCCA CAGGATCATA TTGTACAAAA GATCAAACAC TGTTTTAGAA   1200
```

-continued

```
AACTTCCTGT TAACAGGCCT ATTGATTGGA AAGTATGTCA AAGAATTGTG GGTCTTTTGG    1260

GCTTTGCTGC TCCATTTACA CAATGTGGAT ATCCTGCCTT AATGCCTTTG TATGCATGTA    1320

TACAAGCTAA ACAGGCTTTC ACTTTCTCGC CAACTTACAA GGCCTTTCTA AGTAAACAGT    1380

ACATGAACCT TTACCCCGTT GCTCGGCAAC GGCCTGGTCT GTGCCAAGTG TTTGCTGACG    1440

CAACCCCCAC TGGCTGGGGC TTGGCCATAG GCCATCAGCG CATGCGTGGA ACCTTTGTGG    1500

CTCCTCTGCC GATCCATACT GCGGAACTCC TAGCCGCTTG TTTTGCTCGC AGCCGGTCTG    1560

GAGCAAAGCT CATCGGAACT GACAATTCTG TCGTCCTCTC GCGGAAATAT ACATCGTTTC    1620

CATGGCTGCT AGGCTGTACT GCCAACTGGA TCCTTCGCGG GACGTCCTTT GTTTACGTCC    1680

CGTCGGCGCT GAATCCCGCG GACGACCCCT CTCGGGGCCG CTTGGGACTC TCTCGTCCCC    1740

TTCTCCGTCT GCCGTTCCAG CCGACCACGG GGCGCACCTC TCTTTACGCG GTCTCCCCGT    1800

CTGTGCCTTC TCATCTGCCG GTCCGTGTGC ACTTCGCTTC ACCTCTGCAC GTTGCATGGA    1860

GACCACCGTG AACGCCCATC AGATCCTGCC CAAGGTCTTA CATAAGAGGA CTCTTGGACT    1920

CCCAGCAATG TCAACGACCG ACCTTGAGGC CTACTTCAAA GACTGTGTGT TTAAGGACTG    1980

GGAGGAGCTG GGGGAGGAGA TTAGGTTAAA GGTCTTTGTA TTAGGAGGCT GTAGGCACAA    2040

ATTGGTCTGC GCACCAGCAC CATGCAACTT TTTCACCTCT GCCTAATCAT CTCTTGTACA    2100

TGTCCCACTG TTCAAGCCTC CAAGCTGTGC CTTGGGTGGC TTTGGGGCAT GGACATTGAC    2160

CCTTATAAAG AATTTGGAGC TACTGTGGAG TTACTCTCGT TTTTGCCTTC TGACTTCTTT    2220

CCTTCCGTCA GAGATCTCCT AGACACCGCC TCAGCTCTGT ATCGAGAAGC CTTAGAGTCT    2280

CCTGAGCATT CCTCACCTCA CCATACTGCA CTCAGGCAAG CCATTCTCTG CTGGGGGAA    2340

TTGATGACTC TAGCTACCTG GGTGGGTAAT AATTTGGAAG ATCCAGCATC TAGGGATCTT    2400

GTAGTAAATT ATGTTAATAC TAACGTGGGT TTAAAGATCA GGCAACTATT GTGGTTTCAT    2460

ATATCTTGCC TTACTTTTGG AAGAGAGACT GTACTTGAAT ATTTGGTCTC TTTCGGAGTG    2520

TGGATTCGCA CTCCTCCAGC CTATAGACCA CCAAATGCCC CTATCTTATC AACACTTCCG    2580

GAAACTACTG TTGTTAGACG ACGGGACCGA GGCAGGTCCC CTAGAAGAAG AACTCCCTCG    2640

CCTCGCAGAC GCAGATCTCC ATCGCCGCGT CGCAGAAGAT CTCAATCTCG GAATCTCAA    2700

TGTTAGTATT CCTTGGACTC ATAAGGTGGG AAACTTTACG GGGCTTTATT CCTCTACAGT    2760

ACCTATCTTT AATCCTGAAT GGCAAACTCC TTCCTTTCCT AAGATTCATT TACAAGAGGA    2820

CATTATTAAT AGGTGTCAAC AATTTGTGGG CCCTCTCACT GTAAATGAAA AGAGAAGATT    2880

GAAATTAATT ATGCCTGCTA GATTCTATCC TACCCACACT AAATATTTGC CCTTAGACAA    2940

AGGAATTAAA CCTTATTATC CAGATCAGGT AGTTAATCAT TACTTCCAAA CCAGACATTA    3000

TTTACATACT CTTTGGAAGG CTGGTATTCT ATATAAGCGG GAAACCACAC GTAGCGCATC    3060

ATTTTGCGGG TCACCAATGG AGCCAGTAGA TCCTAATCTA GAGCCCTGGA AGCATCCAGG    3120

AAGTCAGCCT AAAACTGCTT GTACCAATTG CTATTGTAAA AAGTGTTGCT TTCATTGCCA    3180

AGTTTGTTTC ATGACAAAAG CCTTAGGCAT CTCCTATGGC AGGAAGAAGC GGAGACAGCG    3240

ACGAAGAGCT CATCAGAACA GTCAGACTCA TCAAGCTTCT CTATCAAAGC AACCCACCTC    3300

CCAATCCCGA GGGGACCCGA CAGGGCCCAC GGAAGGGTCA CCATATTCTT GGGAACAAGA    3360

GCTACAGCAT GGGAGGTTGG TCATCAAAAC CTCGCAAAGG CATGGGACG AATCTTTCTG    3420

TTCCCAATCC TCTGGGATTC TTTCCCGATC ATCAGTTGGA CCCTGCATTC GGAGCCAACT    3480

CAAACAATCC AGATTGGGAC TTCAACCCCG TCAAGGACGA CTGGCCAGCA GCCAACCAAG    3540

TAGGAGTGGG AGCATTCGGG CCAAGGCTCA CCCCTCCACA CGGCGGTATT TTGGGGTGGA    3600
```

```
GCCCTCAGGC TCAGGGCATA TTGACCACAG TGTCAACAAT TCCTCCTCCT GCCTCCACCA     3660

ATCGGCAGTC AGGAAGGCAG CCTACTCCCA TCTCTCCACC TCTAAGAGAC AGTCATCCTC     3720

AGGCCATGCA GTGGAATTCC ACTGCCTTCC ACCAAACTCT GCAGGATCCC AGAGTCAGGG     3780

GTCTGTATCT TCCTGCTGGT GGCTCCAGTT CAGGAACAGT AAACCCTGCT CCGAATATTG     3840

CCTCTCACAT CTCGTCAATC TCCGCGAGGA CTGGGACCC TGTGACGAAC ATGGAGAACA      3900

TCACATCAGG ATTCCTAGGA CCCCTGCTCG TGTTACAGGC GGGGTTTTC TTGTTGACAA      3960

GAATCCTCAC AATACCGCAG AGTCTAGACT CGTGGTGGAC TTCTCTCAAT TTTCTAGGGG     4020

GATCTCCCGT GTGTCTTGGC CAAAATTCGC AGTCCCCAAC CTCCAATCAC TCACCAACCT     4080

CCTGTCCTCC AATTTGTCCT GGTTATCGCT GGATGTGTCT GCGGCGTTTT ATCATATTCC     4140

TCTTCATCCT GCTGCTATGC CTCATCTTCT TATTGGTTCT TCTGGATTAT CAAGGTATGT     4200

TGCCCGTTTG TCCTCTAATT CCAGGATCAA CAACAACCAG TACGGGACCA TGCAAAACCT     4260

GCACGACTCC TGCTCAAGGC AACTCTATGT TTCCCTCATG TTGCTGTACA AAACCTACGG     4320

ATGGAAATTG CACCTGTATT CCCATCCCAT CGTCCTGGGC TTTCGCAAAA TACCTATGGG     4380

AGTGGGCCTC AGTCCGTTTC TCTTGGCTCA GTTTACTAGT GCCATTTGTT CAGTGGTTCG     4440

TAGGGCTTTC CCCCACTGTT TGGCTTTCAG CTATATGGAT GATGTGGTAT TGGGGGCCAA     4500

GTCTGTACAG CATCGTGAGT CCCTTTATAC CGCTGTTACC AATTTTCTTT TGTCTCTGGG     4560

TATACATTTA AACCCTAACA AAACAAAAAG ATGGGGTTAT TCCCTAAACT TCATGGGCTA     4620

CATAATTGGA AGTTGGGGAA CTTTGCCACA GGATCATATT GTACAAAAGA TCAAACACTG     4680

TTTTAGAAAA CTTCCTGTTA ACAGGCCTAT TGATTGGAAA GTATGTCAAA GAATTGTGGG     4740

TCTTTTGGGC TTTGCTGCTC CATTTACACA ATGTGGATAT CCTGCCTTAA TGCCTTTGTA     4800

TGCATGTATA CAAGCTAAAC AGGCTTTCAC TTTCTCGCCA ACTTACAAGG CCTTTCTAAG     4860

TAAACAGTAC ATGAACCTTT ACCCCGTTGC TCGGCAACGG CCTGGTCTGT GCCAAGTGTT     4920

TGCTGACGCA ACCCCACTG GCTGGGGCTT GGCCATAGGC CATCAGCGCA TGCGTGGAAC      4980

CTTTGTGGCT CCTCTGCCGA TCCATACTGC GGAACTCCTA GCCGCTTGTT TTGCTCGCAG     5040

CCGGTCTGGA GCAAAGCTCA TCGGAACTGA CAATTCTGTC GTCCTCTCGC GGAAATATAC     5100

ATCGTTTCCA TGGCTGCTAG GCTGTACTGC CAACTGGATC CTTCGCGGGA CGTCCTTTGT     5160

TTACGTCCCG TCGGCGCTGA ATCCCGCGGA CGACCCCTCT CGGGGCCGCT TGGGACTCTC     5220

TCGTCCCCTT CTCCGTCTGC CGTTCCAGCC GACCACGGGG CGCACCTCTC TTTACGCGGT     5280

CTCCCCGTCT GTGCCTTCTC ATCTGCCGGT CCGTGTGCAC TTCGCTTCAC CTCTGCACGT     5340

TGCATGGAGA CCACCGTGAA CGCCCATCAG ATCCTGCCCA AGGTCTTACA TAAGAGGACT     5400

CTTGGACTCC CAGCAATGTC AACGACCGAC CTTGAGGCCT ACTTCAAAGA CTGTGTGTTT     5460

AAGGACTGGG AGGAGCTGGG GGAGGAGATT AGGTTAAAGG TCTTTGTATT AGGAGGCTGT     5520

AGGCACAAAT TGGTCTGCGC ACCAGCACCA TGCAACTTTT TCACCTCTGC CTAATCATCT     5580

CTTGTACATG TCCCACTGTT CAAGCCTCCA AGCTGTGCCT TGGGTGGCTT TGGGGCATGG     5640

ACATTGACCC TTATAAAGAA TTTGGAGCTA CTGTGGAGTT ACTCTCGTTT TTGCCTTCTG     5700

ACTTCTTTCC TTCCGTCAGA GATCTCCTAG ACACCGCCTC AGCTCTGTAT CGAGAAGCCT     5760

TAGAGTCTCC TGAGCATTCC TCACCTCACC ATACTGCACT CAGGCAAGCC ATTCTCTGCT     5820

GGGGGGAATT GATGACTCTA GCTACCTGGG TGGGTAATAA TTTGGAAGAT CCAGCATCTA     5880

GGGATCTTGT AGTAAATTAT GTTAATACTA ACGTGGGTTT AAAGATCAGG CAACTATTGT     5940

GGTTTCATAT ATCTTGCCTT ACTTTTGGAA GAGAGACTGT ACTTGAATAT TTGGTCTCTT     6000
```

```
TCGGAGTGTG GATTCGCACT CCTCCAGCCT ATAGACCACC AAATGCCCCT ATCTTATCAA    6060

CACTTCCGGA AACTACTGTT GTTAGACGAC GGGACCGAGG CAGGTCCCCT AGAAGAAGAA    6120

CTCCCTCGCC TCGCAGACGC AGATCTCCAT CGCCGCGTCG CAGAAGATCT CAATCTCGGG    6180

AATCTCAATG TTAGTATTCC TTGGACTCAT AAGGTGGGAA ACTTTACGGG GCTTTATTCC    6240

TCTACAGTAC CTATCTTTAA TCCTGAATGG CAAACTCCTT CCTTTCCTAA GATTCATTTA    6300

CAAGAGGACA TTATTAATAG GTGTCAACAA TTTGTGGGCC CTCTCACTGT AAATGAAAAG    6360

AGAAGATTGA AATTAATTAT GCCTGCTAGA TTCTATCCTA CCCACACTAA ATATTTGCCC    6420

TTAGACAAAG GAATTAAACC TTATTATCCA GATCAGGTAG TTAATCATTA CTTCCAAACC    6480

AGACATTATT TACATACTCT TTGGAAGGCT GGTATTCTAT ATAAGCGGGA AACCACACGT    6540

AGCGCATCAT TTTGCGGGTC ACCAATGGAG CCAGTAGATC CTAATCTAGA GCCCTGGAAG    6600

CATCCAGGAA GTCAGCCTAA AACTGCTTGT ACCAATTGCT ATTGTAAAAA GTGTTGCTTT    6660

CATTGCCAAG TTTGTTTCAT GACAAAAGCC TTAGGCATCT CCTATGGCAG GAAGAAGCGG    6720

AGACAGCGAC GAAGAGCTCA TCAGAACAGT CAGACTCATC AAGCTTCTCT ATCAAAGCAA    6780

CCCACCTCCC AATCCCGAGG GGACCCGACA GGGCCCACGG AAGGGTCACC ATATTCTTGG    6840

GAACAAGAGC TACAGCATGG GAGGTTGGTC ATCAAAACCT CGCAAAGGCA TGGGGACGAA    6900

TCTTTCTGTT CCCAATCCTC TGGGATTCTT TCCCGATCAT CAGTTGGACC CTGCATTCGG    6960

AGCCAACTCA AACAATCCAG ATTGGGACTT CAACCCCGTC AAGGACGACT GGCCAGCAGC    7020

CAACCAAGTA GGAGTGGGAG CATTCGGGCC AAGGCTCACC CCTCCACACG GCGGTATTTT    7080

GGGGTGGAGC CCTCAGGCTC AGGGCATATT GACCACAGTG TCAACAATTC CTCCTCCTGC    7140

CTCCACCAAT CGGCAGTCAG GAAGGCAGCC TACTCCCATC TCTCCACCTC TAAGAGACAG    7200

TCATCCTCAG GCCATGCAGT GGAATTCCCT ATAGTGAGTC GTATTAAATT CGTAATCATG    7260

GTCATAGCTG TTTCCTGTGT GAAATTGTTA TCCGCTCACA ATTCCACACA ACATACGAGC    7320

CGGAAGCATA AAGTGTAAAG CCTGGGGTGC CTAATGAGTG AGCTAACTCA CATTAATTGC    7380

GTTGCGCTCA CTGCCCGCTT TCCAGTCGGG AAACCTGTCG TGCCAGCTGC ATTAATGAAT    7440

CGGCCAACGC GCGGGGAGAG GCGGTTTGCG TATTGGGCGC TCTTCCGCTT CCTCGCTCAC    7500

TGACTCGCTG CGCTCGGTCG TTCGGCTGCG GCGAGCGGTA TCAGCTCACT CAAAGGCGGT    7560

AATACGGTTA TCCACAGAAT CAGGGGATAA CGCAGGAAAG AACATGTGAG CAAAAGGCCA    7620

GCAAAAGGCC AGGAACCGTA AAAAGGCCGC GTTGCTGGCG TTTTTCCATA GGCTCCGCCC    7680

CCCTGACGAG CATCACAAAA ATCGACGCTC AAGTCAGAGG TGGCGAAACC CGACAGGACT    7740

ATAAAGATAC CAGGCGTTTC CCCCTGGAAG CTCCCTCGTG CGCTCTCCTG TTCCGACCCT    7800

GCCGCTTACC GGATACCTGT CCGCCTTTCT CCCTTCGGGA AGCGTGGCGC TTTCTCAATG    7860

CTCACGCTGT AGGTATCTCA GTTCGGTGTA GGTCGTTCGC TCCAAGCTGG GCTGTGTGCA    7920

CGAACCCCCC GTTCAGCCCG ACCGCTGCGC CTTATCCGGT AACTATCGTC TTGAGTCCAA    7980

CCCGGTAAGA CACGACTTAT CGCCACTGGC AGCAGCCACT GGTAACAGGA TTAGCAGAGC    8040

GAGGTATGTA GGCGGTGCTA CAGAGTTCTT GAAGTGGTGG CCTAACTACG GCTACACTAG    8100

AAGAACAGTA TTTGGTATCT GCGCTCTGCT GAAGCCAGTT ACCTTCGGAA AAAGAGTTGG    8160

TAGCTCTTGA TCCGGCAAAC AAACCACCGC TGGTAGCGGT GGTTTTTTTG TTTGCAAGCA    8220

GCAGATTACG CGCAGAAAAA AAGGATCTCA AGAAGATCCT TTGATCTTTT CTACGGGGTC    8280

TGACGCTCAG TGGAACGAAA ACTCACGTTA AGGGATTTTG GTCATGAGAT TATCAAAAAG    8340

GATCTTCACC TAGATCCTTT TAAATTAAAA ATGAAGTTTT AAATCAATCT AAAGTATATA    8400
```

```
TGAGTAAACT TGGTCTGACA GTTACCAATG CTTAATCAGT GAGGCACCTA TCTCAGCGAT    8460

CTGTCTATTT CGTTCATCCA TAGTTGCCTG ACTCCCCGTC GTGTAGATAA CTACGATACG    8520

GGAGGGCTTA CCATCTGGCC CCAGTGCTGC AATGATACCG CGAGACCCAC GCTCACCGGC    8580

TCCAGATTTA TCAGCAATAA ACCAGCCAGC CGGAAGGGCC GAGCGCAGAA GTGGTCCTGC    8640

AACTTTATCC GCCTCCATCC AGTCTATTAA TTGTTGCCGG GAAGCTAGAG TAAGTAGTTC    8700

GCCAGTTAAT AGTTTGCGCA ACGTTGTTGC CATTGCTACA GGCATCGTGG TGTCACGCTC    8760

GTCGTTTGGT ATGGCTTCAT TCAGCTCCGG TTCCCAACGA TCAAGGCGAG TTACATGATC    8820

CCCCATGTTG TGCAAAAAAG CGGTTAGCTC CTTCGGTCCT CCGATCGTTG TCAGAAGTAA    8880

GTTGGCCGCA GTGTTATCAC TCATGGTTAT GGCAGCACTG CATAATTCTC TTACTGTCAT    8940

GCCATCCGTA AGATGCTTTT CTGTGACTGG TGAGTACTCA ACCAAGTCAT TCTGAGAATA    9000

GTGTATGCGG CGACCGAGTT GCTCTTGCCC GGCGTCAATA CGGGATAATA CCGCGCCACA    9060

TAGCAGAACT TTAAAAGTGC TCATCATTGG AAAACGTTCT TCGGGGCGAA AACTCTCAAG    9120

GATCTTACCG CTGTTGAGAT CCAGTTCGAT GTAACCCACT CGTGCACCCA ACTGATCTTC    9180

AGCATCTTTT ACTTTCACCA GCGTTTCTGG GTGAGCAAAA ACAGGAAGGC AAAATGCCGC    9240

AAAAAAGGGA ATAAGGGCGA CACGGAAATG TTGAATACTC ATACTCTTCC TTTTTCAATA    9300

TTATTGAAGC ATTTATCAGG GTTATTGTCT CATGAGCGGA TACATATTTG AATGTATTTA    9360

GAAAAATAAA CAAATAGGGG TTCCGCGCAC ATTTCCCCGA AAAGTGCCAC CTGAAATTGT    9420

AAACGTTAAT GTTTTGTTAA ATTTCGCGTT AAATATTTGT TAAATCAGCT TATTTTTTAA    9480

CCAGTAAGCA GAAAATGACA AAAATCCTTA TAAATCAAAA GAATAGACCG AGTTAGTTGT    9540

GAGTGTTGTT CCAGTTTGGA ACAAGAGTCC ACTATTAAAG AACGTGGACT CCAACGTAAA    9600

ACCGTCTATC AGGGCGATGG CCCACTACGT GAACCATCAC CCAAATCAAG TTTTTGGAGG    9660

TCGAGGTGCC GTAAAGCACT AAATCGGAAC CCTAAAGGGA GCCCCCGATT TAGAGCTTGA    9720

CGGGGAAAGC CGGCGAACGT GGCGAGAAAG GAAGGGAAGA AAGCGAAAGG AGCGGGCGCT    9780

AGGGCGCTGG CAAGTGTAGC GGTCACGCTG CGCGTAACCA CCACACCCGC CGCGCTTAAT    9840

GCGCCGCTAC TGGGCGCGT                                                9859
```

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:7:

```
AAGGATCCTC GAGCCACCAT GGAGCCAGTA GATCCT                               36
```

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

```
CAAGATCTGC ATGCTAATCG AACGGATCTG TC                                    32

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:9:

TTACTAGTGC CATTTGTTCA GTGGTTCG                                         28

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:10:

GTGCACACGG ACCGGCAGAT G                                                21

(2) INFORMATION FOR SEQ ID NO:11:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:11:

ATACATCGTT TCCCTGGCTG CTAGGCTGTA CTGCTAACTG GATCCTTC                   48

(2) INFORMATION FOR SEQ ID NO:12:

(i) SEQUENCE CHARACTERISTICS:
        (A) LENGTH: 6371 base pairs
        (B) TYPE: nucleic acid
        (C) STRANDEDNESS: double
        (D) TOPOLOGY: circular (ii) MOLECULE TYPE: other nucleic acid
         (A) DESCRIPTION: /desc = "DNA"

(xi) SEQUENCE DESCRIPTION: SEQ ID NO:12:

CCCATTCGCC ATTCAGGCTG CGCAACTGTT GGGAAGGGCG ATCGGTGCGG GCCTCTTCGC      60

TATTACGCCA GCTGGCGAAA GGGGGATGTG CTGCAAGGCG ATTAAGTTGG GTAACGCCAG     120

GGTTTTCCCA GTCACGACGT TGTAAAACGA CGGCCAGTGC CAAGCTATAT AAATTAACCC    180

TCACTAAAGG GAATAAGCTT GCATGCCTGC AGGTCGACTC TAGAGGATCC CCGGGTACCG    240

AGCTCGAATT CCACTGCCTT CCACCAAACT CTGCAGGATC CAGAGTCAG GGGTCTGTAT     300

CTTCCTGCTG GTGGCTCCAG TTCAGGAACA GTAAACCCTG CTCCGAATAT TGCCTCTCAC    360

ATCTCGTCAA TCTCCGCGAG GACTGGGGAC CCTGTGACGA ACATGGAGAA CATCACATCA    420

GGATTCCTAG GACCCCTGCT CGTGTTACAG GCGGGGTTTT TCTTGTTGAC AAGAATCCTC    480
```

-continued

```
ACAATACCGC AGAGTCTAGA CTCGTGGTGG ACTTCTCTCA ATTTTCTAGG GGGATCTCCC      540

GTGTGTCTTG GCCAAAATTC GCAGTCCCCA ACCTCCAATC ACTCACCAAC CTCCTGTCCT      600

CCAATTTGTC CTGGTTATCG CTGGATGTGT CTGCGGCGTT TTATCATATT CCTCTTCATC      660

CTGCTGCTAT GCCTCATCTT CTTATTGGTT CTTCTGGATT ATCAAGGTAT GTTGCCCGTT      720

TGTCCTCTAA TTCCAGGATC AACAACAACC AGTACGGGAC CATGCAAAAC CTGCACGACT      780

CCTGCTCAAG GCAACTCTAT GTTTCCCTCA TGTTGCTGTA CAAAACCTAC GGATGGAAAT      840

TGCACCTGTA TTCCCATCCC ATCGTCCTGG GCTTTCGCAA ATACCTATG GGAGTGGGCC       900

TCAGTCCGTT TCTCTTGGCT CAGTTTACTA GTGCCATTTG TTCAGTGGTT CGTAGGGCTT      960

TCCCCCACTG TTTGGCTTTC AGCTATATGG ATGATGTGGT ATTGGGGGCC AAGTCTGTAC     1020

AGCATCGTGA GTCCCTTTAT ACCGCTGTTA CCAATTTTCT TTTGTCTCTG GTATACATT      1080

TAAACCCTAA CAAAACAAAA AGATGGGGTT ATTCCCTAAA CTTCATGGGC TACATAATTG     1140

GAAGTTGGGG AACTTTGCCA CAGGATCATA TTGTACAAAA GATCAAACAC TGTTTTAGAA     1200

AACTTCCTGT TAACAGGCCT ATTGATTGGA AAGTATGTCA AAGAATTGTG GGTCTTTTGG     1260

GCTTTGCTGC TCCATTTACA CAATGTGGAT ATCCTGCCTT AATGCCTTTG TATGCATGTA     1320

TACAAGCTAA ACAGGCTTTC ACTTTCTCGC CAACTTACAA GGCCTTTCTA AGTAAACAGT     1380

ACATGAACCT TTACCCCGTT GCTCGGCAAC GGCCTGGTCT GTGCCAAGTG TTTGCTGACG     1440

CAACCCCCAC TGGCTGGGGC TTGGCCATAG GCCATCAGCG CATGCGTGGA ACCTTTGTGG     1500

CTCCTCTGCC GATCCATACT GCGGAACTCC TAGCCGCTTG TTTTGCTCGC AGCCGGTCTG     1560

GAGCAAAGCT CATCGGAACT GACAATTCTG TCGTCCTCTC GCGGAAATAT ACATCGTTTC     1620

CTTGGCTGCT AGGCTGTACT GCTAACTGGA TCCTTCGCGG GACGTCCTTT GTTTACGTCC     1680

CGTCGGCGCT GAATCCCGCG GACGACCCCT CTCGGGCCG CTTGGGACTC TCTCGTCCCC      1740

TTCTCCGTCT GCCGTTCCAG CCGACCACGG GGCGCACCTC TCTTTACGCG GTCTCCCGT     1800

CTGTGCCTTC TCATCTGCCG GTCCGTGTGC ACTTCGCTTC ACCTCTGCAC GTTGCATGGA     1860

GACCACCGTG AACGCCCATC AGATCCTGCC CAAGGTCTTA CATAAGAGGA CTCTTGGACT     1920

CCCAGCAATG TCAACGACCG ACCTTGAGGC CTACTTCAAA GACTGTGTGT TTAAGGACTG     1980

GGAGGAGCTG GGGGAGGAGA TTAGGTTAAA GGTCTTTGTA TTAGGAGGCT GTAGGCACAA     2040

ATTGGTCTGC GCACCAGCAC CATGCAACTT TTTCACCTCT GCCTAATCAT CTCTTGTACA     2100

TGTCCCACTG TTCAAGCCTC CAAGCTGTGC CTTGGGTGGC TTTGGGGCAT GGACATTGAC     2160

CCTTATAAAG AATTTGGAGC TACTGTGGAG TTACTCTCGT TTTTGCCTTC TGACTTCTTT     2220

CCTTCCGTCA GAGATCTCCT AGACACCGCC TCAGCTCTGT ATCGAGAAGC CTTAGAGTCT     2280

CCTGAGCATT CCTCACCTCA CCATACTGCA CTCAGGCAAG CCATTCTCTG CTGGGGGGAA     2340

TTGATGACTC TAGCTACCTG GGTGGGTAAT AATTTGGAAG ATCCAGCATC TAGGGATCTT     2400

GTAGTAAATT ATGTTAATAC TAACGTGGGT TTAAAGATCA GGCAACTATT GTGGTTTCAT     2460

ATATCTTGCC TTACTTTTGG AAGAGAGACT GTACTTGAAT ATTTGGTCTC TTTCGGAGTG     2520

TGGATTCGCA CTCCTCCAGC CTATAGACCA CCAAATGCCC CTATCTTATC AACACTTCCG     2580

GAAACTACTG TTGTTAGACG ACGGGACCGA GGCAGGTCCC CTAGAAGAAG AACTCCCTCG     2640

CCTCGCAGAC GCAGATCTCC ATCGCCGCGT CGCAGAAGAT CTCAATCTCG GAATCTCAA     2700

TGTTAGTATT CCTTGGACTC ATAAGGTGGG AAACTTTACG GGGCTTTATT CCTCTACAGT     2760

ACCTATCTTT AATCCTGAAT GGCAAACTCC TTCCTTTCCT AAGATTCATT TACAAGAGGA     2820

CATTATTAAT AGGTGTCAAC AATTTGTGGG CCCTCTCACT GTAAATGAAA AGAGAAGATT     2880
```

-continued

```
GAAATTAATT ATGCCTGCTA GATTCTATCC TACCCACACT AAATATTTGC CCTTAGACAA    2940

AGGAATTAAA CCTTATTATC CAGATCAGGT AGTTAATCAT TACTTCCAAA CCAGACATTA    3000

TTTACATACT CTTTGGAAGG CTGGTATTCT ATATAAGCGG GAAACCACAC GTAGCGCATC    3060

ATTTTGCGGG TCACCAATGG AGCCAGTAGA TCCTAATCTA GAGCCCTGGA AGCATCCAGG    3120

AAGTCAGCCT AAAACTGCTT GTACCAATTG CTATTGTAAA AAGTGTTGCT TTCATTGCCA    3180

AGTTTGTTTC ATGACAAAAG CCTTAGGCAT CTCCTATGGC AGGAAGAAGC GGAGACAGCG    3240

ACGAAGAGCT CATCAGAACA GTCAGACTCA TCAAGCTTCT CTATCAAAGC AACCCACCTC    3300

CCAATCCCGA GGGGACCCGA CAGGGCCCAC GGAAGGGTCA CCATATTCTT GGGAACAAGA    3360

GCTACAGCAT GGGAGGTTGG TCATCAAAAC CTCGCAAAGG CATGGGGACG AATCTTTCTG    3420

TTCCCAATCC TCTGGGATTC TTTCCCGATC ATCAGTTGGA CCCTGCATTC GGAGCCAACT    3480

CAAACAATCC AGATTGGGAC TTCAACCCCG TCAAGGACGA CTGGCCAGCA GCCAACCAAG    3540

TAGGAGTGGG AGCATTCGGG CCAAGGCTCA CCCCTCCACA CGGCGGTATT TTGGGGTGGA    3600

GCCCTCAGGC TCAGGCATA TTGACCACAG TGTCAACAAT TCCTCCTCCT GCCTCCACCA    3660

ATCGGCAGTC AGGAAGGCAG CCTACTCCCA TCTCTCCACC TCTAAGAGAC AGTCATCCTC    3720

AGGCCATGCA GTGGAATTCC CTATAGTGAG TCGTATTAAA TTCGTAATCA TGGTCATAGC    3780

TGTTTCCTGT GTGAAATTGT TATCCGCTCA CAATTCCACA ACATACGA GCCGGAAGCA    3840

TAAAGTGTAA AGCCTGGGGT GCCTAATGAG TGAGCTAACT CACATTAATT GCGTTGCGCT    3900

CACTGCCCGC TTTCCAGTCG GGAAACCTGT CGTGCCAGCT GCATTAATGA ATCGGCCAAC    3960

GCGCGGGGAG AGGCGGTTTG CGTATTGGGC GCTCTTCCGC TTCCTCGCTC ACTGACTCGC    4020

TGCGCTCGGT CGTTCGGCTG CGGCGAGCGG TATCAGCTCA CTCAAAGGCG GTAATACGGT    4080

TATCCACAGA ATCAGGGGAT AACGCAGGAA AGAACATGTG AGCAAAAGGC CAGCAAAAGG    4140

CCAGGAACCG TAAAAAGGCC GCGTTGCTGG CGTTTTTCCA TAGGCTCCGC CCCCCTGACG    4200

AGCATCACAA AAATCGACGC TCAAGTCAGA GGTGGCGAAA CCCGACAGGA CTATAAAGAT    4260

ACCAGGCGTT TCCCCCTGGA AGCTCCCTCG TGCGCTCTCC TGTTCCGACC CTGCCGCTTA    4320

CCGGATACCT GTCCGCCTTT CTCCCTTCGG GAAGCGTGGC GCTTTCTCAA TGCTCACGCT    4380

GTAGGTATCT CAGTTCGGTG TAGGTCGTTC GCTCCAAGCT GGGCTGTGTG CACGAACCCC    4440

CCGTTCAGCC CGACCGCTGC GCCTTATCCG GTAACTATCG TCTTGAGTCC AACCCGGTAA    4500

GACACGACTT ATCGCCACTG GCAGCAGCCA CTGGTAACAG GATTAGCAGA GCGAGGTATG    4560

TAGGCGGTGC TACAGAGTTC TTGAAGTGGT GGCCTAACTA CGGCTACACT AGAAGAACAG    4620

TATTTGGTAT CTGCGCTCTG CTGAAGCCAG TTACCTTCGG AAAAAGAGTT GGTAGCTCTT    4680

GATCCGGCAA ACAAACCACC GCTGGTAGCG GTGGTTTTTT TGTTTGCAAG CAGCAGATTA    4740

CGCGCAGAAA AAAAGGATCT CAAGAAGATC CTTTGATCTT TTCTACGGGG TCTGACGCTC    4800

AGTGGAACGA AAACTCACGT TAAGGGATTT TGGTCATGAG ATTATCAAAA AGGATCTTCA    4860

CCTAGATCCT TTTAAATTAA AAATGAAGTT TTAAATCAAT CTAAAGTATA TATGAGTAAA    4920

CTTGGTCTGA CAGTTACCAA TGCTTAATCA GTGAGGCACC TATCTCAGCG ATCTGTCTAT    4980

TTCGTTCATC CATAGTTGCC TGACTCCCCG TCGTGTAGAT AACTACGATA CGGGAGGGCT    5040

TACCATCTGG CCCCAGTGCT GCAATGATAC CGCGAGACCC ACGCTCACCG GCTCCAGATT    5100

TATCAGCAAT AAACCAGCCA GCCGGAAGGG CCGAGCGCAG AAGTGGTCCT GCAACTTTAT    5160

CCGCCTCCAT CCAGTCTATT AATTGTTGCC GGGAAGCTAG AGTAAGTAGT TCGCCAGTTA    5220

ATAGTTTGCG CAACGTTGTT GCCATTGCTA CAGGCATCGT GGTGTCACGC TCGTCGTTTG    5280
```

-continued

| | |
|---|---|
| GTATGGCTTC ATTCAGCTCC GGTTCCCAAC GATCAAGGCG AGTTACATGA TCCCCCATGT | 5340 |
| TGTGCAAAAA AGCGGTTAGC TCCTTCGGTC CTCCGATCGT TGTCAGAAGT AAGTTGGCCG | 5400 |
| CAGTGTTATC ACTCATGGTT ATGGCAGCAC TGCATAATTC TCTTACTGTC ATGCCATCCG | 5460 |
| TAAGATGCTT TTCTGTGACT GGTGAGTACT CAACCAAGTC ATTCTGAGAA TAGTGTATGC | 5520 |
| GGCGACCGAG TTGCTCTTGC CCGGCGTCAA TACGGGATAA TACCGCGCCA CATAGCAGAA | 5580 |
| CTTTAAAAGT GCTCATCATT GGAAAACGTT CTTCGGGGCG AAAACTCTCA AGGATCTTAC | 5640 |
| CGCTGTTGAG ATCCAGTTCG ATGTAACCCA CTCGTGCACC CAACTGATCT TCAGCATCTT | 5700 |
| TTACTTTCAC CAGCGTTTCT GGGTGAGCAA AAACAGGAAG GCAAAATGCC GCAAAAAAGG | 5760 |
| GAATAAGGGC GACACGGAAA TGTTGAATAC TCATACTCTT CCTTTTTCAA TATTATTGAA | 5820 |
| GCATTTATCA GGGTTATTGT CTCATGAGCG GATACATATT TGAATGTATT TAGAAAAATA | 5880 |
| AACAAATAGG GGTTCCGCGC ACATTTCCCC GAAAAGTGCC ACCTGAAATT GTAAACGTTA | 5940 |
| ATGTTTTGTT AAATTTCGCG TTAAATATTT GTTAAATCAG CTTATTTTTT AACCAGTAAG | 6000 |
| CAGAAAATGA CAAAAATCCT TATAAATCAA AAGAATAGAC CGAGTTAGTT GTGAGTGTTG | 6060 |
| TTCCAGTTTG GAACAAGAGT CCACTATTAA AGAACGTGGA CTCCAACGTA AAACCGTCTA | 6120 |
| TCAGGGCGAT GGCCCACTAC GTGAACCATC ACCCAAATCA AGTTTTTGGA GGTCGAGGTG | 6180 |
| CCGTAAAGCA CTAAATCGGA ACCCTAAAGG GAGCCCCCGA TTTAGAGCTT GACGGGGAAA | 6240 |
| GCCGGCGAAC GTGGCGAGAA AGGAAGGGAA GAAAGCGAAA GGAGCGGGCG CTAGGGCGCT | 6300 |
| GGCAAGTGTA GCGGTCACGC TGCGCGTAAC CACCACACCC GCCGCGCTTA ATGCGCCGCT | 6360 |
| ACTGGGCGCG T | 6371 |

(2) INFORMATION FOR SEQ ID NO:13:

(i) SEQUENCE CHARACTERISTICS:
        (A) LENGTH: 7463 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA"

(xi) SEQUENCE DESCRIPTION: SEQ ID NO:13:

| | |
|---|---|
| GGCGTAATCT GCTGCTTGCA AACAAAAAAA CCACCGCTAC CAGCGGTGGT TTGTTTGCCG | 60 |
| GATCAAGAGC TACCAACTCT TTTTCCGAAG GTAACTGGCT TCAGCAGAGC GCAGATACCA | 120 |
| AATACTGTCC TTCTAGTGTA GCCGTAGTTA GGCCACCACT TCAAGAACTC TGTAGCACCG | 180 |
| CCTACATACC TCGCTCTGCT AATCCTGTTA CCAGTGGCTG CTGCCAGTGG CGATAAGTCG | 240 |
| TGTCTTACCG GGTTGGACTC AAGACGATAG TTACCGGATA AGGCGCAGCG GTCGGGCTGA | 300 |
| ACGGGGGGTT CGTGCACACA GCCCAGCTTG GAGCGAACGA CCTACACCGA ACTGAGATAC | 360 |
| CTACAGCGTG AGCATTGAGA AAGCGCCACG CTTCCCGAAG GGAGAAAGGC GGACAGGTAT | 420 |
| CCGGTAAGCG GCAGGGTCGG AACAGGAGAG CGCACGAGGG AGCTTCCAGG GGGAAACGCC | 480 |
| TGGTATCTTT ATAGTCCTGT CGGGTTTCGC CACCTCTGAC TTGAGCGTCG ATTTTTGTGA | 540 |
| TGCTCGTCAG GGGGGCGGAG CCTATGGAAA AACGCCAGCA ACGCAAGCTA GCTTCTAGCT | 600 |
| AGAAATTGTA AACGTTAATA TTTTGTTAAA ATTCGCGTTA AATTTTGTT AAATCAGCTC | 660 |
| ATTTTTTAAC CAATAGGCCG AAATCGGCAA AATCCCTTAT AAATCAAAAG AATAGCCCGA | 720 |
| GATAGGGTTG AGTGTTGTTC CAGTTTGGAA CAAGAGTCCA CTATTAAAGA ACGTGGACTC | 780 |
| CAACGTCAAA GGGCGAAAAA CCGTCTATCA GGGCGATGGC CGCCCACTAC GTGAACCATC | 840 |

```
ACCCAAATCA AGTTTTTTGG GGTCGAGGTG CCGTAAAGCA CTAAATCGGA ACCCTAAAGG    900
GAGCCCCCGA TTTAGAGCTT GACGGGGAAA GCCGGCGAAC GTGGCGAGAA AGGAAGGGAA    960
GAAAGCGAAA GGAGCGGGCG CTAGGGCGCT GGCAAGTGTA GCGGTCACGC TGCGCGTAAC   1020
CACCACACCC GCCGCGCTTA ATGCGCCGCT ACAGGGCGCG TACTATGGTT GCTTTGACGA   1080
GACCGTATAA CGTGCTTTCC TCGTTGGAAT CAGAGCGGGA GCTAAACAGG AGGCCGATTA   1140
AAGGGATTTT AGACAGGAAC GGTACGCCAG CTGGATTACC AAAGGGCCTC GTGATACGCC   1200
TATTTTTATA GGTTAATGTC ATGATAATAA TGGTTTCTTA GACGTCAGGT GGCACTTTTC   1260
GGGGAAATGT GCGCGGAACC CCTATTTGTT TATTTTTCTA AATACATTCA AATATGTATC   1320
CGCTCATGAG ACAATAACCC TGATAAATGC TTCAATAATA TTGAAAAAGG AAGAGTATGA   1380
GTATTCAACA TTTCCGTGTC GCCCTTATTC CCTTTTTTGC GGCATTTTGC CTTCCTGTTT   1440
TTGCTCACCC AGAAACGCTG GTGAAAGTAA AAGATGCTGA AGATCAGTTG GGTGCACGAG   1500
TGGGTTACAT CGAACTGGAT CTCAACAGCG GTAAGATCCT TGAGAGTTTT CGCCCCGAAG   1560
AACGTTTTCC AATGATGAGC ACTTTTAAAG TTCTGCTATG TGGCGCGGTA TTATCCCGTG   1620
TTGACGCCGG GCAAGAGCAA CTCGGTCGCC GCATACACTA TTCTCAGAAT GACTTGGTTG   1680
AGTACTCACC AGTCACAGAA AAGCATCTTA CGGATGGCAT GACAGTAAGA GAATTATGCA   1740
GTGCTGCCAT AACCATGAGT GATAACACTG CGGCCAACTT ACTTCTGACA ACGATCGGAG   1800
GACCGAAGGA GCTAACCGCT TTTTTGCACA ACATGGGGGA TCATGTAACT CGCCTTGATC   1860
GTTGGGAACC GGAGCTGAAT GAAGCCATAC CAAACGACGA GCGTGACACC ACGATGCCTG   1920
CAGCAATGGC AACAACGTTG CGCAAACTAT TAACTGGCGA ACTACTTACT CTAGCTTCCC   1980
GGCAACAATT AATAGACTGG ATGGAGGCGG ATAAAGTTGC AGGACCACTT CTGCGCTCGG   2040
CCCTTCCGGC TGGCTGGTTT ATTGCTGATA AATCTGGAGC CGGTGAGCGT GGGTCTCGCG   2100
GTATCATTGC AGCACTGGGG CCAGATGGTA AGCCCTCCCG TATCGTAGTT ATCTACACGA   2160
CGGGGAGTCA GGCAACTATG GATGAACGAA ATAGACAGAT CGCTGAGATA GGTGCCTCAC   2220
TGATTAAGCA TTGGTAACTG TCAGACCAAG TTTACTCATA TATACTTTAG ATTGATTTAA   2280
AACTTCATTT TTAATTTCTC TAGCGCGTTG ACATTGATTA TTGACTAGTT ATTAATAGTA   2340
ATCAATTACG GGGTCATTAG TTCATAGCCC ATATATGGAG TTCCGCGTTA CATAACTTAC   2400
GGTAAATGGC CCGCCTGGCT GACCGCCCAA CGACCCCCGC CCATTGACGT CAATAATGAC   2460
GTATGTTCCC ATAGTAACGC CAATAGGGAC TTTCCATTGA CGTCAATGGG TGGACTATTT   2520
ACGGTAAACT GCCCACTTGG CAGTACATCA AGTGTATCAT ATGCCAAGTA CGCCCCCTAT   2580
TGACGTCAAT GACGGTAAAT GGCCCGCCTG GCATTATGCC CAGTACATGA CCTTATGGGA   2640
CTTTCCTACT TGGCAGTACA TCTACGTATT AGTCATCGCT ATTACCATGG TGATGCGGTT   2700
TTGGCAGTAC ATCAATGGGC GTGGATAGCG GTTTGACTCA CGGGGATTTC CAAGTCTCCA   2760
CCCCATTGAC GTCAATGGGA GTTTGTTTTG GCACCAAAAT CAACGGGACT TTCCAAAATG   2820
TCGTAACAAC TCCGCCCCAT TGACGCAAAT GGGCGGTAGG CGTGTACGGT GGGAGGTCTA   2880
TATAAGCAGA GCTCTCTGGC TAACTAGAGA ACCCACTGCT TACTGGCTTA TCGAAATTAA   2940
TACGACTCAC TATAGGGAGA CCCAAGCTTG CATGCCTGCA GGCAACTCTT GTGGTTTCGT   3000
ATCTCTTACC TTACTTTTGG AAGAGAAACT GTACTTGAAT ATTTGGTCTC TTTCGGAGTG   3060
TGGATTCGCA CTCCTCCAGC CTATAGACCA CCAAATGCCC CTATCTTATC AACACTTCCG   3120
GAAACTACTG TTGTTAGACG ACGGGACCGA GGCAGGTCCC CTAGAAGAAG AACTCCCTCG   3180
CCTCGCAGAC GCAGATCTCA ATCGCCGCGT CGCAGAAGAT CTCAATCTCG GAATCTCAA    3240
```

```
TGTTAGTATT CCTTGGACTC ATAAGGTGGG AAACTTCACT GGGCTTTATT CCTCTACAGC    3300

ACCTATCTTT AATCCTGAAT GGCAAACTCC TTCCTTTCCT AAAATTCATT TACAAGAGGA    3360

CATTATTAAT AGGTGTCAAC AATTTGTGGG CCCTCTCACT GTAAATGAAA AGAGAAGATT    3420

GAAATTAATT ATGCCTGCTA GATTCTATCC TACCCACACT AAATATTTGC CCTTAGACAA    3480

AGGAATTAAA CCTTATTATC CAGATCAGGT AGTTAATCAT TACTTCCAAA CCAGACATTA    3540

TTTACATACT CTTTGGAAGG CGGGTATTCT ATATAAGAGA GAAACCACAC GTAGCGCATC    3600

ATTTTGCGGG TCACCATATT CTTGGGAACA AGAGCTACAG CATGGGAGGT TGGTCATCAA    3660

AACCTCGCAA AGGCATGGGG ACGAATCTTT CTGTTCCCAA CCCTCTGGGA TTCTTTCCCG    3720

ATCATCAGTT GGACCCTGTA TTCGGAGCCA ACTCAAACAA TCCAGATTGG GACTTCAACC    3780

CCATCAAGGA CCACTGGCCA GCAGCCAACC AGGTAGGAGT GGGAGCATTC GGGCCAGGGT    3840

TCACCCCTCC ACACGGCGGT GTTTTGGGGT GGAGCCCTCA GGCTCAGGGC ATGTTGACCC    3900

CAGTGTCAAC AATTCCTCCT CCTGCCTCCG CCAATCGGCA GTCAGGAAGG CAGCCTACTC    3960

CCATCTCTCC ACCTCTAAGA GACAGTCATC CTCAGGCCAT GCAGTGGAAT TCCACTGCCT    4020

TCCACCAAGC TCTGCAAGAC CCCAGAGTCA GGGGTCTGTA TTTTCCTGCT GGTGGCTCCA    4080

GTTCAGGAAC AGTAAACCCT GCTCCGAATA TTGCCTCTCA CATCTCGTCA ATCTCCGCGA    4140

GGACCGGGGA CCCTGTGACG AACATGGAGA ACATCACATC AGGATTCCTA GGACCCCTGC    4200

CCGTGTTACA GGCGGGGTTT TTCTTGTTGA CAAGAATCCT CACAATACCG CAGAGTCTAG    4260

ACTCGTGGTG GACTTCTCTC AATTTTCTAG GGGGATCACC CGTGTGTCTT GGCCAAAATT    4320

CGCGATCCCC AACCTCCAAT CACTCACCAA CCTCCTGTCC TCCAATTTGT CCTGGTTATC    4380

GCTGGATGTG TCTGCGGCGT TTTATCATAT TCCTCTTCAT CCTGCTGCTA TGCCTCATCT    4440

TCTTATTGGT TCTTCTGGAT TATCAAGGTA TGTTGCCCGT TTGTCCTCTA ATTCTAGGAT    4500

CAACAACAAC CAGTACGGGA CCATGCAAAA CCTGACGAC TCCTGCTCAA GGCAACTCTA    4560

TGTTTCCCTC ATGTTGCTGT ACAAAACCTA CGGATGGAAA TTGCACCTGT ATTCCCATCC    4620

CATCGTCTTG GGCTTTCGCA AAATACCTAT GGGAGTGGGC CTCAGTCCGT TTCTCTTGGC    4680

TCAGTTTACT AGTGCCATTT GTTCAGTGGT TCGTAGGGCT TTCCCCCACT GTTTGGCTTT    4740

CAGCTATATG GATGATGTGG TATTGGGGGC CAAGTCTGTA CAGCATCGTG AGTTCCTTTA    4800

TACCGCTGTT ACCAATTTTC TTTTGTCTCT GGGTATACAT TTAAACCCTA ACAAAACAAA    4860

AAGATGGGGT TATTCCCTAA ACTTCATGGG TTATGTAATT GGAAGTTGGG GAACATTGCC    4920

ACAGGATCAT ATTGTACAAA AAATCAAACA CTGTTTTAGA AAACTTCCTG TTAACAGGCC    4980

TATTGATTGG AAAGTATGTC AAAGAATTGT GGGTCTTTTG GGCTTTGCTG CTCCTTTTAC    5040

ACAATGTGGA TATCCTGCCT TAATGCCCTT GTATGCATGT ATACAAGCTA AACAGGCTTT    5100

CACTTTCTCG CCAACTTACA AGGCCTTTCT AAGTAAACAG TACATGAACC TTTACCCCGT    5160

TGCTCGGCAA CGGCCTGGTC TGTGCCAAGT ATTTGCTGAT GCAACCCCCA CTGGCTGGGG    5220

CTTGGCCATA GGCCATCAGC GCATGCGCGG AACCTTTGTG GCTCCTCTGC CGATCCATAC    5280

TGCGGAACTC CTAGCCGCTT GTTTTGCTCG CAGCCGGTCT GGAGCGAAAC TCATCGGAAC    5340

TGACAATTCT GTCGTCCTCT CGCGGAAATA TACCTCGTTT CCATGGCTAC TAGGCTGTGC    5400

TGCCAACTGG ATCCTTCGCG GGACGTCCTT TGTTTACGTC CCGTCGGCGC TGAATCCCGC    5460

GGACGACCCC TCTCGGGGCC GCTTGGGACT CTCTCGTCCC CTTCTCCGTC TGCCGTTCCA    5520

GCCGACCACG GGGCGCACCT CTCTTTACGC GGTCTCCCCG TCTGTGCCTT CTCATCTGCC    5580

GGTCCGTGTG CACTTCGCTT CACCTCTGCA CGTTGCATGG AGACCACCGT GAACGCCCAT    5640
```

```
CAGATCCTGC CCAAGGTCTT ACATAAGAGG ACTCTTGGAC TCCCCCCATC CATCACACTG    5700

GCGGCCGCTC GAGCATGCAT CTAGAGGGCC CTATTCTATA GTGTCACCTA AATGCTAGAG    5760

GATCTTTGTG AAGGAACCTT ACTTCTGTGG TGTGACATAA TTGGACAAAC TACCTACAGA    5820

GATTTAAAGC TCTAAGGTAA ATATAAAATT TTTAAGTGTA TAATGTGTTA AACTACTGAT    5880

TCTAATTGTT TGTGTATTTT AGATTCCAAC CTATGGAACT GATGAATGGG AGCAGTGGTG    5940

GAATGCCTTT AATGAGGAAA ACCTGTTTTG CTCAGAAGAA ATGCCATCTA GTGATGATGA    6000

GGCTACTGCT GACTCTCAAC ATTCTACTCC TCCAAAAAAG AAGAGAAAGG TAGAAGACCC    6060

CAAGGACTTT CCTTCAGAAT TGCTAAGTTT TTTGAGTCAT GCTGTGTTTA GTAATAGAAC    6120

TCTTGCTTGC TTTGCTATTT ACACCACAAA GGAAAAAGCT GCACTGCTAT ACAAGAAAAT    6180

TATGGAAAAA TATTTGATGT ATAGTGCCTT GACTAGAGAT CATAATCAGC CATACCACAT    6240

TTGTAGAGGT TTTACTTGCT TTAAAAAACC TCCCACACCT CCCCCTGAAC CTGAAACATA    6300

AAATGAATGC AATTGTTGTT GTTAACTTGT TTATTGCAGC TTATAATGGT TACAAATAAA    6360

GCAATAGCAT CACAAATTTC ACAAATAAAG CATTTTTTTC ACTGCATTCT AGTTGTGGTT    6420

TGTCCAAACT CATCAATGTA TCTTATCATG TCTGGATCAT CCCGCCATGG TATCAACGCC    6480

ATATTTCTAT TTACAGTAGG GACCTCTTCG TTGTGTAGGT ACCGCTGTAT TCCTAGGGAA    6540

ATAGTAGAGG CACCTTGAAC TGTCTGCATC AGCCATATAG CCCCCGCTGT TCGACTTACA    6600

AACACAGGCA CAGTACTGAC AAACCCATAC ACCTCCTCTG AAATACCCAT AGTTGCTAGG    6660

GCTGTCTCCG AACTCATTAC ACCCTCCAAA GTCAGAGCTG TAATTTCGCC ATCAAGGCA    6720

GCGAGGGCTT CTCCAGATAA AATAGCTTCT GCCGAGAGTC CGTAAGGGT AGACACTTCA    6780

GCTAATCCCT CGATGAGGTC TACTAGAATA GTCAGTGCGG CTCCCATTTT GAAAATTCAC    6840

TTACTTGATC AGCTTCAGAA GATGGCGGAG GGCCTCCAAC ACAGTAATTT TCCTCCCGAC    6900

TCTTAAAATA GAAAATGTCA AGTCAGTTAA GCAGGAAGTG GACTAACTGA CGCAGCTGGC    6960

CGTGCGACAT CCTCTTTTAA TTAGTTGCTA GGCAACGCCC TCCAGAGGGC GTGTGGTTTT    7020

GCAAGAGGAA GCAAAAGCCT CTCCACCCAG GCCTAGAATG TTTCCACCCA ATCATTACTA    7080

TGACAACAGC TGTTTTTTTT AGTATTAAGC AGAGGCCGGG GACCCCTGGG CCCGCTTACT    7140

CTGGAGAAAA AGAAGAGAGG CATTGTAGAG GCTTCCAGAG GCAACTTGTC AAAACAGGAC    7200

TGCTTCTATT TCTGTCACAC TGTCTGGCCC TGTCACAAGG TCCAGCACCT CCATACCCCC    7260

TTTAATAAGC AGTTTGGGAA CGGGTGCGGG TCTTACTCCG CCCATCCCGC CCCTAACTCC    7320

GCCCAGTTCC GCCCATTCTC CGCCCCATGG CTGACTAATT TTTTTTATTT ATGCAGAGGC    7380

CGAGGCCGCC TCGGCCTCTG AGCTATTCCA GAAGTAGTGA GGAGGCTTTT TTGGAGGCCT    7440

AGGCTTTTGC AAAAAGCTAA TTC                                           7463
```

(2) INFORMATION FOR SEQ ID NO:14:

(i) SEQUENCE CHARACTERISTICS:
        (A) LENGTH: 6375 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA"

(xi) SEQUENCE DESCRIPTION: SEQ ID NO:14:

```
CCCATTCGCC ATTCAGGCTG CGCAACTGTT GGGAAGGGCG ATCGGTGCGG GCCTCTTCGC    60

TATTACGCCA GCTGGCGAAA GGGGGATGTG CTGCAAGGCG ATTAAGTTGG GTAACGCCAG    120
```

-continued

```
GGTTTTCCCA GTCACGACGT TGTAAAACGA CGGCCAGTGC CAAGCTATAT AAATTAACCC    180

TCACTAAAGG GAATAAGCTT GCATGCCTGC AGGTCGACTC TAGAGGATCC CCGGGTACCG    240

AGCTCGAATT CCACTGCCTT CCACCAAACT CTGCAGGATC CAGAGTCAG  GGTCTGTAT     300

CTTCCTGCTG GTGGCTCCAG TTCAGGAACA GTAAACCCTG CTCCGAATAT TGCCTCTCAC    360

ATCTCGTCAA TCTCCGCGAG GACTGGGGAC CCTGTGACGA ACATGGAGAA CATCACATCA    420

GGATTCCTAG GACCCCTGCT CGTGTTACAG GCGGGGTTTT TCTTGTTGAC AAGAATCCTC    480

ACAATACCGC AGAGTCTAGA CTCGTGGTGG ACTTCTCTCA ATTTTCTAGG GGGATCTCCC    540

GTGTGTCTTG GCCAAAATTC GCAGTCCCCA ACCTCCAATC ACTCACCAAC CTCCTGTCCT    600

CCAATTTGTC CTGGTTATCG CTGGATGTGT CTGCGGCGTT TTATCATATT CCTCTTCATC    660

CTGCTGCTAT GCCTCATCTT CTTATTGGTT CTTCTGGATT ATCAAGGTAT GTTGCCCGTT    720

TGTCCTCTAA TTCCAGGATC AACAACAACC AGTACGGGAC CATGCAAAAC CTGCACGACT    780

CCTGCTCAAG GCAACTCTAT GTTTCCCTCA TGTTGCTGTA CAAAACCTAC GGATGGAAAT    840

TGCACCTGTA TTCCCATCCC ATCGTCCTGG GCTTTCGCAA ATACCTATG  GGAGTGGGCC    900

TCAGTCCGTT TCTCTTGGCT CAGTTTACTA GTGCCATTTG TTCAGTGGTT CGTAGGGCTT    960

TCCCCCACTG TTTGGCTTTC AGCTATATGG ATGATGTGGT ATTGGGGGCC AAGTCTGTAC   1020

AGCATCGTGA GTCCCTTTAT ACCGCTGTTA CCAATTTTCT TTTGTCTCTG GGTATACATT   1080

TAAACCCTAA CAAAACAAAA AGATGGGGTT ATTCCCTAAA CTTCATGGGC TACATAATTG   1140

GAAGTTGGGG AACTTTGCCA CAGGATCATA TTGTACAAAA GATCAAACAC TGTTTTAGAA   1200

AACTTCCTGT TAACAGGCCT ATTGATTGGA AAGTATGTCA AAGAATTGTG GGTCTTTTGG   1260

GCTTTGCTGC TCCATTTACA CAATGTGGAT ATCCTGCCTT AATGCCTTTG TATGCATGTA   1320

TACAAGCTAA ACAGGCTTTC ACTTTCTCGC CAACTTACAA GGCCTTTCTA AGTAAACAGT   1380

ACATGAACCT TTACCCCGTT GCTCGGCAAC GGCCTGGTCT GTGCCAAGTG TTTGCTGACG   1440

CAACCCCCAC TGGCTGGGGC TTGGCCATAG GCCATCAGCG CATGCGTGGA ACCTTTGTGG   1500

CTCCTCTGCC GATCCATACT GCGGAACTCC TAGCCGCTTG TTTTGCTCGC AGCCGGTCTG   1560

GAGCAAAGCT CATCGGAACT GACAATTCTG TCGTCCTCTC GCGGAAATAT ACATCGTTTC   1620

CATGGCTGCT AGGCTGTACT GCCAACTGGA TCCTTCGCGG GACGTCCTTT GTTTACGTCC   1680

CGTCGGCGCT GAATCCCGCG GACGACCCCT CTCGGGGCCG CTTGGGACTC TCTCGTCCCC   1740

TTCTCCGTCT GCCGTTCCAG CCGACCACGG GGCGCACCTC TCTTTACGCG GTCTCCCCGT   1800

CTGTGCCTTC TCATCTGCCG GTCCGTGTGC ACTTCGCTTC ACCTCTGCAC GTTGCATGGA   1860

GACCACCGTG AACGCCCATC AGATCCTGCC CAAGGTCTTA CATAAGAGGA CTCTTGGACT   1920

CCCAGCAATG TCAACGACCG ACCTTGAGGC CTACTTCAAA GACTGTGTGT TTAAGGACTG   1980

GGAGGAGCTG GGGGAGGAGA TTAGGTTAAA GGTCTTTGTA TTAGGAGGCT GTAGGCACAA   2040

ATTGGTCTGC GCACCAGCAC CATGCAACTT TTTCACCTCT GCCTAATCAT CTCTTGTACA   2100

TGTCCCACTG TTCAAGCCTC CAAGCTGTGC CTTGGGTGGC TTTGGGGCAT GGACATTGAC   2160

CCTTATAAAG AATTTGGAGC TACTGTGGAG TTACTCTCGT TTTTGCCTTC TGACTTCTTT   2220

CCTTCCGTCA GAGATCTCCT AGACACCGCC TCAGCTCTGT ATCGAGAAGC CTTAGAGTCT   2280

CCTGAGCATT CCTCACCTCA CCATACTGCA CTCAGGCAAG CCATTCTCTG CTGGGGGGAA   2340

TTGATGACTC TAGCTACCTG GGTGGGTAAT AATTTGGAAG ATCCAGCATC TAGGGATCTT   2400

GTAGTAAATT ATGTTAATAC TAACGTGGGT TTAAAGATCA GGCAACTATT GTGGTTTCAT   2460

ATATCTTGCC TTACTTTTGG AAGAGAGACT GTACTTGAAT ATTTGGTCTC TTTCGGAGTG   2520
```

```
TGGATTCGCA CTCCTCCAGC CTATAGACCA CCAAATGCCC CTATCTTATC AACACTTCCG    2580

GCCGGAAACT ACTGTTGTTA GACGACGGGA CCGAGGCAGG TCCCCTAGAA GAAGAACTCC    2640

CTCGCCTCGC AGACGCAGAT CTCCATCGCC GCGTCGCAGA AGATCTCAAT CTCGGGAATC    2700

TCAATGTTAG TATTCCTTGG ACTCATAAGG TGGGAAACTT TACGGGCTT TATTCCTCTA     2760

CAGTACCTAT CTTTAATCCT GAATGGCAAA CTCCTTCCTT TCCTAAGATT CATTTACAAG    2820

AGGACATTAT TAATAGGTGT CAACAATTTG TGGGCCCTCT CACTGTAAAT GAAAAGAGAA    2880

GATTGAAATT AATTATGCCT GCTAGATTCT ATCCTACCCA CACTAAATAT TTGCCCTTAG    2940

ACAAAGGAAT TAAACCTTAT TATCCAGATC AGGTAGTTAA TCATTACTTC CAAACCAGAC    3000

ATTATTTACA TACTCTTTGG AAGGCTGGTA TTCTATATAA GCGGGAAACC ACACGTAGCG    3060

CATCATTTTG CGGGTCACCA ATGGAGCCAG TAGATCCTAA TCTAGAGCCC TGGAAGCATC    3120

CAGGAAGTCA GCCTAAAACT GCTTGTACCA ATTGCTATTG TAAAAAGTGT TGCTTTCATT    3180

GCCAAGTTTG TTTCATGACA AAAGCCTTAG GCATCTCCTA TGGCAGGAAG AAGCGGAGAC    3240

AGCGACGAAG AGCTCATCAG AACAGTCAGA CTCATCAAGC TTCTCTATCA AAGCAACCCA    3300

CCTCCCAATC CCGAGGGGAC CCGACAGGGC CCACGGAAGG GTCACCATAT TCTTGGGAAC    3360

AAGAGCTACA GCATGGGAGG TTGGTCATCA AAACCTCGCA AAGGCATGGG GACGAATCTT    3420

TCTGTTCCCA ATCCTCTGGG ATTCTTTCCC GATCATCAGT TGGACCCTGC ATTCGGAGCC    3480

AACTCAAACA ATCCAGATTG GGACTTCAAC CCCGTCAAGG ACGACTGGCC AGCAGCCAAC    3540

CAAGTAGGAG TGGGAGCATT CGGGCCAAGG CTCACCCCTC CACACGGCGG TATTTTGGGG    3600

TGGAGCCCTC AGGCTCAGGG CATATTGACC ACAGTGTCAA CAATTCCTCC TCCTGCCTCC    3660

ACCAATCGGC AGTCAGGAAG GCAGCCTACT CCCATCTCTC CACCTCTAAG AGACAGTCAT    3720

CCTCAGGCCA TGCAGTGGAA TTCCCTATAG TGAGTCGTAT TAAATTCGTA ATCATGGTCA    3780

TAGCTGTTTC CTGTGTGAAA TTGTTATCCG CTCACAATTC CACACAACAT ACGAGCCGGA    3840

AGCATAAAGT GTAAAGCCTG GGGTGCCTAA TGAGTGAGCT AACTCACATT AATTGCGTTG    3900

CGCTCACTGC CCGCTTTCCA GTCGGGAAAC CTGTCGTGCC AGCTGCATTA ATGAATCGGC    3960

CAACGCGCGG GGAGAGGCGG TTTGCGTATT GGGCGCTCTT CCGCTTCCTC GCTCACTGAC    4020

TCGCTGCGCT CGGTCGTTCG GCTGCGGCGA GCGGTATCAG CTCACTCAAA GGCGGTAATA    4080

CGGTTATCCA CAGAATCAGG GGATAACGCA GGAAAGAACA TGTGAGCAAA AGGCCAGCAA    4140

AAGGCCAGGA ACCGTAAAAA GGCCGCGTTG CTGGCGTTTT TCCATAGGCT CCGCCCCCCT    4200

GACGAGCATC ACAAAAATCG ACGCTCAAGT CAGAGGTGGC GAAACCCGAC AGGACTATAA    4260

AGATACCAGG CGTTTCCCCC TGGAAGCTCC CTCGTGCGCT CTCCTGTTCC GACCCTGCCG    4320

CTTACCGGAT ACCTGTCCGC CTTTCTCCCT TCGGGAAGCG TGGCGCTTTC TCAATGCTCA    4380

CGCTGTAGGT ATCTCAGTTC GGTGTAGGTC GTTCGCTCCA AGCTGGGCTG TGTGCACGAA    4440

CCCCCCGTTC AGCCCGACCG CTGCGCCTTA TCCGGTAACT ATCGTCTTGA GTCCAACCCG    4500

GTAAGACACG ACTTATCGCC ACTGGCAGCA GCCACTGGTA ACAGGATTAG CAGAGCGAGG    4560

TATGTAGGCG GTGCTACAGA GTTCTTGAAG TGGTGGCCTA ACTACGGCTA CACTAGAAGA    4620

ACAGTATTTG GTATCTGCGC TCTGCTGAAG CCAGTTACCT TCGGAAAAAG AGTTGGTAGC    4680

TCTTGATCCG GCAAACAAAC CACCGCTGGT AGCGGTGGTT TTTTTGTTTG CAAGCAGCAG    4740

ATTACGCGCA GAAAAAAAGG ATCTCAAGAA GATCCTTTGA TCTTTTCTAC GGGGTCTGAC    4800

GCTCAGTGGA ACGAAAACTC ACGTTAAGGG ATTTTGGTCA TGAGATTATC AAAAAGGATC    4860

TTCACCTAGA TCCTTTTAAA TTAAAAATGA AGTTTTAAAT CAATCTAAAG TATATATGAG    4920
```

```
TAAACTTGGT CTGACAGTTA CCAATGCTTA ATCAGTGAGG CACCTATCTC AGCGATCTGT    4980

CTATTTCGTT CATCCATAGT TGCCTGACTC CCCGTCGTGT AGATAACTAC GATACGGGAG    5040

GGCTTACCAT CTGGCCCCAG TGCTGCAATG ATACCGCGAG ACCCACGCTC ACCGGCTCCA    5100

GATTTATCAG CAATAAACCA GCCAGCCGGA AGGGCCGAGC GCAGAAGTGG TCCTGCAACT    5160

TTATCCGCCT CCATCCAGTC TATTAATTGT TGCCGGGAAG CTAGAGTAAG TAGTTCGCCA    5220

GTTAATAGTT TGCGCAACGT TGTTGCCATT GCTACAGGCA TCGTGGTGTC ACGCTCGTCG    5280

TTTGGTATGG CTTCATTCAG CTCCGGTTCC CAACGATCAA GGCGAGTTAC ATGATCCCCC    5340

ATGTTGTGCA AAAAAGCGGT TAGCTCCTTC GGTCCTCCGA TCGTTGTCAG AAGTAAGTTG    5400

GCCGCAGTGT TATCACTCAT GGTTATGGCA GCACTGCATA ATTCTCTTAC TGTCATGCCA    5460

TCCGTAAGAT GCTTTTCTGT GACTGGTGAG TACTCAACCA AGTCATTCTG AGAATAGTGT    5520

ATGCGGCGAC CGAGTTGCTC TTGCCCGGCG TCAATACGGG ATAATACCGC GCCACATAGC    5580

AGAACTTTAA AAGTGCTCAT CATTGGAAAA CGTTCTTCGG GGCGAAAACT CTCAAGGATC    5640

TTACCGCTGT TGAGATCCAG TTCGATGTAA CCCACTCGTG CACCCAACTG ATCTTCAGCA    5700

TCTTTTACTT TCACCAGCGT TTCTGGGTGA GCAAAAACAG GAAGGCAAAA TGCCGCAAAA    5760

AAGGGAATAA GGGCGACACG GAAATGTTGA ATACTCATAC TCTTCCTTTT TCAATATTAT    5820

TGAAGCATTT ATCAGGGTTA TTGTCTCATG AGCGGATACA TATTTGAATG TATTTAGAAA    5880

AATAAACAAA TAGGGGTTCC GCGCACATTT CCCCGAAAAG TGCCACCTGA AATTGTAAAC    5940

GTTAATGTTT TGTTAAATTT CGCGTTAAAT ATTTGTTAAA TCAGCTTATT TTTTAACCAG    6000

TAAGCAGAAA ATGACAAAAA TCCTTATAAA TCAAAAGAAT AGACCGAGTT AGTTGTGAGT    6060

GTTGTTCCAG TTTGGAACAA GAGTCCACTA TTAAAGAACG TGGACTCCAA CGTAAAACCG    6120

TCTATCAGGG CGATGGCCCA CTACGTGAAC CATCACCCAA ATCAAGTTTT TGGAGGTCGA    6180

GGTGCCGTAA AGCACTAAAT CGGAACCCTA AAGGGAGCCC CCGATTTAGA GCTTGACGGG    6240

GAAAGCCGGC GAACGTGGCG AGAAAGGAAG GGAAGAAAGC GAAAGGAGCG GGCGCTAGGG    6300

CGCTGGCAAG TGTAGCGGTC ACGCTGCGCG TAACCACCAC ACCCGCCGCG CTTAATGCGC    6360

CGCTACTGGG CGCGT                                                    6375

(2) INFORMATION FOR SEQ ID NO:15:

(i) SEQUENCE CHARACTERISTICS:
        (A) LENGTH: 483 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

AAGCTTTGGA GCTAAGCCAG CAATGGTAGA GGGAAGATTC TGCACGTCCC TTCCAGGCGG     60

CCTCCCCGTC ACCACCCCCC CCAACCCGCC CCGACCGGAG CTGAGAGTAA TTCATACAAA    120

AGGACTCGCC CCTGCCTTGG GGAATCCCAG GGACCGTCGT TAAACTCCCA CTAACGTAGA    180

ACCCAGAGAT CGCTGCGTTC CCGCCCCCTC ACCCGCCCGC TCTCGTCATC ACTGAGGTGG    240

AGAAGAGCAT GCGTGAGGCT CCGGTGCCCG TCAGTGGGCA GAGCGCACAT CGCCCACAGT    300

CCCCGAGAAG TTGGGGGGAG GGGTCGGCAA TTGAACCGGT GCCTAGAGAA GGTGGCGCGG    360

GGTAAACTGG GAAAGTGATG TCGTGTACTG GCTCCGCCTT TTTCCCGAGG GTGGGGGAGA    420

ACCGTATATA AGTGCAGTAG TCGCCGTGAA CGTTCTTTTT CGCAACGGGT TTGCCGCCTC    480
```

```
GAG                                                                    483

(2) INFORMATION FOR SEQ ID NO:16:

(i) SEQUENCE CHARACTERISTICS:
        (A) LENGTH: 825 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

AATGAAAGAC CCCACCTGTA GGTTTGGCAA GCTAGCTTAA GTAACGCCAT TTTGCAAGGC       60

ATGGAAAAAT ACATAACTGA GAATAGAGAA GTTCAGATCA AGGTCAGGAA CAGATGGAAC      120

AGCTGAATAT GGGCCAAACA GGATATCTGT GGTAAGCAGT TCCTGCCCCG GCTCAGGGCC      180

AAGAACAGAT GGAACAGCTG AATATGGGCC AAACAGGATA TCTGTGGTAA GCAGTTCCTG      240

CCCCGGCTCA GGGCCAAGAA CAGATGGTCC CCAGATGCGG TCCAGCCCTC AGCAGTTTCT      300

AGCTGGAGTT CCGCGTTACA TAACTTACGG TAAATGGCCC GCCTGGCTGA CCGCCCAACG      360

ACCCCCGCCC ATTGACGTCA ATAATGACGT ATGTTCCCAT AGTAACGCCA ATAGGGACTT      420

TCCATTGACG TCAATGGGAG TTTGTTTTGG CACCAAAATC AACGGGACTT TCCAAAATGT      480

CGTAATAACC CCGCCCCGTT GACGCAAATG GGCGGTAGGC GTGTACTCTA GATGCTACAT      540

ATAAGCAGCT GCTTTTTGCC TGTACTGGGT CTCTCTGGTT AGACCAGATC TGAGCCTGGG      600

AGCTCTCTGG CTAACTAGGG AACCCACTGC TTAAGCCTCG AATTCAGCTC AATAAAAGAG      660

CCCACAACCC CTCACTCGGG GCGCCAGTCC TCCGATTGAC TGAGTCGCCC GGGTACCCGT      720

GTATCCAATA AACCCTCTTG CAGTTGCATC CGACTTGTGG TCTCGCTGTT CCTTGGGAGG      780

GTCTCCTCTG AGTGATTGAC TACCCGTCAG CGGGGGTCTT TCATT                      825
```

RECOMBINANT HEPATITIS VIRUS VECTORS

FIELD OF THE INVENTION

The present invention relates to recombinant hepatitis viral vectors useful for the expression of functional heterologous gene products in liver cells. These vectors also find use in anti-viral, anti-tumor and/or gene therapy, particularly for the correction of inherited single-gene defects.

BACKGROUND OF THE INVENTION

A large number of human genetic disorders could be treated by expression of missing or mutant genes in the liver. These disorders include familial hypercholesterolemia (deficiency of LDL receptors), ornithine transcarbamylase deficiency (a lethal liver metabolic disease), and hepatobiliary disease of cystitic fibrosis to name but a few metabolic disorders which effect the liver. In addition to correction of metabolic disorders effecting the liver, a number of primary tumors of the liver are known and would benefit from expression of anti-neoplastic genes in the liver [e.g., VDEPT; Huber et al. (1991) Proc. Natl. Acad. Sci. USA 88:8039].

In addition to permitting correction of inherited disorders which effect the liver, the ability to express genes in the liver permits gene therapy for a number of disorders whose primary defect is not located in the liver. For example, a number of inborn errors of metabolism result in high concentrations of toxic metabolites in the blood; transfer of a correct gene encoding the defective enzyme to the liver could permit metabolism of the toxic metabolites relieving the metabolic defect even though the site of the deficiency is outside of the liver (e.g., replacement of adenosine deaminase to remove toxic levels of adenosine and deoxyadenosine in the circulation of severe combined immunodeficiency patients).

Current approaches to targeting genes to the liver have focused upon ex vivo gene therapy. Ex vivo liver-directed gene therapy involves the surgical removal of liver cells, transduction of the liver cells in vitro (e.g., infection of the explanted cells with recombinant retroviral vectors) followed by injection of the genetically modified liver cells into the liver or spleen of the patient. A serious drawback for ex vivo gene therapy of the liver is the fact that hepatocyctes (i.e., liver cells) cannot be maintained and expanded in culture. Therefore, the success of ex vivo liver-directed gene therapy depends upon the ability to efficiently and stably engraft the genetically modified (i.e., transduced) hepatocyctes and their progeny. It has been reported that even under optimal conditions, autologous modified liver cells injected into the liver or spleen which engraft represent only a small percentage (less than 10%) of the total number of cells in the liver [Chowdhury et al. (1991) Science 254:1802]. Ectopic engraftment of transduced primary hepatocytes into the peritoneal cavity has been tried to address the problem of engraftment in the liver [Ledley, et al. (1987) Proc. Natl. Acad. Sci. USA 84:5335; Wilson et al. (1988) Proc. Natl. Acad. Sci. USA 85:3014 and Wolff et al. (1987) Proc. Natl. Acad. Sci. USA 84:3344].

Given the problems associated with ex vivo liver-directed gene therapy, in vivo approaches have been investigated for the transfer of genes into hepatocytes, including the use of recombinant retroviruses, recombinant adenoviruses, liposomes and molecular conjugates [Jaffe et al. (1992) Nature Gent. 1:372; Kaneda et al. (1989) Science 243:375; and Wu et al. (1989) J. Biol. Chem. 16985]. While these in vivo approaches do not suffer from the drawbacks associated with ex vivo liver-directed gene therapy, they do not provide a means to specifically target hepatocytes. In addition, several of these approaches require that a partial hepatectomy be performed in order to achieve prolonged expression of the transferred genes in vivo [Wilson (1992) J. Biol. Chem. 267:963].

Ideally, liver-directed gene therapy would be achieved by in vivo transfer of genes using vectors which specifically target hepatocytes. Hepatotrophic viruses, such as human hepatitis B virus (HBV), can be delivered via the circulation and their gene products are known to be expressed specifically in the liver. However, to date, the ability to express a foreign gene in the context of a HBV has not been reported. The art needs human HBV vectors capable of carrying and expressing foreign genes to allow in vivo liver-directed and liver-specific gene therapy.

SUMMARY OF THE INVENTION

The present invention relates to recombinant hepatitis viral vectors useful for the expression of functional heterologous gene products in liver cells. It is contemplated that these vectors will find use in anti-viral, anti-tumor and/or gene therapy, particularly for the correction of inherited single-gene defects. These novel recombinant vectors may be used to deliver genes to cells in vivo by a variety of means including infection and direct injection of vector DNA.

The present invention provides a recombinant hepatitis virus genome comprising heterologous gene sequences capable of expressing at least one functional heterologous gene product. The present invention is illustrated using recombinant HBV genomes (i.e., the human HBV); however, the invention contemplates the use of any hepatitis B virus, including but not limited to woodchuck hepatitis virus (WHV), ground squirrel hepatitis virus (GSHV), tree squirrel hepatitis virus (TSHV), duck hepatitis virus (DHBV) and heron hepatitis virus (HHBV). The art is well aware that the genomic organization of these various hepatitis B virus is similar and that the teachings of the present invention can be translated to other hepatitis B viruses (e.g., DHBV, WHV, etc).

It is contemplated that in some embodiments, the recombinant virus genome further comprises an endogenous viral promoter. In one embodiment, the viral promoter of the recombinant virus genome is selected from the group consisting of the core/pol promoter and the preS1 promoter. In another embodiment, the recombinant virus genome further comprises a heterologous promoter. In one embodiment with a heterologous promoter, the heterologous promoter of the recombinant virus genome is selected from the group consisting of the CMV-IE promoter, the human elongation factor 1α gene promoter, the SV40 enhancer/promoter, the Rous sarcoma virus long terminal repeat, the α-fetoprotein gene promoter and the recombinant Moloney murine leukemia virus long terminal repeat containing CMV-IE/HIV-1 TAR sequences listed in SEQ ID NO:16. In one preferred embodiment of the recombinant virus genome, the genome is replication competent. However, in an alternative embodiment, the recombinant virus genome is replication defective.

In one particularly preferred embodiment, the present invention provides a recombinant hepatitis B virus genome comprising pol gene sequences, X gene sequences and preS1/preS2/S gene sequences and heterologous gene sequences wherein the recombinant genome is capable of expressing at least one functional heterologous gene product. In one embodiment, the recombinant hepatitis B virus genome is replication defective; the replication defective virus may be capable of being packaged into infectious viral particles or alternatively it may exceed in size the packaging limit. In one embodiment of the replication-defective recombinant hepatitis B virus genome contains a deletion within the pol gene. It is contemplated that the deletion within the pol gene may be located within the preS/preS2/S gene sequences. However, it is also contemplated that the deletion may be located within the pol gene and the preS/preS2/S gene sequences. In addition, it is contemplated that the recombinant virus genome will lack a functional X and/or S gene. In embodiments of the present invention in which the genome lacks a functional S gene, it is contemplated that the recombinant virus genome further lacks functional preS1/S and preS2/S genes.

The present invention also provides methods for the encapsidation of a recombinant hepatitis B virus genome, comprising the steps of providing: i) a recombinant hepatitis B virus genome comprising pol gene sequences, X gene sequences and preS1/preS2/S gene sequences and heterologous gene sequences wherein the recombinant genome is capable of expressing at least one functional heterologous gene product and wherein the recombinant genome lacks the ability to produce at least one viral product required for packaging said viral genome; ii) at least one plasmid capable of providing in trans hepatitis B virus gene products sufficient to complement the recombinant viral genome lacking the ability to produce at least one viral product required for packaging; as well as a liver cell; and b) introducing the recombinant hepatitis virus genome and the plasmid(s) into the liver cell under conditions such that the recombinant hepatitis virus genome is encapsidated into viral particles. It is contemplated that the liver cell of the present invention be selected from the group consisting of human liver cells [including HepG2 cells (ATCC HB 8065), HuH7 cells, Hep 3B (ATCC HB 8064), WRL 68 (ATCC CL 48), Chang liver (ATCC CCL 13), SK-HEP-1 (ATCC HTB 52) and PLC/PRF/5 (ATCC CRL 8024)], avian liver cells (e.g., duck and chicken liver cells), non-human primate liver cells, and rodent liver cells. Any cell capable of expressing the viral gene products provided in trans and capable of express the gene products encoded by the recombinant viral genome (and capable of permitting replication of the viral genome if the genome is replication competent) may be employed.

In one embodiment of the method, the recombinant virus genome contains a deletion within the pol gene. In embodiments of the invention with pol gene deletion, it is contemplated that at least one plasmid used in the method encode the product of the hepatitis B virus pol gene. It is also contemplated that the recombinant virus genome contains a deletion within the preS/preS2/S gene sequences. In particular, it is contemplated that the plasmid encodes the products of the hepatitis B virus preS/preS2/S gene sequences. It is also contemplated that the recombinant virus genome contains a deletion within the pol gene and the preS/preS2/S gene sequences.

In another embodiment of the method, the plasmid encodes the products of the hepatitis B virus preS/preS2/S gene sequences and the product of the hepatitis B virus pol gene. In yet another embodiment, the recombinant virus genome lacks a functional X gene.

DEFINITIONS

Figure 1A:
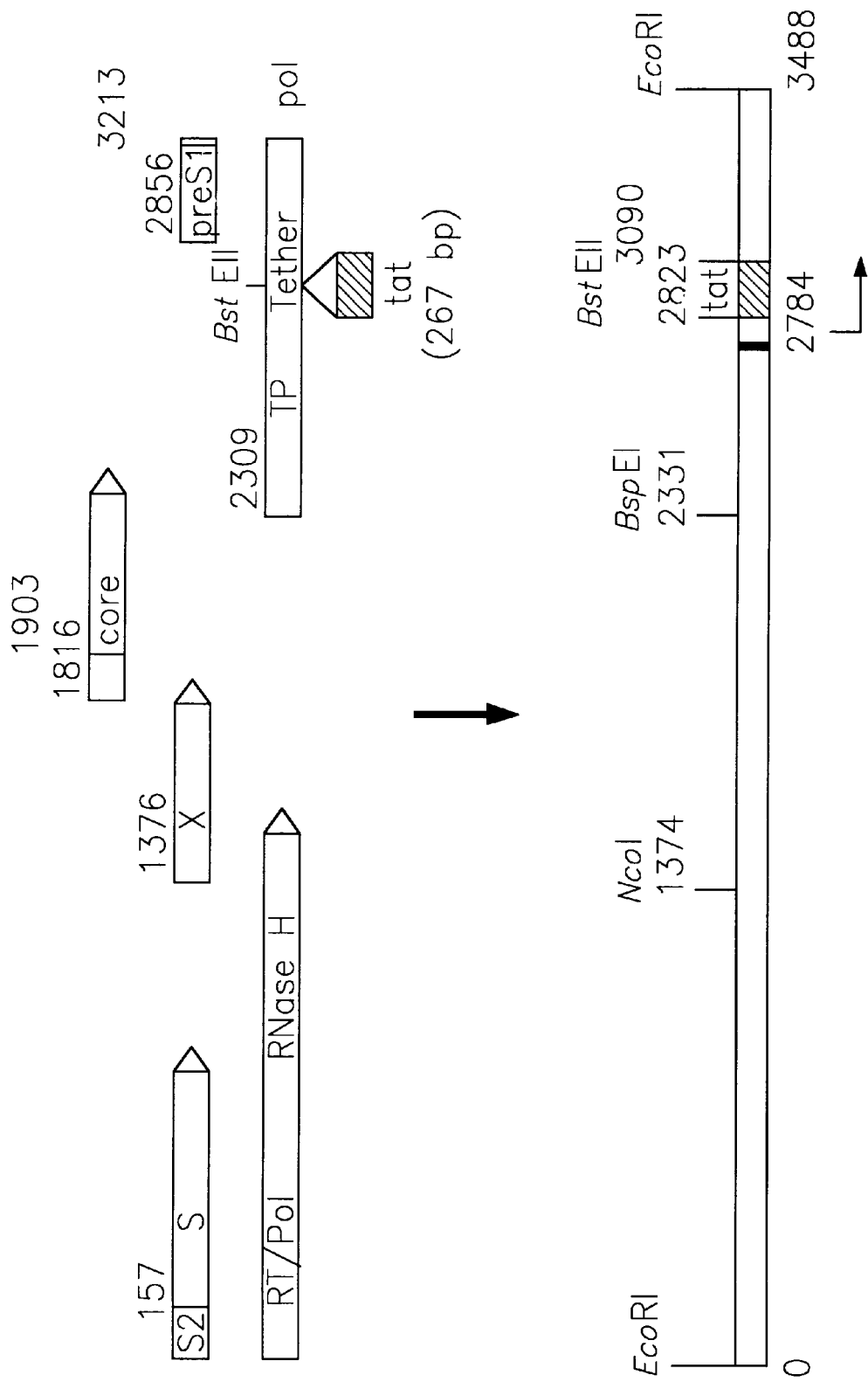
FIG. 1A is a schematic representation of the HBVtat virus (monomer form opened at the unique EcoRI site) as contained on pTHBVT.

To facilitate understanding of the invention, a number of terms are defined below.

As used herein, the term "hepatitis virus" refers to a hepatotrophic virus in the group termed hepadnaviruses. Hepatitis viruses include the human hepatitis B virus (HBV) which infects humans and certain non-human primates, woodchuck hepatitis virus (WHV), ground squirrel hepatitis virus (GSHV), tree squirrel hepatitis virus (TSHV), duck hepatitis virus (DHBV) and heron hepatitis virus (HHBV).

As used herein, the term "capable of expressing at least one functional heterologous gene product" when used in reference to a recombinant viral vector containing heterologous gene sequences means the viral vector is capable of producing a functional gene product from the heterologous gene sequences. A "functional" gene product is a gene product capable of carrying out the functions normally associated with that gene product. For example, a functional Tat protein is capable of transctivating the HIV-1 LTR. The functional heterologous gene product may be expressed as a fusion protein with viral protein sequences. A "functional HBV gene" (e.g., a functional X gene, a functional S gene) indicates that the HBV gene is capable of expressing a functional gene product (e.g., in the case of the S gene, a functional S gene is capable of expressing functional HBsAg). The location of the open reading frames (ORFs) encoding HBV gene products are known. For example, the start or ATG codon for the HBV X gene is located at nucleotides 1376–1378 of SEQ ID NO:1 (DNA sequence of the genome of HBV adw 2 in a linear form opened at the unique EcoRI site of the genome) and the stop codon for the X gene (TAA) is encoded by nucleotides 1838–1840 of SEQ ID NO:1. The start codon for the core gene is located at nucleotides 1873–1875 and the stop codon (TAG) is located at nucleotides 2458–2460 of SEQ ID NO:1. The start codon for the pol gene is located at nucleotides 2309–2311 and the stop codon (TGA) is located at nucleotides 1623–1625 of SEQ ID NO:1. The location of additional ORFs (e.g., precore, surface antigens, etc.) within SEQ ID NO:1 are known to the art.

Recombinant HBV genomes which lack gene sequences encoding gene products required for packaging of the viral genome may be encapsidated by providing the missing viral gene products in trans. Plasmids capable of expressing the missing gene products or helper virus capable of expressing the missing gene products may be transferred into a cell along with the defective genome. The defective genome will be packaged into mature viral particles as long as the transfected cell expresses all necessary viral gene products and the defective viral genome does not exceed the maximum packaging size.

Plasmids which are capable of providing in trans HBV gene products "sufficient to complement a recombinant viral genome deficient in at least one HBV gene product required for packaging viral DNA" are plasmids which direct the expression of the missing HBV gene products at a level sufficient to permit encapsidation of the deficient recombinant viral genome into mature viral particles (i.e., infectious particles).

A recombinant HBV genome which lacks a functional HBV gene (e.g., the X gene) is a genome which lacks the ability to produce a functional HBV gene product. The inability to produce a functional form of a given HBV gene product may be due to a deletion of all or a part of a HBV gene, point mutations, insertions, and/or frame-shift mutations which preclude expression of a functional gene product.

As used herein, the term "encapsidating" refers to the insertion of a viral genome into a mature viral particle (i.e., an infectious as opposed to a core viral particle when used in the context of HBV). The terms "encapsidating" and "packaging" are used herein interchangeably.

A "liver cell" refers to any cell derived from a liver including primary hepatocytes, cultured liver cells, cells within the liver tissue of an animal (including a human) and hepatoma cell lines.

As used herein, the term "polyA$^+$RNA" refers to RNA molecules having a stretch of adenine nucleotides at the 3' end. This polyadenine stretch is also referred to as a "poly-A tail". Eucaryotic mRNA molecules contain poly-A tails and are referred to as polyA$^+$RNA.

As used herein, the term "in trans" is used in reference to complementation of a defective viral genome indicates that a piece of genetic material other than the viral genome encodes the viral gene products which cannot be expressed by the defective viral genome.

The term "trans-acting" is used in reference to the controlling effect of a regulatory gene on a gene present on a different chromosome. In contrast to promoters, repressors are not limited in their binding to the DNA molecule that includes their genetic information. Therefore, repressors are sometimes referred to as trans-acting control elements.

The term "trans-activation" as used herein refers to the activation of gene sequences by factors encoded by a regulatory gene which is not necessarily contiguous with the gene sequences which it binds to and activates. For example, the HIV-1 regulatory protein Tat is encoded by the tat gene and binds to and activates (i.e., trans-activates) expression from the HIV LTR.

As used herein, the term "cis" is used in reference to the presence of genes on the same chromosome. The term "cis-acting" is used in reference to the controlling effect of a regulatory gene on a gene present on the same chromosome. For example, promoters, which affect the synthesis of downstream mRNA are cis-acting control elements.

As used herein, the term "packaging signal" or "packaging sequence" refers to sequences located within the hepatitis B virus genome which are required for encapsidation of viral DNA during viral particle formation.

As used herein, the terms "hepatitis virus vector," "HBV vector" or grammatical equivalents are used in reference to hepatitis B viruses which have been modified so as to serve as vectors for introduction of nucleic acid into cells.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in procaryotes usually include a promoter, an operator (optional), and a ribosome binding site, often along with other sequences. Eucaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "genetic cassette" as used herein refers to a fragment or segment of DNA containing a particular grouping of genetic elements. The cassette can be removed and inserted into a vector or plasmid as a single unit.

The term "transfection" as used herein refers to the introduction of foreign DNA into eucaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "transduction" refers to the delivery of a gene(s) using a viral vector by means of infection rather than by transfection.

As used herein, the term "TATA element" or "TATA box" is used in reference to a segment of DNA, located approximately 19–27 base pairs upstream from the start point of eucaryotic structural genes and viral genes, to which RNA polymerase binds. The TATA box is approximately 7 base pairs in length, often comprising the sequence "TATAAAA." The TATA box is also sometimes referred to as the "Hogness box."

The term "CAAT box" or "CAAT element" refers to a conserved DNA sequence located approximately 75 bp upstream from the start point of eucaryotic structural genes, to which RNA polymerase binds.

As used herein, the term "tat" is used in reference to the HIV gene which encodes "Tat," a protein which induces high-level expression of HIV genes.

As used herein, the term "long terminal repeat (LTR)" is used in reference to domains of base pairs located at the ends of retroviral DNA's. These LTRs may be several hundred base pairs in length. LTR's often provide functions fundamental to the expression of most eucaryotic genes (e.g., promotion, initiation and polyadenylation of transcripts).

As used herein, the term "TAR" is used in reference to the "trans-activation response" genetic element located in the U5 region of the HIV LTR. This element mediates the action of tat, by physically binding to the viral trans-activator tat.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1M NaCl (see e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. Primers are used in the polymerase chain reaction for the amplification of a specific target sequence.

As used herein, the term "probe" refers to an oligonucleotide (i.e., a sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for insertion into recombinant HBV vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "transcription unit" refers to the segment of DNA between the sites of initiation and termination of transcription and the regulatory elements necessary for the efficient initiation and termination. For example, a segment of DNA comprising an enhancer/promoter, a coding region and a termination and polyadenylation sequence comprises a transcription unit.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eucaryotes comprise "promoter" and "enhancer" elements. Promoters and enhancers consist of short arrays of DNA sequences that interact specifically with cellular proteins involved in transcription [Maniatis, T. et al, Science 236:1237 (1987)]. Promoter and enhancer elements have been isolated from a variety of eucaryotic sources including genes in yeast, insect and mammalian cells and viruses (analogous control elements, i.e., promoters, are also found in procaryotes). The selection of a particular promoter and enhancer depends on what cell type is to be used to express the protein of interest. Some eucaryotic promoters and enhancers have a broad host range while others are functional in a limited subset of cell types [for review see Voss, S. D. et al., Trends Biochem. Sci., 11:287 (1986) and Maniatis, T. et al., supra (1987)]. For example, the SV40 early gene enhancer is very active in a wide variety of cell types from many mammalian species and has been widely used for the expression of proteins in mammalian cells [Dijkema, R. et al., EMBO J. 4:761 (1985)]. Two other examples of promoter/enhancer elements active in a broad range of mammalian cell types are those from the human elongation factor 1α gene [Uetsuki, T. et al., J. Biol. Chem., 264:5791 (1989), Kim, D. W. et al., Gene 91:217 (1990) and Mizushima, S. and Nagata, S., Nuc. Acids. Res., 18:5322 (1990)] and the long terminal repeats of the Rous sarcoma virus [Gorman, C. M. et al., Proc. Natl. Acad. Sci. USA 79:6777 (1982)] and the human cytomegalovirus [Boshart, M. et al., Cell 41:521 (1985)].

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The term "factor" refers to a protein or group of proteins necessary for the transcription or replication of a DNA sequence. For example, SV40 T antigen is a replication factor which is necessary for the replication of DNA sequences containing the SV40 origin of replication. Transcription factors are proteins which bind to regulatory elements such as promoters and enhancers and facilitate the initiation of transcription of a gene.

Promoters and enhancers may bind to specific factors which increase the rate of activity from the promoter or enhancer. These factors may be present in all cell types or may be expressed in a tissue-specific manner or in virus infected cells. In the absence of such a factor the promoter may be inactive or may produce a low level of transcriptional activity. Such a low level of activity is referred to as a baseline or "basal" rate of activity. Additionally, viral promoter and enhancers may bind to factors encoded by the virus such that the viral promoter or enhancer is "activated" in the presence of the viral factor (in a virus infected cell or in a cell expressing the viral factor). The level of activity in the presence of the factor (i.e., activity "induced" by the factor) will be higher than the basal rate.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "gene of interest" refers to the gene inserted into the polylinker of an expression vector. When the gene of interest encodes a gene which provides a therapeutic function (such as an anti-tumor gene), the gene of interest may be alternatively called a remedial gene.

As used herein, the term "remedial gene" refers to a gene whose expression is desired in a cell to correct an error in cellular metabolism, to inactivate a pathogen or to kill a cancerous cell. For example, the adenosine deaminase (ADA) gene is the remedial gene when carried on a retroviral vector used to correct ADA deficiency in a patient.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Northern Blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, J. et al., *Molecular Cloning: A Laboratory Manual,* Cold Spring Harbor Press, Cold Spring Harbor, N.Y., pp 7.39–7.52). "Southern blot" refers to an analogous technique in which DNA rather than RNA is separated and analyzed.

The term "dot blot" as used herein refers to spotting a sample of containing protein or nucleic acid onto a solid support. The solid support is then probed with a labeled nucleic acid or antibody probe to detect the protein or nucleic acid species of interest. Alternatively the reaction products of an assay containing a radioactive substrate can be spotted onto a solid support and the unincorporated substrate washed prior to exposure of the support to X-ray film.

DESCRIPTION OF THE INVENTION

The present invention provides for the first time recombinant human hepatitis B virus (HBV) vectors capable of expressing functional heterologous gene products. The description of the invention is divided into: I. Hepatitis Viruses; II. Construction of Recombinant HBV Vectors; and III. Expression of Functional Heterologous Genes in Recombinant HBV Vectors.

I. Hepatitis Viruses

Hepadnaviruses include hepatitis B virus (HBV), woodchuck hepatitis virus (WHV), ground squirrel hepatitis virus (GSHV), tree squirrel hepatitis virus (TSHV), duck hepatitis virus (DHBV) and heron hepatitis virus (HHBV). HBV infects only humans and some non-human primates. Hepatitis viruses are hepatotropic viruses which comprise the smallest DNA viruses known; the genome of hepadnaviruses are only about 3200 base pairs in size.

Hepadnaviruses have genomes which comprise a circular DNA molecule which is only partially double-stranded (termed open circular or ocDNA). A cohesive overlap maintains the circular structure of the viral DNA; the plus and minus strands of the viral genome contain short direct repeats (DR1 and DR2) which form the cohesive overlap. DR1 and DR2 are important for replication of the viral DNA. Following attachment to and entry of HBV particles into liver cells, the virus is uncoated and the ocDNA is transported to the nucleus. The viral genome can then replicate and viral transcripts can be generated or the viral DNA can persist in a latent state [Blum et al. (1988) Liver 8:307]; the viral DNA can also integrate into the host's genome (the integrated viral DNA is always subgenomic in size and frequently contains rearrangement; pregenomic RNA is not transcribed from the integrated viral DNA). The presence of integrated HBV sequences is associated with hepatocellular carcinoma (HCC) in humans, rodents and birds.

Viral replication involves repair of the ocDNA to form covalently closed circular DNA (cccDNA); cccDNA serves as the template for transcription to form the RNA pregenome. The RNA pregenome is transported to the cytoplasm where it is packaged into core particles. Reverse transcription of the RNA pregenome occurs in these core particles to form a new minus strand of the viral DNA. Plus strand DNA synthesis then occurs using the minus strand as template; an intramolecular template switch (which is dependent upon the presence of the DRs) occurs to permit completion of the plus strand DNA and the formation of cccDNA. During the synthesis of the plus and minus DNA strands, core particles are assembled into mature virions by coating of the core particles with surface antigens. The mature virions are then exported from the liver cell.

The genomic organization of these viruses is extremely compact and efficiently organized with overlapping open reading frames (ORFs) [Ganem and Varmus (1987) Ann. Rev. Biochem. 56:651 and Nassal and Schaller (1993) Trends Microbiol. 1:221]. Hepatitis B virus (HBV), the prototype of hepadnaviruses and causative agent for human hepatitis, carries four major overlapping ORFs: preS1/preS2/S (collectively known as the envelope or surface gene), preC/C, X and P. The envelope gene contains the preS1, preS2 and S regions which are delineated by three in-frame initiation codons and code for three envelope proteins: large (L), middle (M) and major (S). The preC/C gene contains the preC and C regions, also delineated by two in-frame initiation codons, which code for secreted HBV e antigen (HBeAg) and capsid or core protein (HBcAg). The X gene codes for the transactivating protein which has activity on HBV enhancers and other cellular genes [Rossner (1992) J. Med. Virol. 36:101]. The C-terminus of the X gene overlaps with the N-terminus of the preC/C gene. The P or polymerase (pol) gene contains the longest ORF. It encompasses about 80% of the entire viral genome and overlaps with the C-terminus of the preC/C gene, the entire envelope gene and the N-terminus of the X gene. The product of the pol gene (designated as pol protein) contains three major functional domains: the terminal protein domain at the N-terminus, the reverse transcriptase/DNA polymerase in the central domain and the RNase H domain at the C-terminus [Bartenschlager and Schaller (1988) EMBO J. 7:4185 and Radziwill et al. (1990) J. Virol. 64:613]. The terminal protein and reverse transcriptase/DNA polymerase domains are separated by a spacer or tether region. Four promoter elements; the preS1, preS2/S, X and C or core/pol promoters, which regulate transcription of pregenomic and subgenomic messengers for expression of the corresponding genes, have been identified on the HBV genome [for a review see Schaller and Fischer (1991) Curr. Top. Microbiol. Immunol. 168:21]. Almost all nucleotides appear to be included in coding sequences and are therefore indispensable for the generation of infectious viral particles containing replication competent virus. Only the spacer or tether region may be non-essential for the pol gene function or HBV replication [Chang et al. (1990) J. Virol. 64:5553 and Radziwill et al. (1990), supra].

To date, HBV or other hepadnaviruses have not been engineered and used as gene transfer tools in recombinant DNA technology. Since HBV infection is known to be primarily specific for liver cells, the ability to use HBV as a recombinant vector or delivery system would be very useful for targeting a therapeutic gene(s) to liver cells. Several animal viruses have been successfully used as gene delivery vectors. Retroviruses, for example, which appear to be evolutionarily related to hepadnaviruses, have been successfully manipulated and used to deliver genes in vitro and in vivo [Eglitis et al. (1985) Science 230:1395; Miller et al. (1993) Methods Enzymol. 217:581; and Naldini et al. (1996) Science 272:263]. However, existing retroviral vectors, as well as other animal viruses used to deliver foreign genes [e.g., adenovirus, adeno-associated virus (AAV), etc] are not liver-specific with regard to either infection or expression.

The unusually efficient genome of HBV is a factor regarded by the art as a limitation on the ability to manipulate or engineer the HBV genome. Mutations, insertions or deletions in many regions of the HBV genome have deleterious effects on viral gene expression and replication [Beames and Lanford (1995) J. Virol. 69:6833; Faruqi et al. (1991) Virol. 183:764; Machein et al. (1992) Arch. Virol. [Suppl] 4:133; Melegari et al. (1994) Virol. 199:292; Nakatake et al. (1993) Virol. 95:305; and Radziwill et al. (1990), supra]. The tether region of the pol gene, however, seems to be manipulable or even dispensable. Computer sequence analysis shows that this region is located upstream of the preS1 gene and overlaps with the preS1 and preS2 regions [Faruqi et al. (1991), supra and Radziwill et al. (1990), supra]. Part of the tether region, however, does not overlap with any other HBV genes. A mutational analysis of the pol gene of HBV has demonstrated that up to 90 codons of the intervening tether sequence can be deleted without significant loss of the endogenous polymerase activity [Radziwill et al. (1990), supra]. It has also been shown that such a deletion has no effect on the RNA encapsidation process [Bartenschlager et al. (1990) J. Virol. 64:5324]. Mutants of HBV containing deletions in the preS1 region which overlaps the tether region are capable of replication [Melegari et al. (1994), supra]. The duck hepatitis B virus (DHBV) genome carrying the gene for protein A (369 bp encoding 123 amino acids) inserted in the tether region also retains the capability of expressing an active endogenous polymerase [Chang et al. (1990), supra]; this recombinant replication defective DHBV however did not direct the expression of functional protein A (i.e., no protein capable of binding to immunoglobulin G-Sepharose was detected in lysates of cells infected with this recombinant DHBV). This region, moreover, tolerates many mutations resulting in amino acid changes [Hirsch et al. (1990) Nature 344:552 and Li et al. (1989) J. Virol. 63:4965]. The tether region, therefore, seems to be dispensable for HBV replication and appears to be the most suitable site for manipulating the HBV genome. However, to date, the expression and functional activity of a foreign gene inserted in the tether region or in any other regions in the HBV genome has not been reported.

The present invention provides methods for the successful manipulation of the HBV genome to accommodate a foreign gene whose functional activity can be demonstrated in the context of the full length HBV genome in hepatoma cell lines. Recombinant HBV vectors containing the HIV-1 tat gene in the tether region were constructed (HBVtat recombinants). Transient expression in hepatoma cell cultures shows that the tat gene contained on these HBV vectors is expressed with functional activity. The HBVtat recombinant exhibits functional polymerase activity, albeit at a reduced level compared to the wild type HBV. The expression of other HBV genes and the capacity to form virus particles does not seem to be affected by the foreign gene insertion. The HBVtat recombinants of the present invention illustrate the production of replication competent HBV vectors capable of directing the functional expression of foreign gene sequences. The present invention also provides replication defective recombinant HBV vectors which may delivered to cells within viral particles (i.e., they may be packaged or encapsidated) or which may be delivered to cells via injection of the recombinant HBV DNA. Each category of recombinant HBV vectors is discussed below.

II. Construction of Recombinant HBV Vectors

The present invention provides recombinant HBV vectors which are capable of expressing functional heterologous gene products. The HBV recombinant vector may be designed so as to be replication competent or replication defective. The HBV recombinant vector may be capable of being packaged into infectious viral particles or may be a non-infectious virus. "Replication competent" viruses are capable of synthesizing additional copies of the viral genetic material. A replication competent virus need not be capable of producing infectious viral particles, although it may be capable of producing infectious viral particles. "Replication defective" viruses are incapable of synthesizing additional copies of the viral genome. Replication defective viruses may be encapsidated into infectious viral particles by providing in trans the viral proteins required to coat the viral genome with a mature viral particle. Infection of a cell with a replication defective recombinant viral vector will result in the transfer of the viral genome to the cell but will not result in the intracellular synthesis of the recombinant viral genome.

A. Replication Competent HBV Vectors

Replication competent recombinant HBV vectors contain heterologous gene sequences inserted into the tether region of HBV. The inserted heterologous sequences are inserted in such a manner that the reading frame for the pol gene and the surface antigen genes (preS1/preS2/S gene) is maintained. This type of vector illustrated herein by the construction of the recombinant HBVtat virus (Ex. 1). The HBVtat virus contains the HIV-1 tat gene in the tether region of HBV. This recombinant virus is replication competent, expresses functional Tat, functional pol activity, functional surface antigens and produces extracellular viral particles (Exs. 2–5). The production of functional pol activity, functional surface antigens and extracellular viral particles and the incorporation of nucleotides into the viral template (i.e., evidence of viral replication) is sufficient evidence to demonstrate the production of infectious recombinant viral particles. Direct demonstration of the production of infectious recombinant particles may be achieved using the protease treatment of extracellular recombinant viral particles and infection of a liver cell line as described in Example 6.

Replication competent HBV vectors can be delivered to liver cells via infection or by transfer of the recombinant viral DNA (e.g., injection of naked DNA, lipofection, electroporation, etc.). If the recombinant HBV vector is to be delivered to cells via infection, the size of the heterologous gene sequences must create a viral genome which does not exceed the packaging capacity; the maximum size of the insert should be less than or equal to about 700–800 bp.

Replication competent viruses which have a genome too large to be packaged (i.e., non-infectious recombinant viruses) may be delivered to the cell using any suitable gene transfer method (e.g., lipofection, electroporation, calcium phosphate-DNA coprecipitation, DEAE-dextran mediated transfection, injection, including microinjection, of DNA, etc.). If the recombinant non-infectious HBV vector is to be used for in vivo delivery of heterologous genes, direct injection of naked DNA into the liver of the recipient may be employed as described in Example 7. If the recombinant non-infectious HBV vector is to be used for ex vivo delivery of heterologous genes, any means of transferring DNA to cells known to the art may be employed.

B. Replication Defective HBV Vectors

The present invention also provides recombinant HBV vectors which are replication defective; these viruses contain deletions or alterations in the HBV sequences which renders the recombinant virus incapable of replication. Replication defective recombinant HBV may be encapsidated by providing in trans viral gene products such as pol and/or surface antigens which are not produced by the recombinant HBV vector. As long as the size of the recombinant HBV genome is within the packaging limit for the HBV particle, recombinant HBV particles will be produced.

The present invention provides replication defective HBV vectors in which the majority of the pol ORF has been deleted to permit the insertion of heterologous gene sequences up to about 2.2 kb in length. The total genome size of these recombinant HBV vectors is within the packaging limit of the HBV particle. Example 6 provides details for the construction of these viruses and methods for the packaging of the replication defective viral genomes for delivery via infection.

III. Expression of Functional Heterologous Genes in Recombinant HBV Vectors

The heterologous gene sequences inserted into the recombinant HBV vectors of the present invention may be expressed using either endogenous HBV promoters or enhancer/promoters or using heterologous promoters or enhancer/promoters.

A. Endogenous Viral Promoters

The transcription of the heterologous gene sequences contained within the recombinant HBV vectors of the present invention may be directed by an endogenous (i.e., an HBV) promoter. A number of endogenous promoters are present within the HBV genome; these promoters control the transcription of the viral genes. As described in the examples below, transcription of the heterologous gene sequences inserted into the tether region of the HBV pol gene is controlled by the preS1 promoter. The preS1 promoter (i.e., the TATA box) is located between nt 2784–2790 of SEQ ID NO:1 (the wild-type HBV adw2 genome). The location of other HBV promoters and enhancers (e.g., the core/pol promoter) is known to the art and these may be employed for the expression of heterologous gene sequences contained within the recombinant HBV vectors of the present invention.

B. Heterologous Promoters

The transcription of the heterologous gene sequences contained within the recombinant HBV vectors of the present invention may be directed by a heterologous promoter. When a heterologous promoter (or enhancer/promoter) is employed for the expression of the heterologous gene sequences, the heterologous promoter is placed in the same transcriptional orientation as the endogenous promoter(s) present on the recombinant HBV vector.

The heterologous promoter chosen will allow for high levels of transcription in the host cell (i.e., in liver cells). The expression of the heterologous gene sequences may be driven by a promoter or by an enhancer and promoter. Promoters and enhancers are short arrays of DNA which direct the transcription of a linked gene. While not intending to limit the invention to the use of any particular heterologous promoters and/or enhancer elements, the following are preferred promoter/enhancer elements as they direct high levels of expression of operably linked genes in a wide variety of cell types including liver cells.

i) The SV40 enhancer/promoter is very active in a wide variety of cell types from many mammalian species [Dijkema, R. et al., EMBO J., 4:761 (1985)]. The SV40 enhancer/promoter is available on a number of expression vectors [e.g., pZeoSV (Invitrogen)].

ii) The SRα enhancer promoter comprises the R-U5 sequences from the LTR of the human T-cell leukemia virus-1 (HTLV-1) and sequences from the SV40 enhancer/promoter [Takebe, Y. et al., Mol. Cell. Biol., 8:466 (1988)]. The HTLV-1 sequences are placed immediately downstream of the SV40 early promoter. These HTLV-1 sequences are located downstream of the transcriptional start site and are present as 5' nontranslated regions on the RNA transcript. The addition of the HTLV-1 sequences increases expression from the SV40 enhancer/promoter.

iii) The human cytomegalovirus (CMV) major immediate early gene (IE) enhancer/promoter is active in a broad range of cell types [Boshart, M. et al., Cell 41:521 (1985)]. The 293 cell line (ATCC CRL 1573) [J. Gen. Virol., 36:59 (1977), Virology 77:319 (1977) and Virology 86:10 (1978)], an adenovirus transformed human embryonic kidney cell line, is particularly advantageous as a host cell line for vectors containing the CMV enhancer/promoter as the adenovirus IE gene products increase the level of transcription from the CMV enhancer/promoter. The CMV-IE enhancer/promoter is available on a number of vectors [e.g., pcDNA I, pcDNA I/Amp, pCDM8 (all from Invitrogen)].

iv) The recombinant LTR whose sequence is provided in SEQ ID NO:16 is a Moloney murine leukemia LTR containing CMV-IE/HIV-1 TAR sequences. This recombinant LTR is very active in human liver cells [Robinson et al. (1995), supra].

v) The enhancer/promoter from the human elongation factor 1α gene is abundantly transcribed in a very broad range of cell types [Uetsuki, T. et al., J. Biol. Chem., 264:5791 (1989) and Mizushima, S. and Nagata, S., Nuc.

Acids. Res. 18:5322 (1990)]. The sequence of this enhancer/promoter is provided in SEQ ID NO:15.

vi) The promoter from the α-fetoprotein gene; this promoter is expressed at high levels in liver cells (e.g., hepatoma cells). Promoters and enhancer/promoters from other genes expressed at high levels in liver are suitable for use in the HBV vectors of the present invention.

vii) The enhancer/promoter from the Rous sarcoma virus (RSV) LTR. This enhancer/promoter is available on a number of expression vectors [e.g., pREP4, pREP7, pRc/RSV pEBVHis (all from Invitrogen)].

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); mol (moles); mmol (millimoles); μmol (micromoles); nmol (nanomoles); g (gravity); gm (grams); mg (milligrams); μg (micrograms); pg (picograms); L (liters); ml (milliliters); μl (microliters); cm (centimeters); mm (millimeters); μm (micrometers); nm (nanometers); hr (hour); min (minute); msec (millisecond); °C. (degrees Centigrade); AMP (adenosine 5'-monophosphate); cDNA (copy or complimentary DNA); DTT (dithiotheritol); ddH$_2$O (double distilled water); dNTP (deoxyribonucleotide triphosphate); rNTP (ribonucleotide triphosphate); ddNTP (dideoxyribonucleotide triphosphate); bp (base pair); kb (kilo base pair); TLC (thin layer chromatography); tRNA (transfer RNA); nt (nucleotide); VRC (vanadyl ribonucleoside complex); RNase (ribonuclease); DNase (deoxyribonuclease); poly A (polyriboadenylic acid); PBS (phosphate buffered saline); OD (optical density); HEPES (N-[2-Hydroxyethyl]piperazine-N-[2-ethanesulfonic acid]); HBS (HEPES buffered saline); SDS (sodium dodecyl sulfate); Tris-HCl (tris[Hydroxymethyl]aminomethane-hydrochloride); rpm (revolutions per minute); ligation buffer (50 mM Tris-HCl, 10 mM MgCl$_2$, 10 mM dithiothreitol, 25 μg/ml bovine serum albumin, and 26 μM NAD+, and pH 7.8); EGTA (ethylene glycol-bis(β-aminoethyl ether) N, N, N', N'-tetraacetic acid); EDTA (ethylenediaminetetracetic acid); ELISA (enzyme linked immunosorbant assay); LB (Luria-Bertani broth: 10 g tryptone, 5 g yeast extract, and 10 g NaCl per liter, pH adjusted to 7.5 with 1N NaOH); superbroth (12 g tryptone, 24 g yeast extract, 5 g glycerol, 3.8 g KH$_2$PO$_4$ and 12.5 g, K$_2$HPO$_4$ per liter); DMEM (Dulbecco's modified Eagle's medium); ABI (Applied Biosystems Inc., Foster City, Calif.); Amersham (Amersham Corporation, Arlington Heights, Ill.); ATCC (American Type Culture Collection, Rockville, MY); Beckman (Beckman Instruments Inc., Fullerton Calif.); BM (Boehringer Mannheim Biochemicals, Indianapolis, Ind.); Bio-101 (Bio-101, Vista, Calif.); BioRad (BioRad, Richmond, Calif.); Brinkmann (Brinkmann Instruments Inc. Wesbury, N.Y.); BRL, Gibco BRL and Life Technologies (Bethesda Research Laboratories, Life Technologies Inc., Gaithersburg, Md.); CRI (Collaborative Research Inc. Bedford, Mass.); Eastman Kodak (Eastman Kodak Co., Rochester, N.Y.); Eppendorf (Eppendorf, Eppendorf North America, Inc., Madison, Wis.); Falcon (Becton Dickenson Labware, Lincoln Park, N.J.); IBI (International Biotechnologies, Inc., New Haven, Conn.); ICN (ICN Biomedicals, Inc., Costa Mesa, Calif.); Invitrogen (Invitrogen, San Diego, Calif.); New Brunswick (New Brunswick Scientific Co. Inc., Edison, N.J.); NEB (New England BioLabs Inc., Beverly, Mass.); NEN (Du Pont NEN Products, Boston, Mass.); Nichols Institute Diagnostics (Nichols Institute Diagnostics, San Juan Capistrano, Calif.); Pharmacia (Pharmacia LKB Gaithersburg, Md.); Promega (Promega Corporation, Madison, Wis.); Stratagene (Stratagene Cloning Systems, La Jolla, Calif.); UVP (UVP, Inc., San Gabreil, Calif.); USB (United States Biochemical Corp., Cleveland, Ohio); and Whatman (Whatman Lab. Products Inc, Clifton, N.J.).

Unless otherwise indicated, all restriction enzymes were obtained from New England Biolabs and used according to the manufacturers directions. Unless otherwise indicated, synthetic oligonucleotides were synthesized using an ABI DNA synthesizer, Model No. 391.

EXAMPLE 1

Construction of a Recombinant HBV Vector

In order to investigate the ability to insert and express a foreign gene in the context of the HBV genome, the entire HIV-1 tat gene was inserted into the tether region of the pol gene. This construct and a number of intermediate constructs are described below.

a) Construction of pTHBV and pTHBVT-d

The full length genome (EcoRI-EcoRI) of HBV adw2 subtype was inserted into the pT7T318U vector (Pharmacia Biotech) which had been digested with EcoRI to create the plasmid pTHBV. pTHBV contains the entire HBV genome (subtype adw2). The DNA sequence of the HBV genome contained within pTHBV is listed in SEQ ID NO:1.

A replication competent plasmid for wild-type HBV was constructed by ligation of two head-to-tail copies of the full-length HBV (EcoRI-EcoRI) sequence into the pT7T3 18U vector. The resulting plasmid was termed pTHBV-d. The DNA sequence of pTHBV-d is listed in SEQ ID NO:2. In SEQ ID NO:2, the HBV sequences are located from nt 247 through nt 6688 inclusive; the remaining sequences are from the pT7T3 18U vector.

b) Construction of pTHBVT and pTHBVT-d

An HBVtat recombinant was initially constructed by insertion of the HIV-1 tat gene into the unique BstEII site in the tether region and in-frame with the pol ORF; this recombinant is contained on the plasmid pTHBVT which is shown schematically in FIG. 1A. In FIG. 1, all the ORFs encoded on the EcoRI-EcoRI monomer of the HBV genome (3221 bp) are shown with the positions of all initiation codons according to the adw2 subtype. The ORFs start from the blunt end and stop at the arrow end. The four domains of the pol gene corresponding to the functional activities are indicated [Faruqi et al. (1991) Virol. 183:764 and Robinson (1990) in *Hepadnaviridae and their replication*, Fields et al. eds., Fields Virology, Raven Press, Ltd. N.Y.] The solid vertical bar represents the preS1 promoter which is located 39 bp upstream of the tat insertion; the transcription initiation site of the preS1 RNA (2.4 kb) is indicated by an arrow. The NcoI site at the initiation codon of the X gene and the BspEI site downstream of the initiation codon of the pol gene are also shown. The following abbreviations are used in FIG. 1: "RT/Pol," reverse transcriptase and DNA polymerase; "TP," terminal protein.

To construct pTHBVT, a 267-base pair (bp) HIV-1 tat cDNA fragment with additional BstEII sites at both ends was amplified from plasmid pCEP-tat [Robinson et al. (1995) Gene Therapy 2:269] by PCR using the upstream primer 5'-TGCG GGTCACCAATGGAGCCAGTAGATCCTAAT-3' (SEQ ID NO:3) and the downstream primer 5'-ATAT GGTGACCCTTCCGTGGGCCCTGTCGGGTC-3' (SEQ ID NO:4) (the BstEII sites are underlined in each primer). The PCR was conducted using Pfu DNA polymerase (Stratagene), a DNA polymerase capable of proof-reading, was used to minimize the error rate of the polymerase. The PCR tat fragment was subcloned into the unique BstEII site in the pol ORF of the HBV genome contained within pTHBV. The resulting construct was designated pTHBVT. DNA sequencing was performed to confirm the presence of the expected sequence. The DNA sequence of pTHBVT is listed in SEQ ID NO:5. In SEQ ID NO:5, the HBV sequences are located from nt 247 through nt 3069 and 3337 through 3734; the tat sequences are located from nt 3070 through 3336; the remaining sequences are from the pT7T318U vector. The recombinant virus contained within pHBVT is referred to as HBVtat.

The tat insert present in pTHBVT contains the entire tat ORF with its own initiation codon but without a stop codon. This insertion was located 39 bp downstream from the preS1 promoter and did not interfere with the ORFs of the HBV structural genes.

A replication competent plasmid for the HBVtat virus was constructed by ligation of two head-to-tail copies of the HBVtat (EcoRI-EcoRI) sequence into the pT7T318U vector. The resulting plasmid was termed pTHBVT-d. The DNA sequence of pTHBVT-d is listed in SEQ ID NO:6. In SEQ ID NO:6, the HBV sequences are located from nt 247 through nt 3069, 3337 through 6557 and 6825 through 7222, ; the tat sequences are located from nt 3070 through 3336 and nt 6558 through 6824; the remaining sequences are from the pT7T318U vector.

Figure 1B:
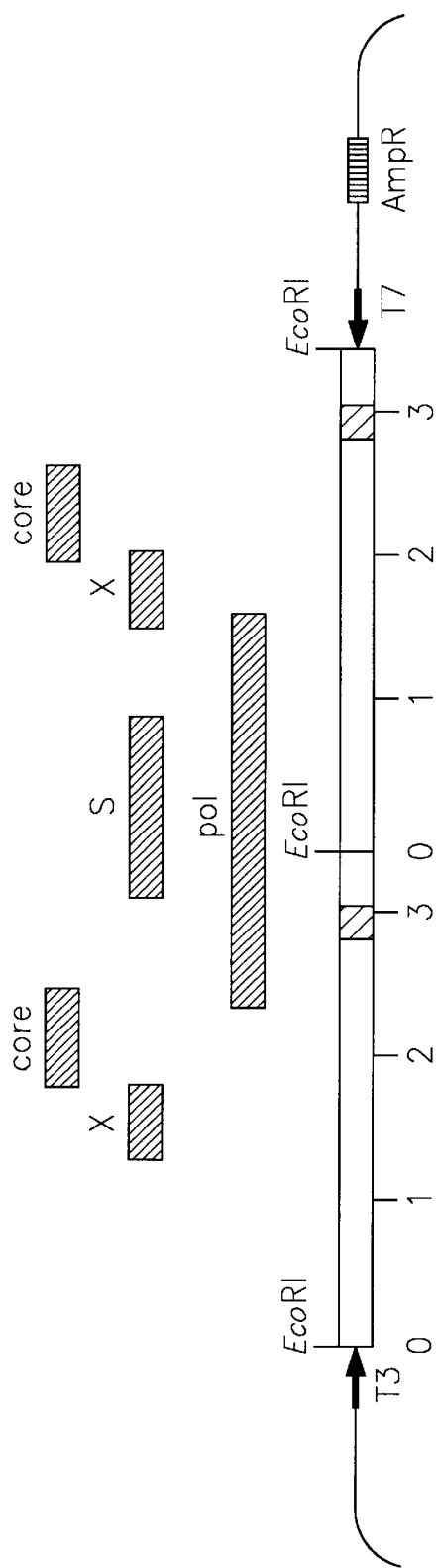
FIG. 1B is a schematic representation of the HBVtat virus (head to tail dimer form) as contained on pTHBVT-d.

FIG. 1B provides a schematic of pTHBVT-d. Expression of the HBV genes and the tat gene from this replicative plasmid (i.e., pTHBVT-d) was controlled by the HBV promoters. This dimeric construct was used to study the functions and characteristics of HBVtat.

In FIG. 1B, the linear map of the HBVtat replication competent plasmid (pTHBVT-d) (9859 bp) with two EcoRI-EcoRI monomers in a head to tail tandem configuration subcloned into the pT7T318U vector is shown. All ORFs are depicted by solid bars. The locations of the tat insertion are indicated by hatched boxes (diagonal hatch marks). The following abbreviations are used in FIG. 1B: "T3," T3 promoter; "T7," T7 promoter; "AmpR," ampicillin resistance. The arrowheads above T3 and T7 indicate the direction of transcription from these promoters.

c) Other Constructs

The plasmid pLTR-CAT [referred to as U3-R-CAT in Chang, L. -J. et al., J. Virol. 76:743 (1993)] is a reporter plasmid which contains the HIV-1 LTR directing the expression of the CAT gene.

The plasmid pCEP-tat contains the CMV-IE promoter directing the expression of the tat gene [Chang, L. -J. et al., J. Virol. 76:743 (1993)]. pCEP-tat was constructed as follows. pSP72tat (described below) was digested with XhoI and BamHI to isolate the tat gene. This XhoI/BamHI fragment was then inserted into either the eucaryotic expression vector pCEP4 (Invitrogen) to generate pCEP-tat. Pfu polymerase (Stratagene) was used in place of Taq DNA polymerase in the PCR because of its lower error rate. PCR conditions were as described above.

pSP72tat was made by cloning the tat gene into pSP72 (Promega). The tat gene was isolated using PCR from the plasmid pSV-tat [Peterlin, B. M. et al. Proc. Natl. Acad. Sci. USA 83:9734 (1986)]. The primers used to amplify the tat gene were 5'-AAGGATCCTCG AGCCACCATGGAGCCAGTAGATCCT-3' (SEQ ID NO:7) and 5'-CAAGATCTGCA TGCTAATCGAACG-GATC TGTC-3' (SEQ ID NO:8). Reaction conditions were as described [Chang, L. -J. et al. (1993) J. Virol. 67:743]. Briefly, Pfu polymerase (Stratagene) was used according to the manufacturer's instructions in a 50 µl reaction containing 0.5 µg of each primer, 0.01 µg of pSVtat [Peterlin, B. M. et al. (1986) Proc. Natl. Acad. Sci. USA 83:9734] for 30 cycles under the following conditions: step 1: 94° C. for 5 min; step 2: 50° C. for 1 min; step 3: 72° C. for 1 min; step 4: 92° C. for 1 min and step 5: repeat steps 2–4 for 30 cycles. Pfu DNA polymerase (Stratagene) was used in the PCR. The tat gene was recovered from the PCR products by digestion with BamHI and BglII and inserted into pSP72 (Promega) digested with BamHI and BglII to generate pSP72tat.

EXAMPLE 2

Functional Expression of HIV-1 tat by the HBVtat Recombinant Virus

The ability to express a foreign gene inserted into the HBV genome was investigated. The expression of the tat gene of HBVtat was determined by cotransfection of HBVtat and the HIV-1 LTR-CAT reporter plasmid, pLTR-CAT in HepG2 (human liver) and LMH (chicken liver) cells. The functional activity of the tat protein (Tat) was determined through transactivation of HIV-1 LTR using the CAT assay.

a) Tissue Culture and Cotransfection of HepG2 and LMH Cells

Human hepatoblastoma cells (HepG2; ATCC HB 8065) were cultured and maintained at 37° C. in 5% $CO_2$ in Auto-Pow MEM Eagle (modified) medium (ICN Biomedicals, Inc.) supplemented with 10 mM sodium bicarbonate, 2 mM L-glutamine, 10% fetal bovine serum, 50 units/ml penicillin G sodium, 0.01 mg/ml streptomycin and 50 units/ml nystatin (HepG2 medium). Chicken hepatoma cells [LMH; Condreay et al. (1990) J. Virol. 64:3249] were cultured and maintained at 37° C. in 5% $CO_2$ in a mixture of 1:1 Auto-Pow MEM Eagle (modified) (ICN Biomedicals, Inc.) and F12 (ICN Biomedicals, Inc.) media with the same supplementation as above for the HepG2 medium.

Transfection of HepG2 and LMH cells were performed in 60-mm tissue culture dishes by the Lipofectin procedure (GIBCO BRL, Life Technologies) as recommended by the manufacturer. A 1:6 ratio of DNA:Lipofectin was used for HepG2 transfection whereas a 1:3 ratio was used for LMH transfection. In brief, HepG2 or LMH cells were subcultured 20 hr prior to transfection. Cells were fed with fresh media 1 hr before transfection. The plasmid DNA and Lipofectin were each diluted into 300 µl of unsupplemented medium. These two solutions were combined, incubated for 30 min at room temperature, and then applied to cells that had been washed twice with the unsupplemented medium. The transfected cells were incubated at 37° C. in 5% $CO_2$. Four hours after transfection, an equal volume of the appropriate medium plus 10% fetal bovine serum (no supplementation with antibacterial agents) was added with further incubation. At 20 hr after transfection, the culture medium was changed to supplemented HepG2 or LMH medium.

For the CAT assay, a total amount of 5 µg of DNA per 60 mm tissue culture dish was used. HepG2 or LMH cells were transfected with the CAT reporter plasmid (pLTR-CAT) in the presence or absence of HBV plasmids or pCEP-tat.

The expression of HBV genes was assayed in HepG2 cells and a total amount of 10 µg of DNA per 60 mm tissue culture dish was used for transfection. Complementation of the hepatitis B surface antigens (HBsAg) was studied by cotransfecting an equimolar ratio of a plasmid producing HBsAg (pSV-45) with the HBVtat plasmid.

To assess transfection efficiency, all transfections were performed in the presence of human growth hormone plasmid pXGH5 (Nichols Institute Diagnostics). Each transfection included 0.1 μg of the pXGH5 plasmid which allows the transfected cells to express human growth hormone into the culture supernatant. Secreted human growth hormone was quantitated by radioimmunoassay using the commercially available kit provided by Nichols Institute Diagnostics. For preliminary detection and normalization of the expression of HBV genes, hepatitis B surface antigen (HBsAg) and hepatitis B e antigen (HBeAg) secreted in the cell media were determined by a Microparticle Enzyme Immunoassay (MEIA) (Abbott Laboratories).

b) CAT Assay

CAT assays were performed as described [Chang, L. -J. et al., (1993) J. Virol. 76:743]. Briefly, the transfected cells were harvested 48–72 hr after the addition of the DNA and cell lysates were prepared as follows. The cells were washed three times in PBS and subjected to three cycles of freeze-thawing in a 37° C. water bath and a dry-ice ethanol bath. The protein concentration in the cell lysates was determined by using a DC protein assay kit (BioRad). To obtain results within the linear kinetic range of CAT activity, the amount of cell lysate used in each reaction was adjusted to give a detectable signal within 1 hr and less than 60% consumption of the input substrate [$^{14}$C]chloramphenicol (0.5 μCi; 55 mCi/mmol; ICN). The enzyme concentration was determined by a serial dilution for lysates with high levels of CAT activity.

Following the incubation of the cell lysate and the substrate, the reaction products were spotted onto a TLC plate and chromatographed in a solution containing 95% chloroform and 5% methanol for 45 min. The plates were allowed to dry and then were autoradiographed by exposing the plates to photographic film for 12 hr at room temperature. The amount of chloramphenicol present in acetylated or non-acetylated forms was quantitated by exposing the TLC plates to an imaging plate for 2 hr and scanning with a phosphoimager (Model BAS 1000, Fuji Medical Systems, USA Inc.). The relative level of CAT enzyme was determined after normalization for transfection efficiency and total quantity of protein in each cell lysate.

c) Expression of HIV-1 tat in Cells Transfected With HBVtat

The expression of the tat gene of HBVtat was determined by cotransfection of HBVtat and the HIV-1 LTR-CAT reporter plasmid in HepG2 (human liver) and LMH (chicken liver) cells. The functional activity of the tat protein (Tat) was determined through transactivation of HIV-1 LTR using the CAT assay. A representative autoradiogram of a CAT assay performed on cell lysates prepared from cotransfected cells is shown in FIG. 2.

Figure 2:
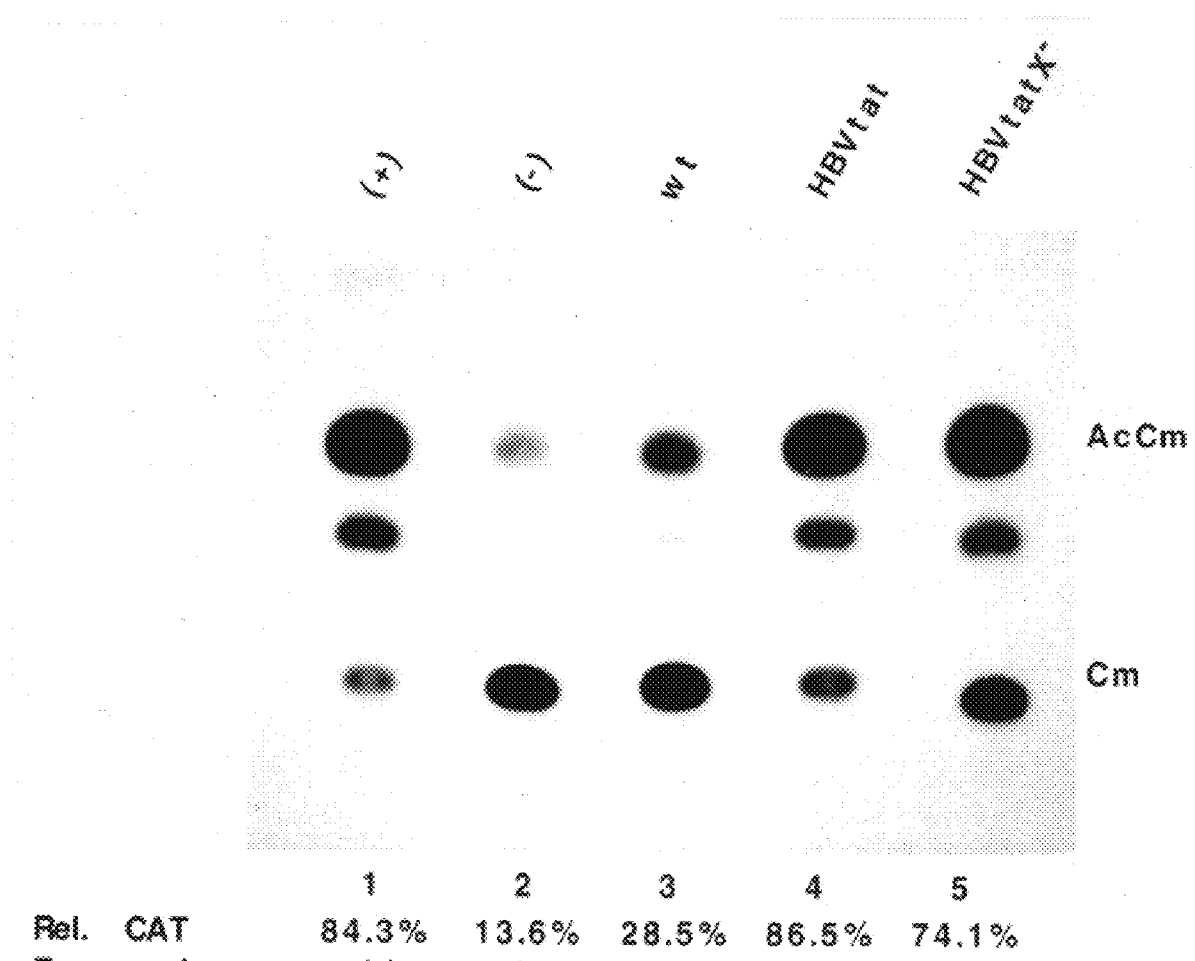
FIG. 2 is an autoradiograph of CAT assays which illustrate transactivation of the HIV-1 LTR by HBVtat in HepG2 cells.

In FIG. 2, lane 1 shows CAT activity in HepG2 cells transfected with pCEP-tat (positive control); lane 2 shows CAT activity in mock-transfected HepG2 cells (negative control; cells were cotransfected with pT7T318U and pLTR-CAT); lane 3 shows CAT activity in HepG2 cells cotransfected with pLTR-CAT and pTHBV-d ("wt", wild-type HBV); lane 4 shows CAT activity in HepG2 cells cotransfected with pLTR-CAT and pTHBVT-d (HBVtat) and lane 5 shows CAT activity in HepG2 cells cotransfected with pLTR-CAT and pTHBVTX$^-$-d (X$^-$ mutant of HBVtat; described in section d, below). The activity of the CAT enzyme expressed was determined 48 hr post-transfection. Relative levels of the CAT expression (normalized to an internal control human growth hormone) are shown as % product converted with standard deviations. The negative control represents the basal activity of the unactivated HIV-1 LTR. Elevated levels of the CAT enzyme activity reflect transactivation of HIV-1 LTR. The following abbreviation are used in FIG. 2: "AcCm," acetylated chloramphenicol; "Cm," unacetylated chloramphenicol.

The results shown in FIG. 2 demonstrate that in HepG2 cells, the basal activity of the CAT enzyme expressed from the HIV-1 LTR-CAT plasmid in the absence of Tat was low (FIG. 2, lane 2). However, when HBVtat was present, HIV-1 LTR was activated to a level similar to that activated by the Tat positive control (FIG. 2, lane 4 vs lane 1). These results illustrate the expression of functional Tat by the HBVtat recombinant.

The tat gene was also expressed and functioned in LMH cells but not as well as in HepG2 cells. The transactivation activity of HBVtat in these cells was about 40% of that of the Tat positive control. This suggests that HBV is not expressed as well in the chicken liver cells (LMH) as in the human liver cells (HepG2). Further studies of the HBVtat recombinant, therefore, were performed only in HepG2 cells.

Diminished expression of the tat gene controlled by the endogenous HBV promoter/enhancer elements in chicken hepatoma cells probably reflects the species and cell specificity of hepadnaviruses. It is known that HBV gene expression is regulated by liver specific promoter/enhancer elements [Schaller and Fischer (1991) Curr. Top. Microbiol. Imnuunol. 168:21 and Shaul (1991), Regulation of hepadnavirus transcription, A McLachlan (ed.), in *Molecular biology of hepatitis B viruses*, CRC Press, Boca Raton, Fla.]. Liver specific factor(s) has been shown to interact with the HBV enhancer [Patel et al. (1989) J. Virol. 63:5293] and to be essential for its activity [Jameel and Siddiqui (1986) Mol. Cell. Biol. 6:710]. Therefore, it is possible that the chicken LMH cells, although hepatocyte cells, may lack particular factor(s) required for regulating efficient expression of HBV genes. Evidence supporting tissue and species specificity of HBV is plentiful. It has been demonstrated that even though the HBV enhancer can function in a cell line derived from rat hepatocytes, the activity is only 30% of that expressed in human hepatoblastoma cells (HepG2) [Patel et al. (1989), supra]. In addition, DHBV replicates more efficiently in chicken hepatoma cells (LMH) than in human liver cells (HuH-7 and HepG2) [condreay et al. (1990) J. Virol. 64:3249].

d) Tat Expression from HBVtat is Responsible for Transactivation of the HIV-1 LTR Although the wild type HBV transactivated HIV-1 LTR to a lesser extent than did the HBVtat recombinant (FIG. 2, lane 3 vs lane 4), it was still possible that the transactivation function of HBVtat was enhanced by other HBV genes, such as the X gene [Siddiqui et al. (1989) Virol. 169:479 and Twu et al. (1990) Virol. 177:406]. To test this possibility, mutations of the X gene in HBVtat were constructed and used to cotransfect HepG2 cells (along with pLTR-CAT) as follows.

Mutation of the X gene of HBVtat was performed by site-directed PCR mutagenesis. Three oligonucleotide primers were designed. The upstream primer 5'-TT<u>ACTAGT</u>GCCATTTGTTCAGTGGTTCG-3' (SEQ ID NO:9) was homologous to the sequence at the unique SpeI site (underlined) located 142 bp upstream of the X gene. The downstream primer 5'-GTGCACA<u>CGGACCGG</u>CAGATG-3' (SEQ ID NO:10) anneals to the sequence at the unique RsrII site (underlined) located 197 bp downstream of the X gene. The mutagenic primer 5'-ATACATCGTTT<u>CC</u>cTGGCTGCTAGGCTGTACTGCtAACTGGATCCTTC-3' (SEQ ID NO:11 was targeted to the sequence at the unique NcoI site (underlined) at the initiation codon of the X gene with change from A to C at the 1376 nucleotide (nt) and from C to T at the 1397 nt (nt numbering according to sequence of the HBV genome as set forth in SEQ ID NO:1). These changes abolished the initiation codon of the X gene and the original NcoI site with addition of a stop codon (mutated nucleotides shown in boldface lower cases). These mutations conserved the pol coding sequences. The mutation was performed by multiple PCR as described [Picard et al. (1994) Nucleic Acids Res. 22:2587]. Briefly, mutagenesis was performed as a one-tube PCR with 3 consecutive steps each comprising 10 amplification cycles. In step 1, the mutagenic primer (SEQ ID NO:11) (10 pmol) and the downstream primer (SEQ ID NO:10) (10 pmol) were used to amplify a megaprimer using pTHBV as the template (3.6 fmol or 15 ng of the plasmid); the 95 μl PCR contained 2.5 units Pfu DNA polymerase, 0.2 mM all four dNTPs, 20 mM Tris-Cl, pH 8.75, 10 mM KCl, 10 mM $(NH_4)_2SO_4$, 2 mM $MgSO_4$, 0.1% Triton X-100 and 0.1 g/l BSA. The enzyme was added last and the reaction was overlaid with mineral oil. The reaction was started by incubation at 95° C. for 3 min. Ten amplification cycles consisting of 94° C., 1 min; 56° C., 1 min.; 72° C., 2 min. were performed followed by 5 min. at 72° C.; the reaction was then held at 4° C. In step 2, the upstream primer (SEQ ID NO:9) (50 pmol) was added to the above reaction to permit the synthesis of the mutated X gene using 10 amplification cycles as described above. In step 3, additional downstream primer (SEQ ID NO:10) (50 pmol) was added to permit further DNA amplification using 10 amplification cycles as described above.

The PCR fragment containing the mutated X gene sequences was then cut with SpeI and RsrII and cloned into the unique sites in the HBVtat plasmid. The resulting plasmid was termed pTHBVTX⁻; the sequence of pTHBVTX⁻ is provided in SEQ ID NO:12. In SEQ ID NO:12, the HBV sequences are located from nt 247 through nt 3069 and 3337 through 3734; the tat sequences are located from nt 3070 through 3336; the remaining sequences are from the pT7T318U vector.

HepG2 cells were cotransfected with pLTR-CAT (CAT reporter plasmid) and pTHBVTX⁻ (X⁻ mutant of HBVtat) and CAT assays were performed on cell lysates as described above. FIG. 2, lane 5 shows a representative CAT assay from cells cotransfected with pLTR-CAT and pTHBVTX⁻. As shown in FIG. 2, the X⁻ mutant of HBVtat (HBVtatX⁻) showed a only small reduction in the transactivation activity compared with that of the original HBVtat construct (FIG. 2, lane 5 vs lane 4). These results thus demonstrate that the major transactivation activity (86%) of HBVtat was accounted for by the tat insertion.

e) HBV Core, Pol and Surface Gene Products do not Transactivate the HIV-LTR

To see if HBV genes other than the X gene also contributed to the transactivation function, transient expression and the CAT assay of individual HBV genes were performed in HepG2 cells. Plasmids containing the core (pCHBVC), pol (pCHBVP), HBsAg (PSV-45), X (pSG-X) genes were obtained or constructed as follows.

To construct the HBV core expression plasmid, pCHBVC, a 1,500 nt fragment from the NlaIII site to the unique AvrII site which includes the entire sequence of the core gene was PCR-amplified from the HBV genome-containing plasmid, pKSVHBV1 [Seifer et al. (1990) Virol. 179:300] and cloned into the pTZ19R vector (Pharmacia). The sequence between the HindIII and XbaI sites containing the core gene was subcloned into the eukaryotic expression vector pcDNA-I/amp (Invitrogen) to generate pCHBVC.

The HBV pol plasmid (pCHBVP) was constructed by subcloning a 2,734 nt fragment containing the entire pol ORF from pKSVHBV1 into the pTZ19R vector by multiple cloning steps using restriction enzymes and PCR. The sequence coding for the entire HBV pol ORF was cut and subcloned into the HindIII/EcoRV sites of the eukaryotic expression vector pcDNAI/amp. The subcloned sequences of these recombinant plasmids were verified by restriction mapping and DNA sequencing. The sequence of pCHBVP is provided in SEQ ID NO:13. In SEQ ID NO:13, the pol ORF begins at nt 3095 and ends at nt 5632.

pSG-X was constructed by inserting the X gene contained within a ~600 bp NcoRI-BglII fragment together with a 113 bp EcoRI-NcoI fragment from the hygromycin gene [this fragment served as a stuffer fragment and may be obtained from the pCEP4 vector (Invitrogen)] into the EcoRI/BglII sites of the eukaryotic expression vector pSG5 (Stratagene).

The pSV45H plasmid carries the entire HBV surface antigen ORFs for the simultaneous expression of L, M and S surface proteins (i.e., the preS1, preS2 and S sequences) [Persing et al. (1986) Science 234:1388]. Expression of the surface antigen ORFs in pSV45H is under the transcriptional control of the SV40 promoter (i.e., a 342 bp PvuII-HindIII fragment of SV40). pSV45H was constructed as described by Persing et al., supra. Briefly, the unique BstEII site within the HBV genome (adw991 subtype) was converted into a BglII site by the addition of a BglII linker. The resulting genome was then digested with BglII and the 2.3 kb BglII fragment containing the entire preS region and the HBV polyadenylation signal (within the core gene) was inserted into pSV65 digested with BamHI. pSV65 contains 342 bp PvuII-HindIII fragment of SV40 (the promoter region) inserted into pSP65 (Promega).

Figure 3:
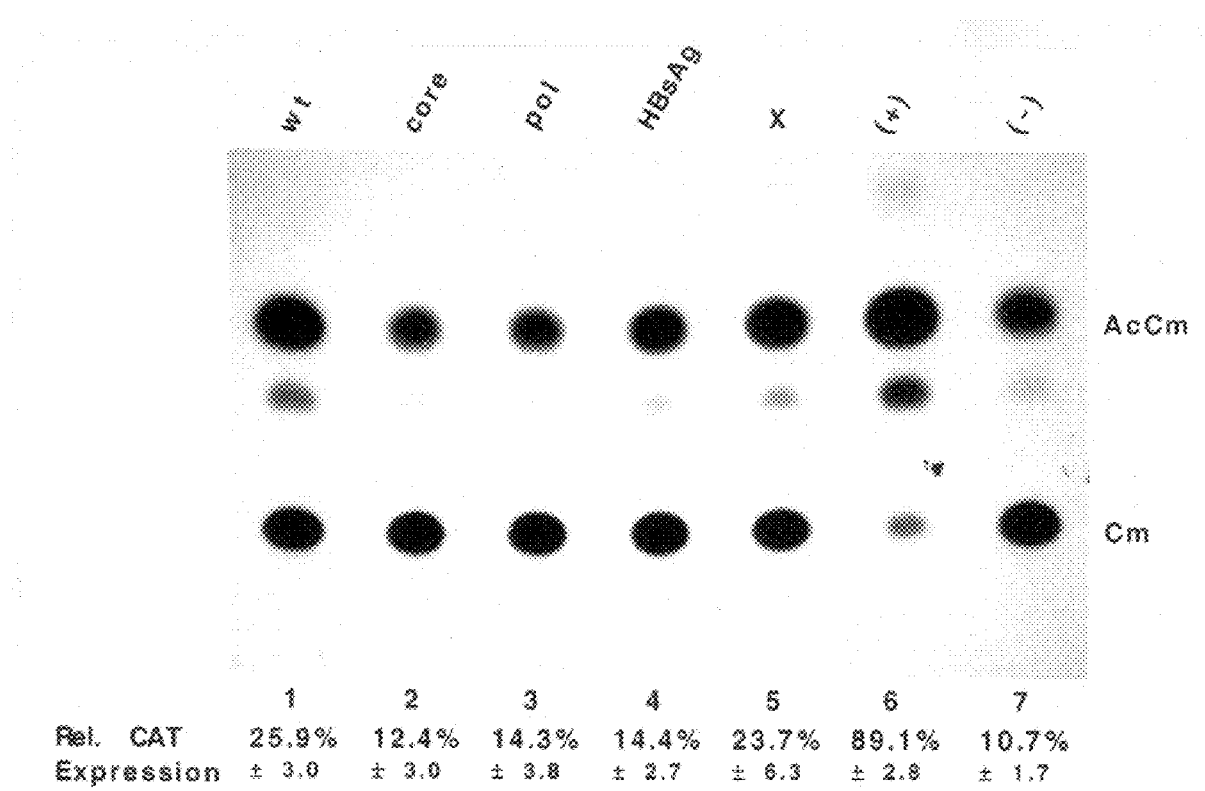
FIG. 3 is an autoradiograph of CAT assays which illustrate transactivation of the HIV-1 LTR by individual HBV gene products in HepG2 cells.

Each of the above plasmids expressing a single HBV gene were cotransfected with pLTR-CAT into HepG2 cells as described above. Cell lysates were prepared and CAT assays were conducted as described above. A representative autoradiograph is shown in FIG. 3. In FIG. 3, lanes 1–7 contain extracts from HepG2 cells cotransfected with pLTR-CAT and either pTHBV-d ("wt," wild-type HBV), pCHBVC ("core"), pCHBVP ("pol"), pSV45H ("HBsAg"), pSG-X ("X"), pCEP-tat ("+," positive control) or pT7T318U ("−," negative control). Relative levels of the CAT expression (normalized to an internal control human growth hormone) are shown as % product converted with standard deviations. The following abbreviation are used in FIG. 3: "AcCm," acetylated chloramphenicol; "Cm," unacetylated chloramphenicol.

The results shown in FIG. 3 indicate that the level of the transactivation of the X gene was as high as that of the wild type HBV, whereas the transactivation activities of the core, pol or surface genes were insignificant.

EXAMPLE 3

Expression of the tat Gene in HBVTat is Controlled by the preS1 Promoter

Although the tat insert was designed to be expressed as a pol-Tat fusion recombinant using the core/pol promoter, the tat ORF was also proximal to the preS1 promoter (FIG. 1A). It was thus possible that the tat gene might be expressed by the preS1 promoter. To determine which promoter was used for the expression of the tat gene in HBVtat, a frameshift mutation was generated near the beginning of the pol gene in HBVtat as follows.

Figure 1C:
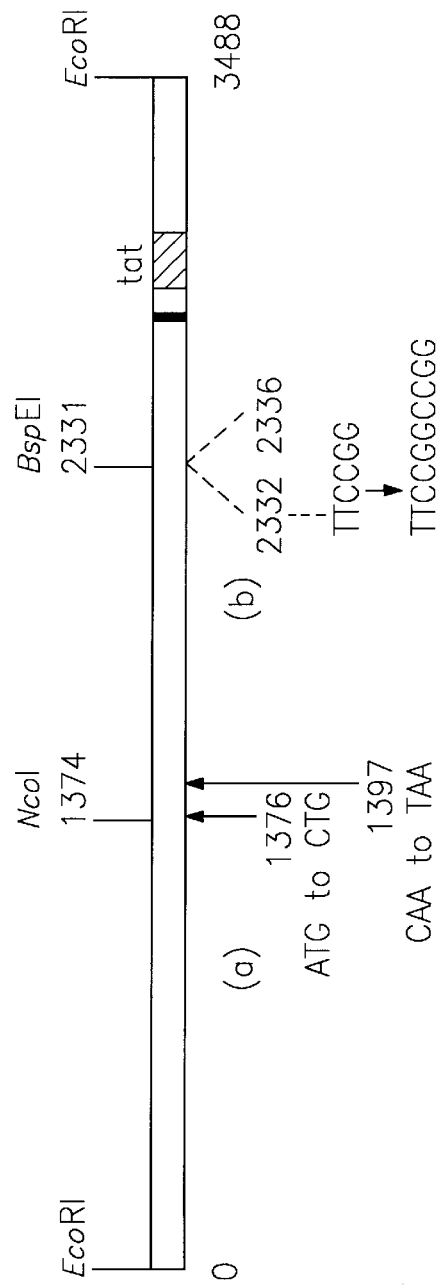
FIG. 1C schematic representation of mutant HBVtat viruses which shows the location of the mutations introduced into the X gene (a) and the frameshift mutation introduced into the pol ORF (b).

A frameshift mutation of the pol ORF of HBVtat was generated by digesting pTHBVT with BspEI site (a unique site located at position 2331 nt of the HBV genome) downstream of the initiation codon of the pol gene and subsequently filling in (2332 to 2336 nt) with Klenow Fragment (GIBCO BRL, Life Technologies). The resulting plasmid was termed pTHBVTP⁻. The DNA sequence of pTHBVTP⁻ is provided in SEQ ID NO:14. In SEQ ID NO:14, the HBV sequences are located from nt 247 through nt 3073 and 3341 through 3737; the tat sequences are located from nt 3074 through 3340; the remaining sequences are from the pT7T318U vector.

pTHBVTP⁻ is shown schematically in FIG. 1C. A plasmid containing a head to tail dimer of the HBV genome present in pTHBVTP⁻ was generated as described in Example 1 (i.e., an EcoRI-EcoRI dimer) and the resulting plasmid was termed pTHBVTP⁻-d and the virus produced by this construct is referred to as HBVtatP⁻.

FIG. 1C (b) diagrams the mutation present in pTHBVTP⁻. The dotted lines indicate the frameshift mutation in the pol ORF by digestion of the BspEI site and filling in at 2332 to 2336 nt. The inserted nucleotides are shown as boldface letters.

The mutation present in pTHBVTP⁻ disrupted the reading frame of the pol gene. It, therefore, ablated the expression of the tat insert as a pol-Tat fusion recombinant. These mutated sites were verified by restriction mapping and DNA sequencing. The pTHBVTP⁻-d and pLTR-CAT plasmids were cotransfected into HepG2 cells to examine the effect of the frameshift mutation in the pol ORF. Cotransfections were conducted as described in Example 2. A representative autoradiograph of CAT assays run using cell lysates from cotransfected HepG2 cells is shown in FIG. 4.

Figure 4:
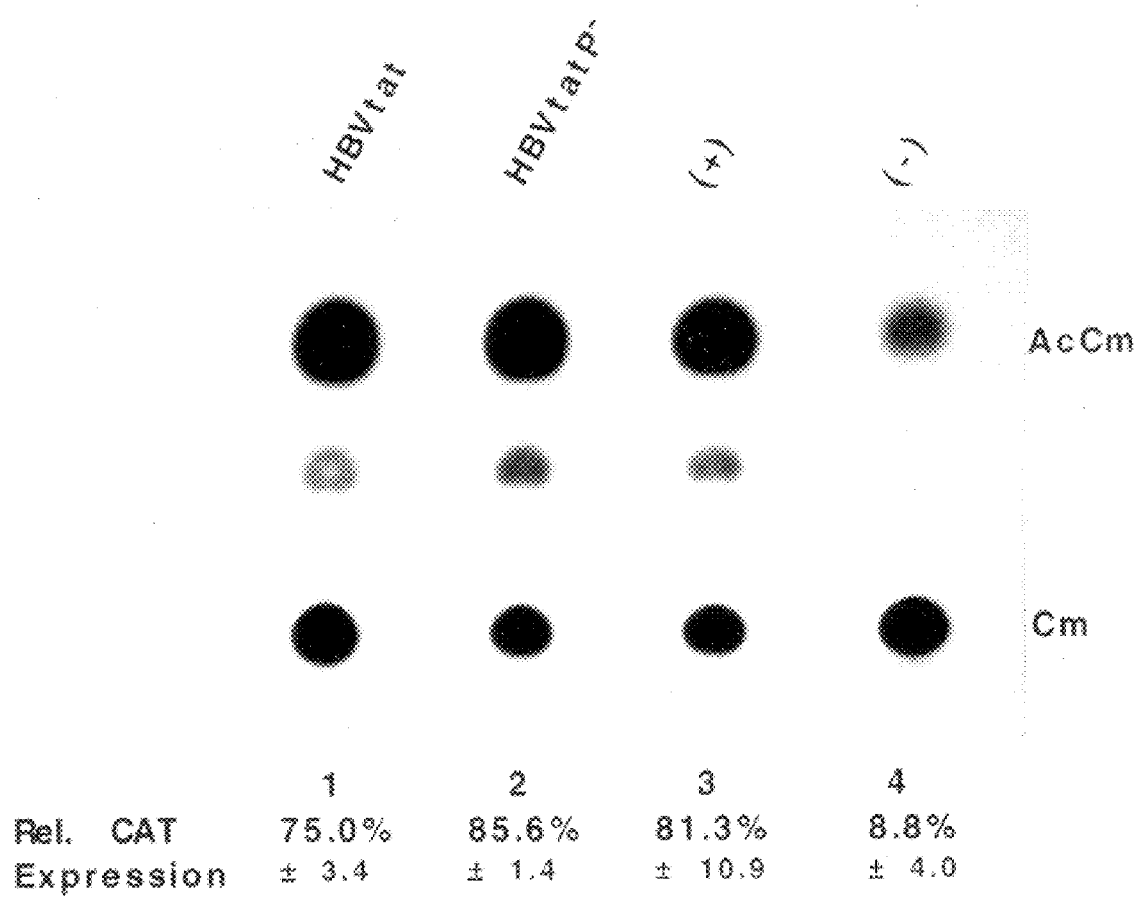
FIG. 4 is an autoradiograph of CAT assays which illustrate transactivation of the HIV-1 LTR by the pol mutant of HBVtat in HepG2 cells.

In FIG. 4, lanes 1 and 2 depict CAT activity present in cells cotransfected with pLTR-CAT and pTHBVT-d (HBVtat) or pTHBVTP⁻-d (HBVtatP⁻), respectively. Lanes 3 and 4 depict CAT activity from cells transfected with pCEP-tat ("+," positive control) and pT7T318U ("-," negative control), respectively. Relative levels of the CAT expression (normalized to an internal control human growth hormone) are shown as % product converted with standard deviations. The following abbreviation are used in FIG. 4: "AcCm," acetylated chloramphenicol; "Cm," unacetylated chloramphenicol.

The frameshift mutation present in HBVtatP⁻ disrupted the translation of the pol ORF, thus abolishing the expression of the tat gene as a pol-Tat fusion recombinant. Transient expression in HepG2 cells and the CAT assay showed that the pol frameshift mutant of HBVtat (i e., HBVtatP⁻) exhibited a transactivation function similar to that of the original HBVtat construct (FIG. 4, lane 1 vs lane 2). This result indicated that although the tat gene was in-frame with the pol ORF, the transactivation function of HBVtat was not dependent on the expression of the pol-Tat fusion recombinant. It also suggested that the expression of functional Tat was likely controlled by other mechanisms, such as the use of the preS1 promoter or internal translation initiation.

To determine whether the tat gene was expressed by the preS1 promoter, a Northern blot analysis of RNA expressed from HBVtat was performed. It was expected that the pregenomic RNA for HBVtat expressed by the core/pol promoter should be about 270 bases longer than that expressed from the wild type HBV in accordance with the size of the tat insertion. If a tat transcript was expressed by the preS1 promoter, the size of this subgenomic RNA should also be increased by about 270 bases. The sizes of the preS2/S and the X messages for the HBVtat construct would expected to be the same as those for the wild type HBV.

HepG2 cells were transfected with wild-type HBV (pTHBV-d), HBVtat (pTHBVT-d), pCEP-tat (positive control) and pT7T318U (negative control) as described in Example 2; a total of 10 μg of DNA per 60 mm tissue culture dish was used per transfection. Total RNA was isolated from the transfected cells 72 hours after transfection using TRIzol™ reagent (GIBCO BRL, Life Technologies) as described by the manufacturer. The amount of total RNA was determined by spectrophotometry. An equal amount of RNA for each sample was separated on a 1.2% agarose-0.22M formaldehyde gel as described [Tsang et al. (1993) BioTechniques 14:380]. The RNA was transferred to a Hybond-N membrane (Amersham) and hybridized with a $^{32}$P-HBV DNA probe. The same blot was stripped by washing in a boiling 0.5% SDS solution as described by the membrane manufacturer and rehybridized with a $^{32}$P-tat DNA probe using standard methods [Sambrook et al. (1989) *Molecular Cloning: A Laboratory Manual*, Cold Spring Harbor Laboratory Press, Cold Spring Harbor, N.Y.]. The resulting autoradiographs are shown in FIG. 5.

Figures 5A, 5B:
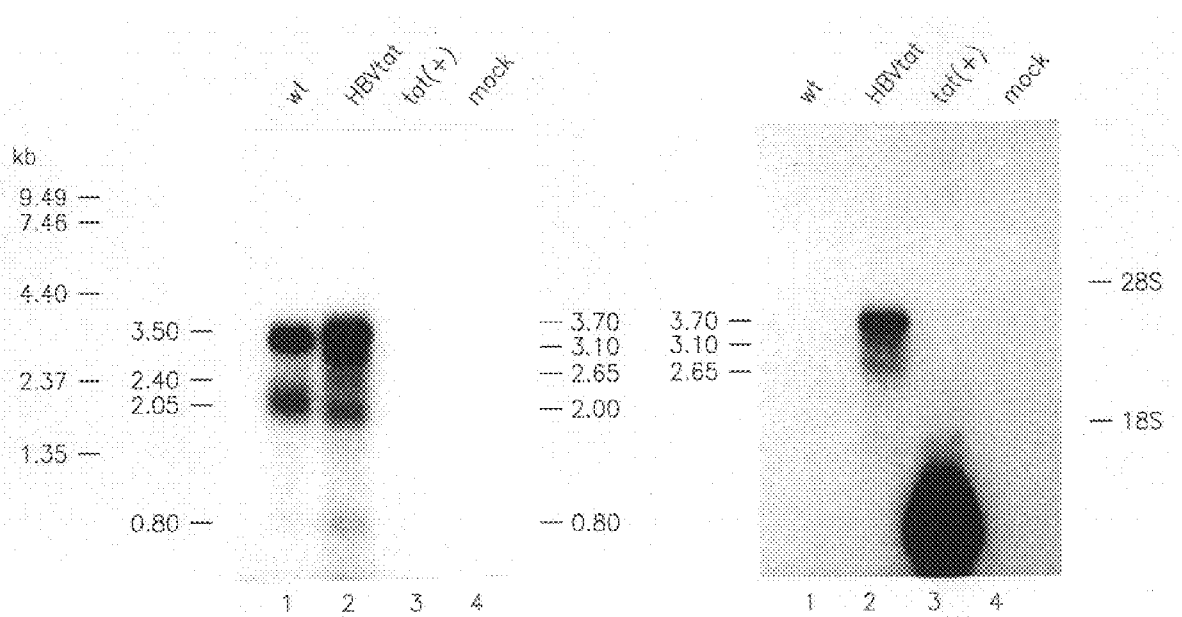
FIG. 5A is an autoradiograph of a Northern blot performed to detect RNA expressed from HBVtat in transfected HepG2 cells (HBV DNA used as probe).
FIG. 5B is autoradiograph of a Northern blot performed to detect RNA expressed from HBVtat in transfected HepG2 cells (tat DNA used as probe).

In FIG. 5, total RNA from HepG2 cells transfected with wild type HBV (lane 1, "wt"), HBVtat (lane 2), pCEP-tat as a positive control for the tat gene expression (lane 3, "tat(+)") and pT7T318U as a negative control (lane 4, "mock") was fractionated, transferred and hybridized with either the $^{32}$P-HBV DNA probe (FIG. 5A) or the $^{32}$P-tat DNA probe (FIG. 5B). Sizes of the transcripts expressed from the cells transfected with wild type HBV and HBVtat that contain the HBV sequences are shown on the left and right, respectively.

The Northern blot (FIG. 5) showed that five species of RNA expressed from HBVtat, 3.70, 3.10, 2.65, 2.00 and 0.80 kb in length, were detected using the HBV probe (FIG. 5A, lane 2) and four species of RNA, 3.50, 2.40, 2.05 and 0.80 kb in length, were detected from the wild type HBV (FIG. 5A, lane 1). Only three species of the RNA transcripts expressed from HBVtat, 3.70, 3.10 and 2.65 kb in length, were detected by the tat probe (FIG. 5B, lane 2). These results indicated that the tat insert was expressed by the core/pol promoter and by the preS1 promoter since the pregenomic RNA (3.70 kb) and the subgenomic RNA (2.65 kb) for HBVtat were about 250 bases larger than expected for the wild type HBV. It appears that the tat gene was also expressed in another RNA species of about 3.10 kb in length. Because of its size, it is presumed that this tat transcript may be derived from the pregenomic RNA.

Taken together, these data demonstrate that the expression of functional Tat from HBVtat is controlled by the preS1 promoter. The above data also demonstrated that the tat gene inserted in the tether region is expressed by two promoters: the core/pol promoter and the preS1 promoter. Since the pol-Tat fusion recombinant expressed by the core/pol promoter is not responsible for the transactivation activity of HBVtat, the functional Tat appears to be expressed by the preS1 promoter as a Tat-pol fusion product. It is known that the tat protein functions in the nucleus and that the pol protein interacts with the 5'epsilon sequence of the pregenomic RNA and is encapsidated into core particles in the cytoplasm [Hirsch et al. (1991) J. Virol. 65:3309 and Junker-Neipmann et al. (1990) EMBO J. 9:3389]. While not limiting the present invention to any particular mechanism, it is conceivable that the pol-Tat fusion protein is encapsidated into core particles in the cytoplasm and thus is not transported into the nucleus where the tat protein would function. The data presented above showing that the pol-Tat fusion protein does not contribute to the Tat function is consistent with this hypothesis. Since the entire sequence of the pol protein is required for the encapsidation and packaging of cytoplasmic viral core particles [Bartenschlager et al. (1990) J. Virol. 64:5324 and Hirsch et al. (1990) Nature 344:552], the Tat-pol fusion recombinant lacking the terminal protein domain of pol would not be incorporated into core particles. Therefore, this Tat form may migrate to the nucleus. The above data support the conclusion that the functional Tat-pol fusion recombinant is expressed by the preS1 promoter because a RNA transcript of increased size relative to the preS1 RNA and attributable to the tat insertion has been detected. Alternatively, expression of this fusion protein by internal initiation at the tat initiation codon in the pregenomic RNA is also possible.

As shown above, the tat gene of HBVtat is also expressed as a 3.1 kb RNA and this RNA species is not detected from the expression of wild type HBV. The insertion of the tat gene into the HBV genome possibly induces the formation of this RNA species. In accordance with its size, this tat RNA species possibly originates from the pregenomic RNA. Since RNA splicing has been reported in hepadnaviruses [Hantz et al. (1992) Virol. 190:193; Obert et al. (1996) EMBO J. 15:2565; and Wu et al. (1991) J. Virol. 65:1680] and sequence analysis of HBVtat reveals consensus splice donor sites on the HBV genome flanking the tat insert and a consensus splice acceptor site and a branch point within the tat sequence. While not limiting the present invention to any particular mechanism, it is thought that this tat transcript is derived from splicing of the pregenomic RNA of the HBVtat recombinant.

Regardless of the exact mechanism by which Tat is produced in the recombinant HBV, the above data demonstrate for the first time the ability to express foreign gene sequences in the context of the HBV genome.

EXAMPLE 4

HBV Genome With HIV-1 tat Insertion Retains Endogenous Polymerase Activity

To examine the effect of the tat insertion in the HBV genome on viral gene expression and function, HBVtat was transiently expressed in HepG2 cells. The viral DNA polymerase activity was examined by endogenous polymerase assay and the ability to incorporate radioactively-labeled deoxynucleotides into the viral genome by core-associated DNA polymerase was examined. In addition, cytoplasmic lysates and culture media containing intracellular core and extracellular viral particles, respectively, were harvested from HepG2 cells transfected with wild type HBV or HBVtat and examined for the presence of relaxed circular and linear double stranded viral genome and single stranded DNA.

a) Transfection of HepG2 Cells and Endogenous Polymerase Assay of HBVtat

HepG2 cells were transfected with wild-type HBV (pTHBV-d), HBVtat (pTHBVT-d), a mock control (pT7T318U); transfections were conducted as described in Example 2. HepG2 cells were also cotransfected with either wild-type HBV or HBVtat and the HBsAg plasmid, pSV45H. For the cotransfections, an equimolar ration of the pSV45H and HBVtat plasmids were used (total amount of DNA was 10 μg/60 mm dish). Transfection efficiency was assessed by performing all transfections in the presence of pXGH5 (human growth hormone plasmid) and secreted growth hormone was quantitated by radioimmunoassay as described in Example 2. For preliminary detection and normalization of the expression of HBV genes, hepatitis B surface antigen (HBsAg) and hepatitis B e antigen (HBeAg) secreted in the cell media were determined by MEIA (Abbott Laboratories).

i) Isolation of Extracellular HBV Particles

Four to five days after transfection, the culture media from transfected cells were collected and centrifuged in a Sorvall RT6000B Refrigerated Centrifuge (Dupont) at 5,000 rpm for 10 min to remove cellular debris. The extracellular viral particles were pelleted over a 25% sucrose cushion in 50 mM Tris (pH 8.0), 150 mM NaCl and 10 mM EDTA solution using an ultracentrifuge SW 41 rotor (Beckman) at 30,000 rpm for 7 to 20 hr. The pellets were resuspended in 50 mM Tris (pH 7.5), 150 mM NaCl and 10 mM EDTA. To remove DNA not present in virus particles, 6 mM $MgCl_2$ and 100 μg/ml of DNase I were added to the suspension with incubation at 37° C. for 30 min. The virus particles were precipitated by addition of one-third volume of 26% PEG 8000, 1.4M NaCl, and 25 mM EDTA. After centrifugation, the pellets were suspended in the following solutions as appropriate. For endogenous polymerase assay, the pellets were suspended in 30 μl of polymerase buffer (50 mM Tris pH 8.0, 40 mM $MgCl_2$, 50 mM NaCl, 1% Nonidet P-40 and 0.3% β-mercaptoethanol). The pellets were suspended in 50 mM Tris (pH 7.5), 150 mM NaCl and 10 mM EDTA for DNA extraction and southern blot analysis.

ii) Isolation of Intracellular HBV Core Particles

Transfected HepG2 cells in 60 mm tissue culture dishes were lysed by addition of lysis buffer (10 mM Tris-HCl [pH 7.5], 50 mM NaCl, 1 mM EDTA, 0.25% Nonidet P-40, and 8% sucrose) and incubated for 2–5 min at room temperature. The cell lysate was collected and subjected to microcentrifugation to remove nuclei and cellular debris. To eliminate transfected plasmids and cytoplasmic RNA, the lysate was incubated with 6 mM $MgCl_2$, 100 μg/ml of DNase I, and 10 μg/ml of RNase A at 37° C. for 30 min. The viral core particles were precipitated by addition of one-third volume of 26% PEG 8000, 1.4M NaCl, and 25 mM EDTA followed by centrifugation. The pellets were then suspended in appropriate solutions as described above.

iii) Endogenous Polymerase Assay

Viral materials pelleted from culture media or cell lysates were suspended in 30 μl polymerase buffer. To the mixture, were added 11 μM of each of dATP, dGTP, and dTTP and 10 μCi of [α-$^{32}$P] dCTP (3,000 Ci/mmol; Amersham). The reaction was performed at 37° C. for 1 hr. Chase buffer containing 0.2 mM unlabeled dCTP, and 0.1 mM of each of dATP, dGTP, and dTTP were then added with further incubation for 30 min. The reaction was stopped by addition of sodium dodecyl sulfate (SDS) and proteinase K to final concentrations of 1% and 1 μg/μl, respectively, and incubated at 37° C. for at least 2 hr. The $^{32}$P-labeled viral DNA was isolated by phenol-chloroform extraction and ethanol precipitation. The labeled viral DNA was then electrophoresed through a 1.2% agarose gel. The $^{32}$P-labeled viral DNA was then transferred to a nylon membrane and analyzed by autoradiography. The relative level of the endogenous polymerase activity was analyzed using a phosphoimager.

b) Extraction of Viral DNA and Southern Blot Analysis

Viral materials pelleted from culture media or cell lysates were suspended in 50 mM Tris (pH 7.5), 150 mM NaCl and 10 mM EDTA. Nucleic acids were then purified by proteinase K digestion and phenol-chloroform extraction, and collected by ethanol precipitation. Viral DNA was assayed by agarose gel electrophoresis and Southern blot analysis using standard methods (Sambrook et al., supra).

The results of the endogenous polymerase assay conducted using extracellular HBV particles collected from HepG2 cells transfected with HBVtat demonstrated that radioactively-labeled deoxynucleotides could be incorporated into the viral genome by core-associated DNA polymerase. Cytoplasmic lysates and culture media containing intracellular core and extracellular viral particles, respectively, were harvested from HepG2 cells transfected with wild type HBV or HBVtat. The samples were normalized to the internal transfection control (secreted human growth hormone) and to the amounts of HBsAg and HBeAg secreted into the culture media. The reaction products were separated on 1.0% agarose gels and detected by autoradiography as shown in FIG. 6A.

Figures 6A, 6B:
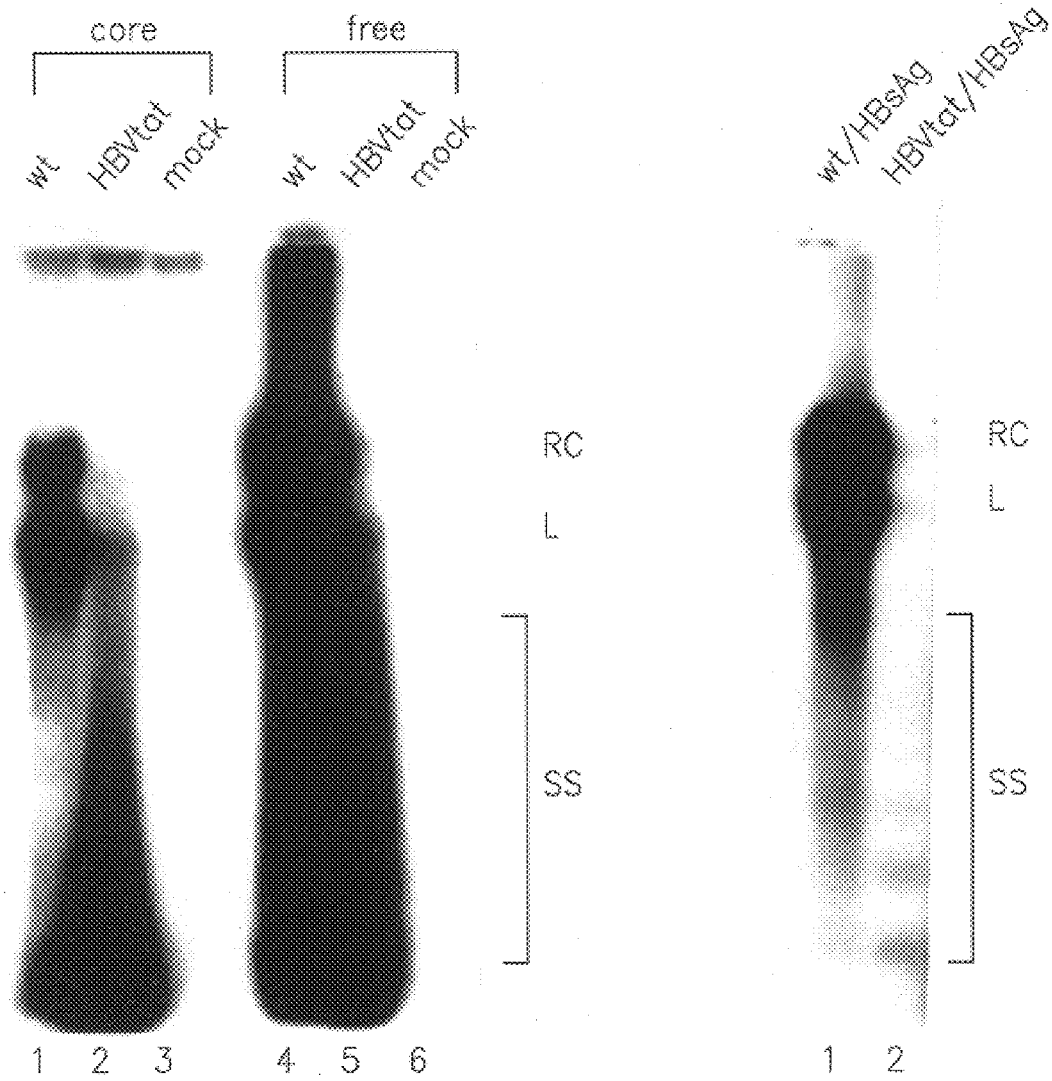
FIG. 6A is an autoradiograph showing endogenous polymerase activities in intracellular core particles and extracellular viral particles of HBVtat as compared to wild-type HBV.
FIG. 6B is an autoradiograph showing the endogenous polymerase activity of HBVtat complemented with HBsAg (L, M and S).

For the results shown in FIG. 6A, the viral core particles and cell-free particles were isolated from the transfected HepG2 cells and the culture media, respectively, 4–5 days post-transfection. Approximately equal amounts of core particles and extracellular viral particles were used after normalizing to an internal control human growth hormone secreted and to quantities of HBsAg and HBeAg produced. FIG. 6A shows the endogenous polymerase activities in intracellular core particles (lanes 1–3) and in extracellular viral particles (lanes 4–6) of HBVtat compared with wild type HBV. Lane 2 and lane 5, HBVtat; Lane 1 and lane 4, wild type HBV; Lane 3 and lane 6, mock transfection.

As shown in FIG. 6A, labeled DNA bands, corresponding to relaxed circular and linear double stranded viral genome and single stranded DNA, were detected, albeit at reduced levels, as a result of the DNA polymerase activity of HBVtat (FIG. 6A, lane 2 and 5), thus indicating that HBV with the tat insert (HBVtat) retained the polymerase function. The average level of endogenous polymerase activity in the intracellular core particles of HBVtat measured by phosphoimager was about 15% of that of wild type HBV and that in the extracellular viral particles of HBVtat was about 8% of that of wild type HBV. Southern blot analysis of the DNA isolated from the intracellular core and extracellular viral particles of HBVtat confirmed these results. Thus, the insertion of the 267 bp tat gene within the tether region of the pol gene reduced but did not abolish the polymerase function.

Previous studies have established that the L protein is absolutely required for the formation and secretion of HBV free virus particles [Bruss and Ganem (1991) Proc. Natl. Acad. Sci. USA 88:1059 and Sheu and Lo (1995) Gene 160:179]. While not limiting the present invention to any particular mechanism, a possible cause of the marked reduction in the endogenous polymerase activity of cell-free HBVtat particles may be, therefore, interference with expression of the L protein, because the insertion between the initiation codon and the promoter of preS1 gene might interrupt the expression of the L protein. To test this possibility, HepG2 cells were cotransfected with HBVtat and a plasmid carrying the entire HBsAg gene (pSV45H) to complement the HBsAg in trans. HepG2 cells were also cotransfected with the wild-type HBV and pSV45H. The extracellular viral particles were isolated from the cotransfected cultures and tested for endogenous polymerase activity as described above. A representative result of this analysis is shown in FIG. 6B.

FIG. 6B shows the endogenous polymerase activity of HBVtat complemented with HBsAg (L, M and S). An equal molar ratio of HBVtat and the HBsAg plasmid were cotransfected and transiently expressed in HepG2 cells as described above. The extracellular viral particles were harvested and analyzed for the endogenous polymerase activity. Lane 2, HBVtat complemented with HBsAg; Lane 1, wild type HBV complemented with HBsAg. RC, relaxed circular; L, linear; SS, single stranded.

As seen in FIG. 6B, complementation of HBsAg did not seem to improve the endogenous polymerase activity of HBVtat. The ratio of the endogenous polymerase activities of the trans-complemented HBVtat to those of the wild type HBV was as high as the ratio without L complementation. These results suggest that the reduction in the HBVtat polymerase activity was not due to a reduction in the L protein synthesis.

The results presented above demonstrate that insertion of the tat gene in-frame with the pol gene reduces the endogenous polymerase activity of the pol protein. The reduction of the endogenous polymerase activity in the extracellular free virus particles was greater than that detected in the intracellular core particles. This suggested that the tat insertion might interfere with the L protein synthesis and thus affect the secretion of the free virus particles. The HBsAg complementation experiment described above, however, did not support this hypothesis; that is, the complementation did not increase the endogenous polymerase activity in the recombinant cell-free viral particles. While not limiting the present invention to any particular theory, it is possible that insertion of the foreign gene in-frame with the pol gene has a direct effect on the function of the polymerase enzyme. The insertion may influence the structural conformation of the pol protein and thus result in a reduced enzymatic activity. Attempted trans-complementation with wild-type pol protein did not show significant increase in the endogenous polymerase activity of HBVtat. This was not unexpected since it is known that the pol protein acts primarily in cis for encapsidation and packaging of pregenomic RNA; that is, pregenomic RNAs from which the pol protein is synthesized are preferentially encapsidated [Bartenschlager et al. (1990), supra and Hirsch et al. (1990), supra].

EXAMPLE 5

The Insertion of tat has no Significant Effect on the Expression of other HBV Genes Similar levels of HBeAg and HBsAg were detected in the culture media of cells transfected with HBVtat and wild type HBV at the same transfection efficiency (Table 1). For the results shown in Table 1, HepG2 cells were transfected and HBsAg and HBeAg secreted into the culture medium was quantitated using the MEIA assay as described in Example 4. Furthermore, the detection of endogenous polymerase activity of the extracellular viral particles of HBVtat indicated that HBVtat could form complete virus particles. The insertion of the HIV-1 tat gene into the HBV genome, therefore, does not appear to abrogate the expression of HBV genes or the capability of forming and secreting extracellular virions.

TABLE 1

Detection Of HBsAg And HBeAg Produced By HepG2 Cells Transfected With Wild Type HBV And HBVtat

| | Amounts (S/N$^b$ ± Standard Deviation) | |
|---|---|---|
| Samples$^a$ | HBsAg | HBeAg |
| wt HBV | 56.03 ± 27.35 | 249.18 ± 65.29 |
| HBVtat | 60.06 ± 13.83 | 226.56 ± 85.76 |
| mock | 1.20 ± 0.04 | 1.18 ± 0.05 |

$^a$Samples were culture media of HepG2 cells transfected with wild-type HBV, HBVtat or mock (pT7T318U) and were assayed for HBsAg and HBeAg by MEIA.

TABLE 1-continued

Detection Of HBsAg And HBeAg Produced By
HepG2 Cells Transfected With Wild Type HBV And HBVtat Amounts (S/N[b] ± Standard Deviation)

| Samples[a] | HBsAg | HBeAg |
|---|---|---|

[b]HBsAg and HBeAg produced were determined as S/N values as described by the manufacturer (Abbott). ≧2.00 S/N is the cut off rate for positive results. According to the manufacturer, ≧7.00 S/N of HBsAg detected is equivalent to 4–15 ng/ml concentration but the absolute concentration of HBeAg is not determined.

Based on the amounts of HBsAg and HBeAg produced from HBVtat, expression of other HBV genes does not seem to be affected by the tat insertion. The data presented herein indicates that the HBVtat recombinant can replicate and form viral particles since extracellular viral particles have been harvested and assayed for endogenous polymerase activity as well as for the viral DNA. Detection of the extracellular viral particles also indicates that the expression of the L protein is not affected by the tat insertion because the L protein is absolutely necessary for virion assembly [Bruss and Ganem (1991) Proc. Natl. Acad. Sci. USA 88:1059 and Bruss and Vieluf (1995) J. Virol. 69:6652].

EXAMPLE 6

Construction of HBV Vectors and Insertion of Foreign Genes

The preceding examples demonstrated the ability to express a functional foreign gene product in the context of the HBV genome. To accommodate foreign or heterologous gene sequences up to about 2.0 to 2.2 kb in length, HBV vectors lacking the majority of the pol ORF are constructed. These vectors retain regulatory sequences required for replication, packaging and expression of the inserted foreign gene (i.e., these vectors contain DR1, DR2, the packaging signal, enhancers, the core/pol promoter and the preS1 promoter). Because it has been reported that the HBV X gene is strongly associated with the development of hepatocellular carcinoma [Höhne et al. (1990) EMBO J. 9:1137 and Koike et al. (1989) Mol. Biol. Med. 6:151], the HBV backbone employed in the HBV vectors preferentially lacks the ability to express the X gene product.

a) Construction of a Recombinant HBV Vector Lacking A Functional X Gene

Conveniently, the X− form of HBV in plasmid pTHBVTX− (described in Ex. 2) may be used as a source of an HBV genome lacking a functional X gene. The X mutation present in pTHBVTX− is placed into a HBV genome lacking the tat gene as follows. pTHBVTX− is digested with SpeI and RsrII and the ~900 bp fragment containing the mutation is inserted into the large fragment obtained by digestion of pTHBV (described in Ex. 1) with SpeI and RsrII to generate pTHBVX−. pTHBVX− is then digested with SphI and the linear pTHBVX− molecule is inserted into the SphI site of pT7T3 18U to generate pTHBVX−/SphI. pTHBVX−/SphI is then digested with BstEII and EcoRV and the ~4.3 kb fragment containing 1.44 kb of HBV sequences and vectors sequences present between the EcoRI site of HBV is removed. The plasmid, which now lacks the majority of the pol ORF (i.e., sequences located between the BstEII site at nt 2823 and the EcoRV site at nt 1042 of the circular map of HBV), can then be circularized using methods known to the art including the use of synthetic oligonucleotides to provide a polylinker region between the BstEII end and the EcoRV end. As the art well knows an infinite number of suitable polylinker sequences may be employed. The preferred polylinker will contain recognition sites for restriction enzymes which do not cut within either the HBV sequences present on the vector or within the gene of interest to be inserted. It is not required that a polylinker be used to permit insertion of the gene of interest. The gene of interest may be obtained by PCR amplification using primers which allow the insertion of the gene of interest into the BstEII and EcoRV sites present on the open (i.e., not circularized) vector. Once the vector has been circularized (either by insertion of a polylinker followed by insertion of the gene of interest or by insertion of the gene of interest), the vector is digested with SphI and a head to tail dimer containing the HBV sequences and the gene of interest (the dimer is joined at the SphI site) is inserted into pT7T3 18U vector (Pharmacia). The gene of interest may be expressed using endogenous HBV promoters (e.g., preS1 promoter) or alternatively, it may be expressed using a heterologous promoter. If a heterologous promoter is employed, this promoter is joined to the gene of interest in such a manner that the transcription from the heterologous promoter is in the same orientation as that of the HBV promoters (e.g., the preS1 promoter).

The resulting plasmid, pΔHBVX−-d/GOI, retains regulatory HBV sequences required for replication, packaging and expression of the inserted foreign gene (GOI, gene of interest); however, the deleted HBV genome contained on this plasmid is replication-defective (due to an inablity to produce functional pol). In order to produce virus particles containing the replication-defective recombinant HBV genome, the recombinant HBV is cotransfected into cells along with plasmids which encode HBV pol and surface antigen gene products as described below.

b) Packaging of the Recombinant HBV Genome

To encapsidate or package the recombinant HBV genome containing the gene of interest, HepG2 cells are cotransfected with the recombinant HBV construct containing the gene of interest and plasmids containing the HBsAg genes (pSV45H, described in Ex. 2) and the HBV pol gene (pCHBVP, described in Ex. 2) using any suitable transfer protocol (e.g., lipofection as described in Example 2). Four to five days after transfection, the culture medium from the cotransfected HepG2 cells is collected and extracellular recombinant viral particles are collected as described in Example 4.

The presence of infectious recombinant HBV particles is demonstrated by infection of HepG2 cells and examination of the infected cells for the presence and/or expression of the gene of interest. Because HepG2 cells have been reported to be refractory to infection by HBV particles unless the viral particles are first treated with V8 protease, the recombinant HBV particles are treated with V8 protease before they are used to infect HepG2 cells.

c) Protease Treatment of Recombinant HBV Particles

V8 protease treatment is carried according the method of Lu et al. [J. Virol. (1996) 70:2277]. Briefly, recombinant HBV particles are collected as described in Ex. 4 with the exception that the precipitated viral particles are resuspended in 0.05M potassium phosphate buffer (pH 7.4) at a concentration of equivalent to $2 \times 10^9$ HBV DNA molecules per ml (HBV DNA may be quantitated using DNA dot blots, a standard technique in the field). The resuspended recombinant HBV particles are then incubated with 1.2 mg V8 protease per ml at 37° C. overnight. Protease is then removed by ultracentrifugation through a 20% sucrose cushion at 36,000 rpm in a SW41 rotor (Beckman) at 10° C. for 8 hr. Recombinant virus particles (i.e., virions) are then resuspended in 150 μl PBS prior to infection of HepG2 cells.
d) Infection of HepG2 Cells With Protease-Treated Recombinant HBV Particles HepG2 cells are maintained as described in Example 2. Semiconfluent HepG2 cells are washed with HepG2 medium (pH adjusted to 5.5 with MES) and approximately $10^7$ virions/ml in HepG2 medium (pH 5.5) are added and the cells are incubated for 12 hr at 37° C. The cells are then washed twice with HepG2 medium (pH 5.5), followed by three washes with PBS and final with a wash using HepG2 medium to remove unabsorbed virus. The cells are then cultured in HepG2 medium.
e) Demonstration of Transfer of Gene Transfer Via Infection With Recombinant HBV Virions Five to eight days after infection, cells are removed by treatment with trypsin and the presence of intracellular recombinant HBV DNA and/or RNA is demonstrated using standard techniques [e.g., preparation of total DNA followed by Southern blot analysis, lysis of a small aliquot of cells (2,000 to 4,000) in water followed by PCR analysis using primers capable of hybridizing to HBV sequences and/or the gene of interest, preparation of total or polyA+ RNA followed by Northern blot analysis]. The presence of intracellular recombinant HBV vector DNA or RNA produced by the recombinant HBV genome is indicative of infection of HepG2 cells by the recombinant HBV and thus gene transfer by the recombinant HBV virions.

EXAMPLE 7

Construction of Non-Infectious Recombinant HBV Vectors for the Delivery of Genes Without the Need to Package the HBV Vector In Example 6, the production and packaging of recombinant replication defective HBV vectors capable of being packaged into infectious particles was described. An alternative approach to using the HBV genome as a vector for gene therapy (i.e., the transfer of genes), is the use of non-infectious HBV vectors which may be either replication competent or replication defective; preferably these vectors are replication competent (i.e., capable of synthesizing additional copies of the viral genome to allow persistent cccDNA in the transduced cell). These vectors cannot be packaged into viral particles because the size of the recombinant viral genome exceeds the packaging limit.

In this approach, the recombinant HBV vector contains at least the HBV pol, core and surface antigen genes (and therefore DR1 and DR2) as well as the gene of interest (the core and pol genes are required to establish persistent ccc viral DNA formation in the transduced cell). The gene of interest is inserted into the tether region of the pol gene as described for the production of HBVtat in Example 1 (i.e., the insertion of the tat gene sequences into the tether region). Sequences encoding the gene of interest will contain the ATG or start codon for the gene of interest but will lack the stop codon located at the 3' end of the gene of interest. Because the resulting recombinant HBV genome is not intended to be packaged into viral particles, there is no limit to size of the foreign gene sequences which can be inserted. The recombinant HBV vector containing the gene of interest is contained within a plasmid and super-coiled plasmid DNA is injected (as naked DNA) into the liver of the recipient. Given the lifecycle of HBV (i.e., the presence of the viral DNA as ccc DNA in the nucleus, the presence of viral RNA in the cytoplasm and the transport of reverse transcribed viral DNA back into the nucleus for the production of additional ccc viral DNA), the recombinant HBV genome would persist in the transduced liver cells (which are essentially non-dividing cells) allowing long term expression of the gene of interest.

As discussed in Example 6, the expression of the HBV X gene is associated with the development of hepatocellular carcinoma therefore the HBV backbone employed is preferentially incapable of expressing the X gene product. The X⁻ form of HBV in plasmid pTHBVX⁻ is used as the source of an HBV genome lacking a functional X gene (construction described in Example 6; this genome contains a mutated X gene and lacks the tat insert present in pTHBVTX⁻). The desired genome of interest maybe inserted into the BstEII site of pTHBVX⁻. The gene of interest is inserted in such a manner as to maintain the reading frame of the pol gene using techniques known to the art (i.e., the start codon of the gene of interest is in frame with the pol gene and the gene of interest lacks a stop codon). A plasmid containing a dimeric form of pTHBVX⁻ containing the gene of interest is generated as described in Example 1 (i.e., a head to tail dimer fused at the EcoRI site within the pol gene) to allow expression of the recombinant virus. Because the insertion of a gene of interest into the pol gene may result in the production of a gene product of interest/pol fusion protein or pol/gene product of interest/pol fusion protein (as described above for expression of Tat within the HBVtat virus), the resulting pol fusion protein may have diminished pol activity as compared to wild-type pol. In this case, sequences encoding the wild-type pol gene under the transcriptional control of an enhancer/promoter capable of high level expression in mammalian (preferably human) liver cells are inserted into the plasmid containing dimer of the recombinant X⁻ HBV genome; the wild-type pol gene cassette is inserted 3' or downstream of the recombinant HBV sequences and in the same transcriptional orientation as the recombinant HBV sequences. Suitable enhancer/promoters for driving the expression of the wild-type pol gene in liver cells include, but are not limited to, the CMV-IE enhancer/promoter, the human elongation factor 1α gene enhancer/promoter (SEQ ID NO:15), the SV40 enhancer/promoter, the RSV LTR, the α-fetoprotein gene enhancer/promoter and a recombinant MuLV LTR containing CMV-IE/HIV-1 TAR sequences (SEQ ID NO:16) (Robinson et al. (1995), supra]. The insertion of the wild-type pol gene cassette permits trans-complementation of the recombinant HBV virus containing the pol/gene of interest fusion.

In order to reduce the likelihood that liver cells transduced with the above recombinant HBV vectors would be subject to attack from the recipient's immune system due to expression of HBV surface antigens, the HBV genome is mutated to abolish expression of the surface antigens while maintaining expression of the pol/gene of interest fusion gene. Site directed mutagenesis is employed to change the start codon (ATG) for the S gene (which encodes the smallest surface antigen) to ACG. The ATG for the S gene is located at nucleotides 157–159 in SEQ ID NO:1; thus, the T at nt 158 is changed to a C. To abolish expression of the preS1 gene, the ATG of the preS1 gene located at nucleotides 2856–2858 in SEQ ID NO:1 is changed to ACG (i.e., the T at nt 3857 is changed to a C). To abolish expression of the preS2 gene, the ATG of the preS2 gene located at nucleotides 3213–3215 in SEQ ID NO:1 is changed to ACG (i.e., the T at nt 3214 is changed to a C).

The reading frames for all three of the surface antigen genes and the pol gene overlap in such a manner that changing the ATG codons of the S, preS1 and preS2 genes results in silent substitutions in the pol gene (in each case a CAT codon in the pol gene is changed to a CAC codon; both codons encode histidine). Because the ACG codon can be used as a start codon (albeit with a lower efficiency than an ATG codon), a stop codon is inserted into the surface antigen genes in such a manner that a silent substitution in the pol gene is generated. The C residue at nucleotide number 173 in SEQ ID NO:1 is changed to an A residue to create a stop codon within the surface antigen genes while maintaining the amino acid sequence encoded by the pol gene (an ATC in the pol gene is changed to a ATA; both codons encode isoleucine).

To introduce the above non-infectious, X⁻ recombinant HBV genomes (with wild-type or mutated S genes and with or without the wild-type pol gene cassette) into the liver of recipient, plasmids containing a dimeric form of the HBV genome are grown in suitable host cells and supercoiled plasmid is prepared using standard techniques. The supercoiled plasmid containing the recombinant HBV genome is then suspended in sterile normal saline (or any other pharmacologically acceptable liquid lacking nucleases) and the suspension is injected directly into the liver of the recipient (e.g., by trans-abdominal injection). Approximately 50 µg of plasmid DNA is injected per injection site and 4 to 5 injection sites are used per liver. Expression of the gene of interest and presence of viral DNA and/or RNA is examined by removal of a small piece of liver tissue following injection (1 to 2 weeks post-injection), preparation of DNA and/or RNA followed by PCR analysis, Southern blot analysis, Northern blot analysis, detection of the product of the gene of interest using a suitable assay. In addition, expression of the gene of interest may be demonstrated by an improvement in clinical parameters in cases where the gene of interest provides a protein lacking in the recipient.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A recombinant hepatitis B virus genome comprising heterologous gene sequences which express at least one functional heterologous gene product.

2. The recombinant virus genome of claim 1, wherein said genome further comprises an endogenous viral promoter.

3. The recombinant virus genome of claim 1, wherein said viral promoter is selected from the group consisting of the core/pol promoter and the preS1 promoter.

4. The recombinant virus genome of claim 1, wherein said genome further comprises a heterologous promoter.

5. The recombinant virus genome of claim 4, wherein said heterologous promoter is selected from the group consisting of the CMV-IE promoter, the human elongation factor 1$\alpha$ gene promoter, the SV40 enhancer/promoter, the Rous sarcoma virus long terminal repeat, the $\alpha$-fetoprotein gene promoter and the recombinant Moloney murine leukemia virus long terminal repeat containing CMV-IE/HIV-1 TAR sequences listed in SEQ ID NO:16.

6. The recombinant virus genome of claim 1, wherein said genome is replication competent.

7. The recombinant virus genome of claim 1, wherein said genome is replication defective.

8. A host cell transfected with a recombinant hepatitis B virus genome comprising pol gene sequences, X gene sequences and preS1/preS2/S gene sequences and heterologous gene sequences wherein said host cell expresses at least one functional heterologous gene product.

9. The host cell of claim 8, wherein said genome is replication defective.

10. The host cell of claim 9, wherein said genome contains a deletion within the pol gene.

11. The host cell of claim 9, wherein said genome contains a deletion within the preS/preS2/S gene sequences.

12. The host cell of claim 9, wherein said genome contains a deletion within the pol gene and the preS/preS2/S gene sequences.

13. The host cell of claim 8, wherein said genome lacks a functional X gene.

14. The host cell of claim 8, wherein said genome lacks a functional S gene.

15. The host cell of claim 14, wherein said genome further lacks functional preS1/S and preS2/S genes.

16. The host cell of claim 8, wherein said genome lacks a functional S gene and a functional X gene.

17. A method for encapsidating a recombinant hepatitis B virus genome, comprising:

a) providing:

i) a recombinant hepatitis B virus genome comprising pol gene sequences, X gene sequences and preS1/preS2/S gene sequences and heterologous gene sequences wherein said recombinant genome is capable of expressing at least one functional heterologous gene product and wherein said recombinant genome lacks the ability to produce at least one viral product required for packaging said recombinant genome;

ii) at least one plasmid capable of providing in trans hepatitis B virus gene products sufficient to complement said recombinant viral genome lacking the ability to produce at least one viral product required for packaging;

iii) a liver cell in vitro; and b) introducing said recombinant hepatitis virus genome and said at least one plasmid into said liver cell under conditions such that said recombinant hepatitis virus genome is encapsidated into viral particles.

18. The method of claim 17, wherein said liver cell is selected from the group consisting of human liver cells, avian liver cells, non-human primate liver cells, and rodent liver cells.

19. The method of claim 17, wherein said recombinant virus genome contains a deletion within the pol gene.

20. The method of claim 19, wherein said plasmid encodes the product of the hepatitis B virus pol gene.

21. The method of claim 17, wherein said recombinant virus genome contains a deletion within the preS/preS2/S gene sequences.

22. The method of claim 21, wherein said plasmid encodes the products of the hepatitis B virus preS/preS2/S gene sequences.

23. The method of claim 17, wherein said recombinant virus genome contains a deletion within the pol gene and the preS/preS2/S gene sequences.

24. The method of claim 17, wherein said plasmid encodes the products of the hepatitis B virus preS/preS2/S gene sequences and the product of the hepatitis B virus pol gene.

25. The method of claim 17, wherein said recombinant virus genome lacks a functional X gene.

* * * * *